(12) United States Patent
Engler et al.

(10) Patent No.: US 6,392,069 B2
(45) Date of Patent: *May 21, 2002

(54) COMPOSITIONS FOR ENHANCING DELIVERY OF NUCLEIC ACIDS TO CELLS

(75) Inventors: Heidrun Engler, San Diego, CA (US); Tattanahalli L. Nagabhushan, Parsippany; Stephen Kenneth Youngster, Piscataway, both of NJ (US)

(73) Assignee: Canji, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/112,074

(22) Filed: Jul. 8, 1998

Related U.S. Application Data

(63) Continuation-in-part of application No. 08/889,355, filed on Jul. 8, 1997, which is a continuation-in-part of application No. 08/584,077, filed on Jan. 8, 1996, now Pat. No. 5,789,244.

(51) Int. Cl.[7] .................................................. C07J 53/00

(52) U.S. Cl. ............................................ 552/509; 536/5

(58) Field of Search ........................... 514/44; 424/93.1; 552/509; 536/5

(56) References Cited

U.S. PATENT DOCUMENTS

| | | |
|---|---|---|
| 5,013,556 A | 5/1991 | Woodle et al. |
| 5,108,921 A | 4/1992 | Low et al. |
| 5,166,320 A | 11/1992 | Wu et al. |
| 5,213,804 A | 5/1993 | Martin et al. |
| 5,279,833 A | 1/1994 | Rose |
| 5,283,185 A | 2/1994 | Epand et al. |
| 5,334,761 A | 8/1994 | Gebeyehu et al. |
| 5,346,701 A | 9/1994 | Heiber et al. |
| 5,521,291 A | 5/1996 | Curiel et al. |
| 5,542,935 A | 8/1996 | Unger et al. |
| 5,552,309 A | 9/1996 | March |
| 5,554,386 A | 9/1996 | Groman et al. |
| 5,578,475 A | 11/1996 | Jessee |
| 5,580,859 A | 12/1996 | Felgner et al. |
| 5,589,466 A | 12/1996 | Felgner et al. |
| 5,601,818 A | 2/1997 | Freeman et al. |
| 5,631,236 A | 5/1997 | Woo et al. |
| 5,804,566 A | 9/1998 | Carson et al. ............... 514/44 |
| 6,210,939 B1 | 4/2001 | Gregory et al. |

FOREIGN PATENT DOCUMENTS

| | | |
|---|---|---|
| WO | WO 92/06180 | 4/1992 |
| WO | WO 93/14188 | 7/1993 |
| WO | WO 93/19768 | 10/1993 |
| WO | WO 93/20221 | 10/1993 |
| WO | WO 94/06922 | 3/1994 |
| WO | WO 94/06923 | 3/1994 |
| WO | WO 97/05209 | 2/1997 |
| WO | WO 97/27599 | 7/1997 |

OTHER PUBLICATIONS

Verma et al. Nature, vol. 389, pp. 239–242, Sep. 18, 1997.*
Ross et al. Human Gene Therapy, vol. 7, pp. 1781–1790, Sep. 1996.*
Marshall Science, vol. 269, pp. 1050–1055, 1995.*
Shawaphun et al., Chemical evidence for transbilayer movement of molecular umbrellas, 1999, J. Am. Chem. Soc., vol. 121, pp. 5860–5864.*
Aungst, B. and Rogers, N., "Comparison of the effects of various transmucosal absorption promoters on buccal insulin delivery," *Inter. J. of Pharmaceutics*, 53:227–235 (1989).
Janout, V. et al., "Evidence for Highly Cooperative Binding between Molecular Umbrella—Spermine Conjugates and DNA," *Bioconjugate Chem.*, 8:891–895 (1997).
Janout, V. et al., "Molecular Umbrellas," *J. Am. Chem. Soc.* 118:1573–1574 (1996).
Helenius et al. (1979) "Properties of Detergents" In: *Methods in Enzymology*, vol. 56, 734–749.
Abe, A. et al., "Transduction of a Drug–Sensitive Toxic Gene into Human Leukemia Cell Lines with a Novel Retroviral Vector," *P.S.E.B.M.* 203:354–359 (1993).
Arteaga, C.L. et al., "Tissue–targeted Antisense c–fos Retroviral Vector Inhibits Established Breast Cancer Xenografts in Nude Mice," *Cancer Research* 56:1098–1103 (1996).
Banerjee, A. et al., "Changes in Growth and Tumorigenicity following Reconstitution of Retinoblastoma Gene Function in Various Human Cancer Cell Types of Microcell Transfer of Chromosome 13," *Cancer Research* 52:6297–6304 (1992).
Bass, C. et al., "Recombinant adenovirus–mediated gene transfer to genitourinary epithelium in vitro and in vivo," *Cancer Gene Ther.* 2(2):97–104 (1995).
Blixt, Y. et al., "Enhancement of intracellular uncoating of adenovirus in HeLa cells in the presence of benzyl alcohol as a membrane fluidizer," *Arch. Virol.* 129:265–277 (1993).
Boulikas, "Gene Therapy of Prostate Cancer: p53, Suicidal Genes, and Other Targets," *Anticancer Research* 17:1471–1506 (1997).
Brewster, S.F. et al., "Gene Therapy in Urological Oncology: Principles, Strategies and Potential," *Eur. Urol.* 25:177–182 (1994).

(List continued on next page.)

Primary Examiner—Michael C. Wilson
(74) *Attorney, Agent, or Firm*—Townsend and Townsend and Crew, LLP

(57) ABSTRACT

This invention provides methods and compositions for enhancing transfer of an agent into a cell. The agents can include polypeptides, polynucleotides such as genes and antisense nucleic acids, and other molecules. In some embodiments, the agents are modulating agents that can modulate a cellular activity or function when introduced into the cell. The methods and compositions are useful for introducing agents into individual cells, as well as cells that are present as a tissue or organ.

5 Claims, 35 Drawing Sheets

OTHER PUBLICATIONS

Cairns, P. et al., "Loss of heterozygosity at the RB locus is frequent & correlates with muscle invastion in bladder carcinoma," *Oncogene* 6:2305–2309 (1991).

Cooper, M.J. et al., "Safety–modified episomal vectors for human gene therapy," *Proc. Natl. Acad. Sci. U.S.A.* 94:6450–6455 (1997).

Curiel, D.T. et al., "Adenovirus enhancement of transferrin–polylysine–mediated gene delivery," *Proc. Natl. Acad. Sci. U.S.A.* 88:8850–8854 (1991).

Dalesandro, J. et al., "Cardiac and Pulmonary Replacement," *J. Thoracic Cardio. Surg.* 111(2):416–422 (1996).

Fujimoto, K. et al., "Frequent Association of p53 Gene Mutation in Invasive Bladder Cancer," *Cancer Research* 52:1393–1398 (1992).

Ginsberg, H.S. et al., "Role of early region 3 (E3) in pathogenesis of adenovirus disease," *Proc. Natl. Acad. Sci. U.S.A.* 86:3823–3827 (1989).

Good; N.E. et al., "Hydrogen Ion Buffers for Biological Research," *Biochemistry* 5(2):467–477 (1966).

Goodrich, D.W. et al., "Expression of the Retinoblastoma Gene Product in Bladder Carcinoma Cells Associates with a Low Frequency of Tumor Formation," *Cancer Research* 52:1968–1973 (1992).

Greney, H. et al., "Characterizatino of Imidazoline Binding Protein(s) Solubilized from Human Brainstem: Studies with [$^3$H] Idazoxan and [$^3$H]Clonidine," *Neurochem. Int.* 25(2):183–191 (1994).

Greenberg, R. et al., "Intravesical AD32 (N–Trifluoroacetyladriamycin–14–Valerate) in the Treatment of Patients with Refractory Bladder Carcinoma—Clinical Efficacy, Pharmacology, and Safety," *Proc. Am. Urol. Assoc.* 153 Supp 233A:19 (1995).

Hemström, C. et al., "Gene Product of Region E4 of Adenovirus Type 5 Modulates Accumulation of Certain Viral Polypeptides," *J. Virol.* 62(9):3258–3264 (1988).

Huang, S. et al., "A cellular protein that competes with SV40 T antigen for binding to the retinoblastoma gene product," *Nature* 350:160–162 (1991).

Ji, W. et al., "Inhibition of hepatitis B virus by retroviral vectors expressing antisense RNA," *J. Viral Hep.* 4:167–173 (1997).

Kaneda, Y. et al., "Prevention of Restenosis by Gene Therapy," *Annals N.Y. Acad. Sci.* 811:299–310 (1997).

Koc, O.N. et al., "Transfer of Drug Resistance Genes Into Hemotopoietic Progenitors to Improve Chemotherapy Tolerance," *Sem. Oncol.* 23(1):46–64 (1996).

Lee, R.J. et al., "Lipidic Vector Systems for Gene Transfer," *Crit. Rev. Ther. Drug Carrier Sys.* 14(2):173–206 (1997).

Li, Q. et al., "Assessment of Recombinant Adenoviral Vectors for Hepatic Gene Therapy," *Hum. Gene. Ther.* 4:403–409 (1993).

Makarov, S.S. et al., "Suppression of experimental arthritis by gene transfer of interluekin 1 receptor antagonist cDNA," *Proc. Natl. Acad. Sci. U.S.A.* 93:402–406 (1996).

Marshall, E., "Gene Therapy's Growing Pains," *Science* 269:1050–1055 (1995).

Miller, N. et al., "Targeted vectors for gene therapy," *FASEB J.* 9:190–199 (1995).

Monson, F.C. et al., "Indigocarmine as a quantitative indicator of urothelial integrity," *J. Urol.* 145:842–845 (1991).

Morris, B.D. et al., "Adenoviral–mediated gene transfer to bladder in vivo," *J. Urol.* 152:506–509 (1994).

Murayama, Y. et al., "Antisense Oligonucleotides to p53 Tumor Suppressor Suppress the Induction of Apoptosis by Epidermal Growth Factor in NCI–H 596 Human Lung Cancer Cells," *Antisense Nucl. Acid Drug Devel.* 7:109–114 (1997).

Niidome, T. et al., "Binding of Cationic α–Helical Peptides to Plasmid DNA and Their Gene Transfer Abilities into Cells," *J. Biol. Chem.* 272(24):15307–15312 (1997).

Nolta, J.A. et al., "Transduction of pluripotent human hematopoietic stem cells demonstrated by clonal analysis after engraftment in immune–deficient mice," *Proc. Natl. Acad. Sci. U.S.A.* 93:2414–2419 (1996).

Parsons, C.L. et al., "Bladder surface glycosaminoglycans: an epithelial permeability barrier," *J. Urol.* 143:139–142 (1990).

Pinnaduwage, P. et al., "Use of a quarternary ammonium detergent in liposome mediated DNA transfection of mouse L–cells," *Biochim. Biophys. Acta* 985:33–37 (1989).

Plank, C. et al., "The Influence of Endosome–disruptive Peptides on Gene Transfer Using Synthetic Virus–like Gene Transfer Systems," *J. Biol. Chem.* 269(17):12918–12924 (1994).

Raper, S.E. et al., "Safety and Feasibility of Liver–Directed Ex Vivo Gene Therapy for Homozygous Familial Hypercholesterolemia," *Annals Surgery* 223(2):116–126 (1996).

Rosenberg, S.A., "The Immunotherapy and Gene Therapy of Cancer," *J. Clin. Oncol.* 10(2):180–199 (1992).

Sandberg, J.W. et al., "Improving Access to Intestinal Stem Cells as a Step Toward Intestinal Gene Transfer," *Human Gene Therapy* 5:323–329 (1994).

Spandidos, D.A. et al., "Expression of the Normal H–ras1 Gene can Suppress the Transformed and Tumorigenic Phenotypes Induced by Mutant ras Genes," *Anticancer Research* 10:1543–1554 (1990).

Takahashi, R. et al., "The retinoblastoma gene functions as a growth and tumor suppressor in human bladder carcinoma cells," *Proc. Natl. Acad. Sci. U.S.A.* 88:5257–5261 (1991).

Vidal, P. et al., "Nouvelle stratégie pour vectorisation d–ARN dan des cellules de mammifères. Utilisation d'un vecteur peptidique," *CR Acad. Sci III* 32:279–287 (1997).

Wills, K.N. et al., "Development and Characterization of Recombinant Adenoviruses Encoding Human p53 for Gene Therapy of Cancer," *Hum. Gene Ther.* 5:1079–1088 (1994).

Wills, K.N. et al., "Gene therapy for hepatocellular carcinoma: Chemosensitivity conferred by adenovirs–mediated transfer of the HSV–1 thymidine kinase gene," *Cancer Gene Ther.* 2(3):191–197 (1995).

Wu, G.Y. et al., "Receptor–mediated Gene Delivery and Expression in Vivo," *J. Biol. Chem.* 263(29):14621–14624 (1988).

Xiao, X. et al., "Adeno–associated virus (AAV) vector antisense gene trasnfer in vivo decreases $GABA_A$ $α_1$ containing receptors and increases inferior collicular seizure sensitivity," *Brain Res.* 756:76–83 (1997).

Yew, N.S. et al., "Optimization of Plasmid Vectors for High–Level Expression in Lung Epithelial Cells," *Human Gene Therapy* 8:575–584 (1997).

Cancer Facts & Figures 1995, *Am. Canc. Soc.* 5–11 (1995).

\* cited by examiner

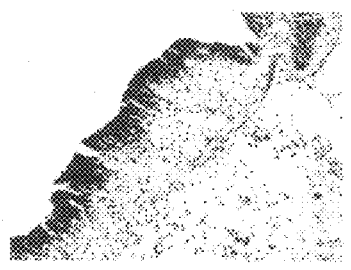 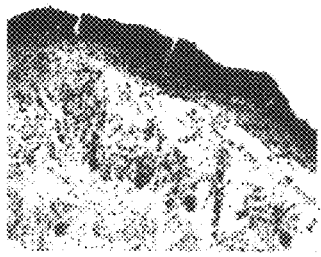 
VPBS  Ethanol  DMSO
FIG. 2.

| $10^7$ | $10^8$ | $10^9$ | $10^{10}$ | $10^{11}$ |
| FIG. 3A. | FIG. 3B. | FIG. 3C. | FIG. 3D. | FIG. 3E. |

7 mM Big Chap VPBS
FIG. 11.

 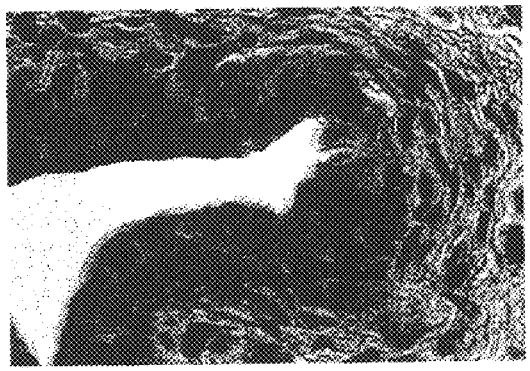
300 X　　　1200 X
FIG. 12.

Calbiochem 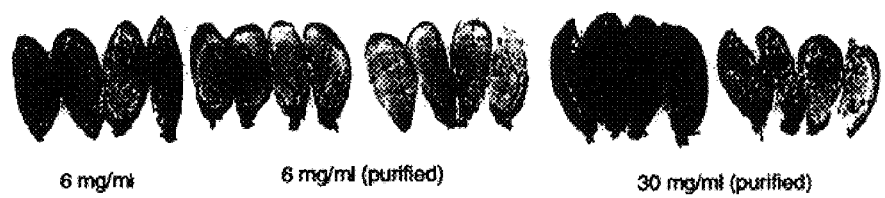
6 mg/ml      6 mg/ml (purified)      30 mg/ml (purified)
Sigma 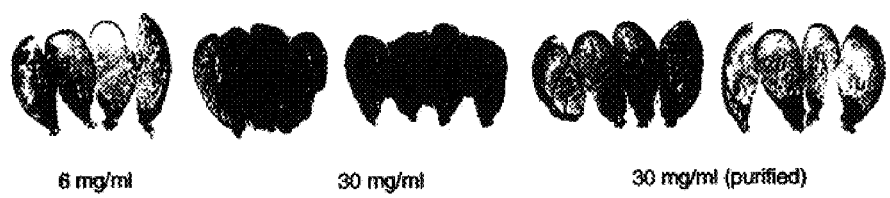
6 mg/ml      30 mg/ml      30 mg/ml (purified)
FIG. 18.

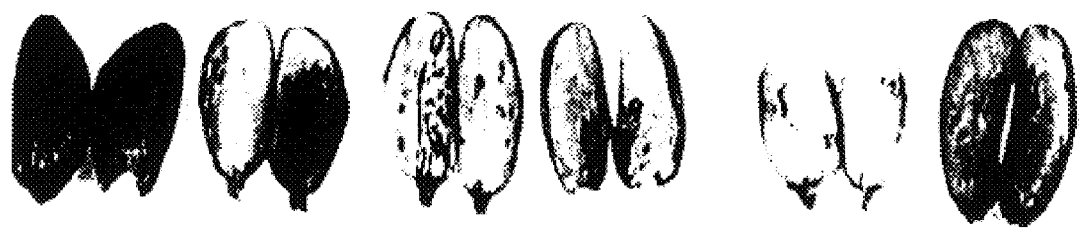
6 mg/ml BC
(Calbiochem)
6 mg/ml BC pure
(Calbiochem)
6 mg/ml BC (Sigma)
6 mg/ml Impurity II+
III
0.6 mg/ml Impurity
II+III
6 mg/ml Impurity I
FIG. 19.

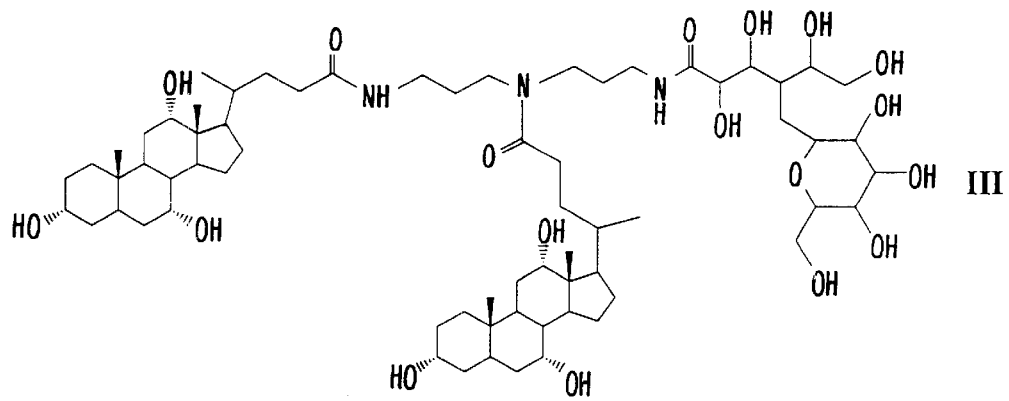
Syn3
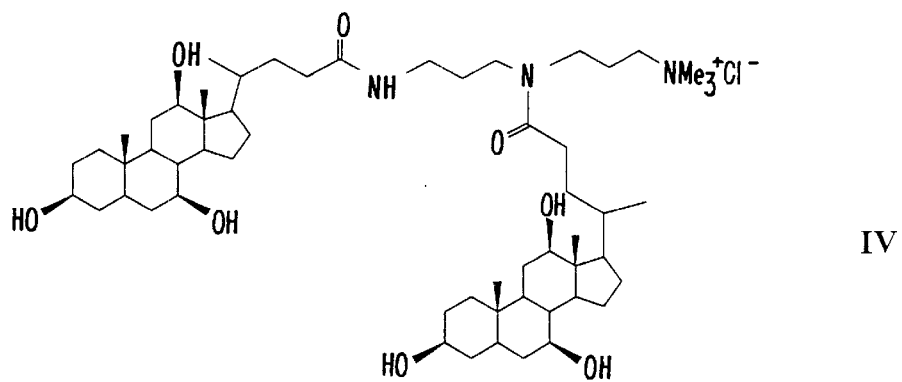
A-tma
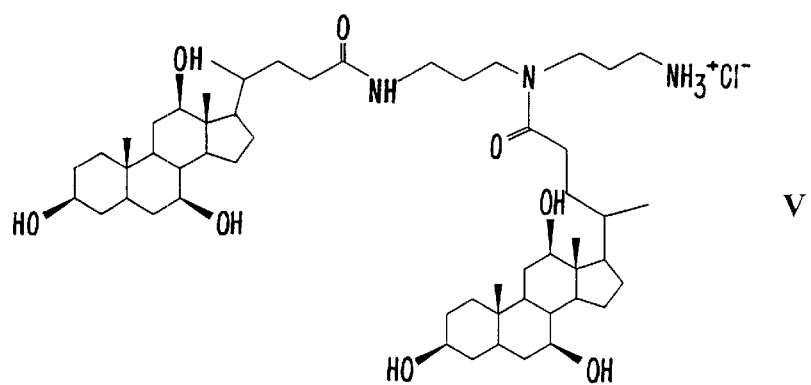
A-HCl
FIG. 21.

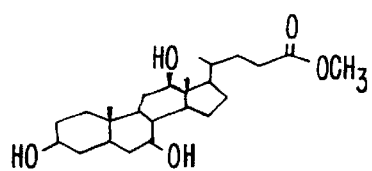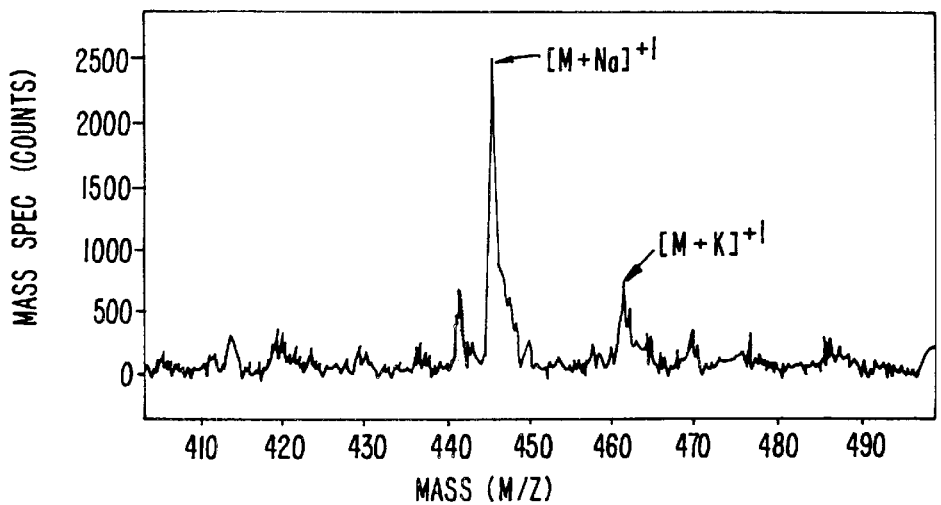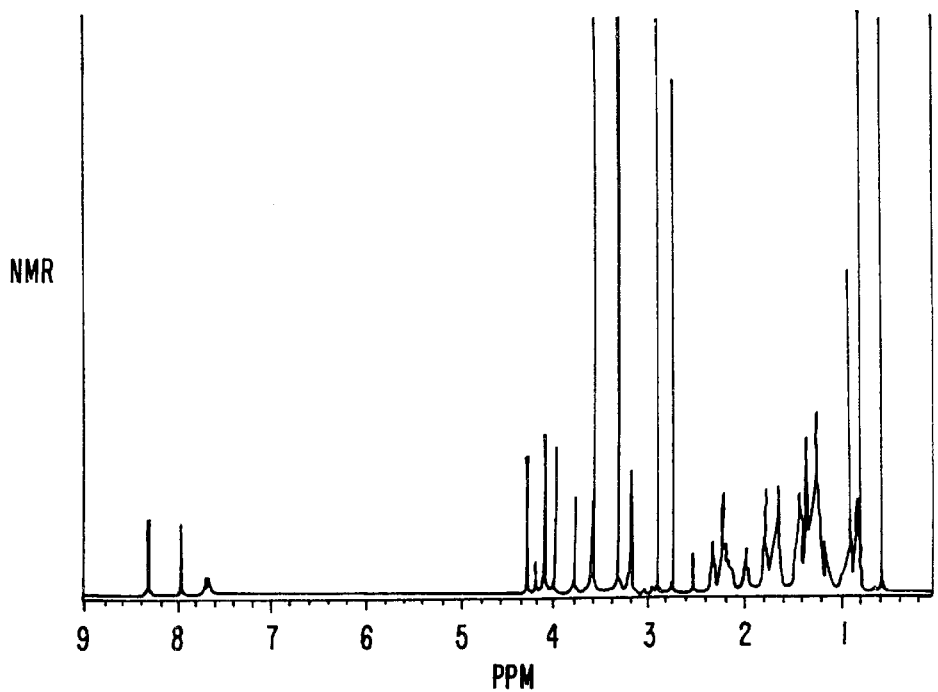
FIG. 22.

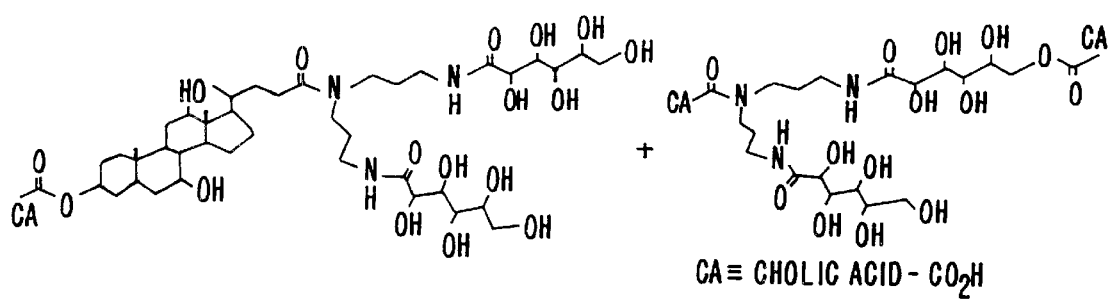
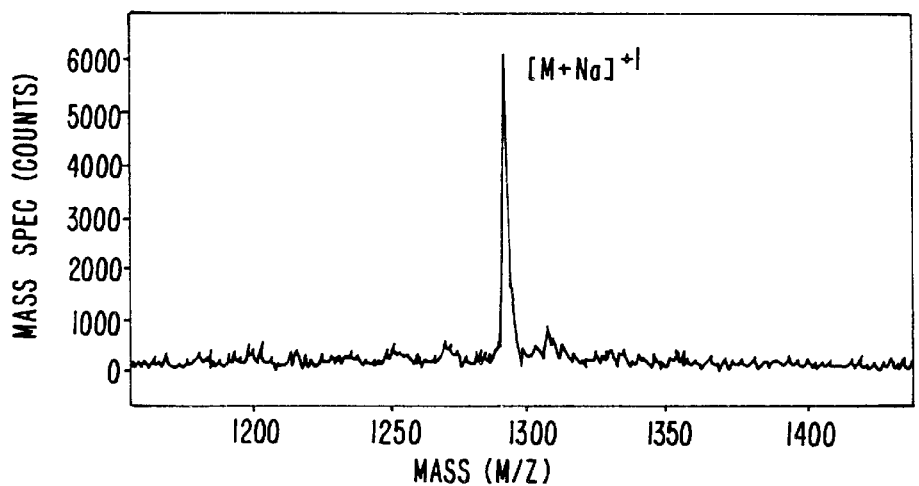
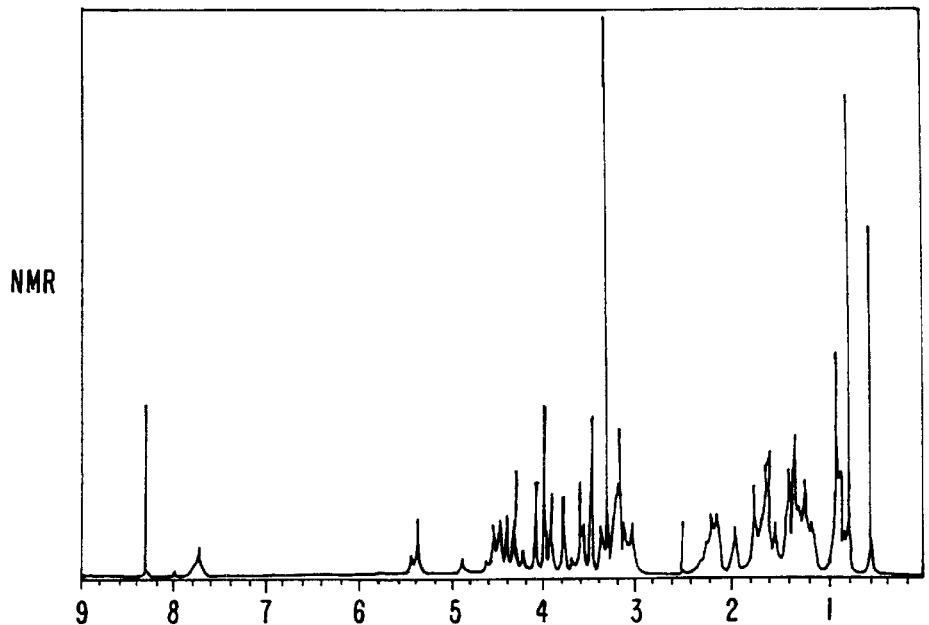
FIG. 24.

COMPOSITIONS FOR ENHANCING DELIVERY OF NUCLEIC ACIDS TO CELLS

CROSS-REFERENCE TO RELATED APPLICATIONS

This application is a continuation-in-part of U.S. Ser. No. 08/889,355, filed Jul. 8, 1997, which is a continuation-in-part of U.S. Ser. No. 08/584,077, filed Jan. 8, 1996, now U.S. Pat. No. 5,789,244 each of which is incorporated by reference in its entirety for all purposes.

BACKGROUND OF THE INVENTION

This invention pertains to the field of delivering therapeutic and other agents to cells. Genes, polypeptides, and other molecules are among the agents that can be delivered using the compounds and methods of the invention. The cells can be present individually or as a biological tissue or organ.

Delivery of a compound into a cell is a first critical step for many diagnostic and therapeutic processes. Gene therapy, for example, is a highly promising tool for therapeutic and other uses that requires delivery of a nucleic acid to a cell. For example, distinct approaches have been developed to treat neoplasms based on gene transfer methods. Methods have been developed to correct specific lesions at defined genetic loci which give rise to neoplastic transformation and progression (Spandidos et al., *Anticancer Res.* 10:1543–1554 (1990); Banerjee et al., *Cancer Res.* 52:6297–6304 (1992)). Overexpression of dominant oncogenes may be addressed using techniques to inhibit the transforming gene or gene product. Loss of tumor suppressor gene function may be approached using methods to reconstitute wild-type tumor suppressor gene function (Goodrich et al., *Cancer Res.* 52:1968–1973 (1992)). Besides these methods to achieve mutation compensation, genetic techniques have been developed to specifically and selectively eradicate tumor cells. These approaches of molecular chemotherapy rely on specific expression of toxin genes in neoplastic cells (Abe et al., *Proc Soc Exp Biol Med.* 203:354–359 (1993)). Finally, gene transfer methods have been used to achieve antitumor immunization. These methods of genetic immunopotentiation use techniques of genetic immunoregulation to enhance immune recognition of tumors. Consequently, a variety of distinct approaches have been developed to accomplish gene therapy of cancer.

A high incidence of mutations has been observed in tumor suppressor genes, such as p53 and RB, in the case of carcinoma of the bladder (Fujimoto et al., *Cancer Res.* 52:1393–1398 (1992); Cairns et al., *Oncogene* 6:2305–2309 (1991)). For such genetic lesions of tumor suppressor genes, reversion of the neoplastic phenotype can be demonstrated with replacement of the corresponding wild-type tumor suppressor gene (Spandidos, Id.; Banerjee, Id.).

Carcinoma of the bladder represents a significant source of morbidity and mortality. Bladder cancer ranks 10th in males and 12th in females in cancer related mortality (Cancer Facts and Figures, *Amer. Can. Soc.* 5:11 (1995)). Therapies available for the treatment of bladder cancer include adjuvant chemotherapy or immunotherapy, transurethral resection of superficial disease, radical cystectomy or radiotherapy which is often combined with systemic chemotherapy. Despite these therapeutic options, overall survival has not changed appreciably. (Id.) Thus, new therapeutic modalities must be developed for the treatment of bladder cancer.

Gene therapy strategies have been developed as an alternative therapeutic approach (See for example, Brewster et al., *Eur Urol* 25:177–182 (1994); Takahashi et al., *Proc Natl Acad Sci USA* 88: 5257–5261 (1991); Rosenberg, S A, *J. Clin Oncol.* 10:180–199 (1992)). Successful treatment of cancer and other conditions in a human or other animal can depend upon an adequate amount of a therapeutic agent entering the cells, and upon a large enough proportion of target cells taking up the therapeutic agent.

Many other therapeutics and other modulating agents are polypeptides or, for example, small molecules. Again, the amount of the agent that reaches a target cell population can have a great impact on the efficacy of treatment. Therefore, a need exists for compounds and methods that can enhance the amount of an agent that is delivered to a cell or a population of cells.

The present invention fulfils this and other needs.

SUMMARY OF THE INVENTION

The invention provides compounds that can enhance delivery of an agent to cells. The delivery enhancing compounds of the invention typically have a Formula I:

$$X_1 \overset{O}{\underset{\|}{C}} \overset{H}{\underset{|}{N}} (CH_2)_m \overset{}{\underset{|}{N}} (CH_2)_n \overset{H}{\underset{|}{N}} R$$
$$\overset{|}{C}=O$$
$$\overset{|}{X_2}$$

I wherein:

m and n are the same or different and each is an integer from 2–8; R is a cationic group or

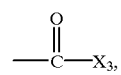

$X_1$ is selected from the group consisting of:

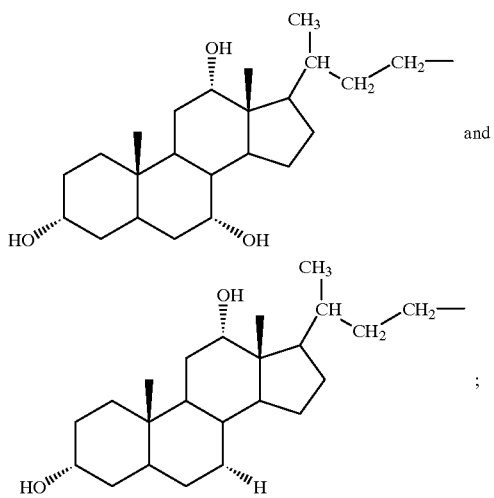

and $X_2$ and $X_3$ are each independently selected from the group consisting of a saccharide group,

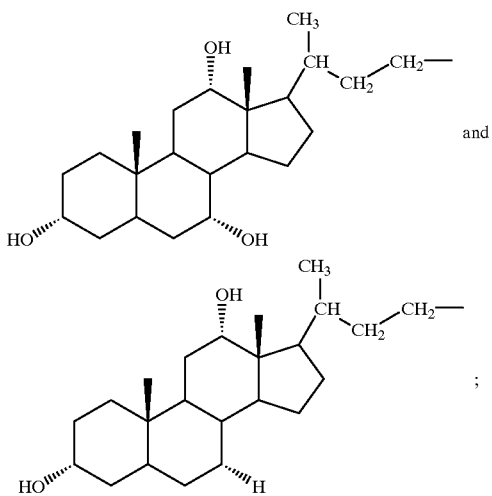

wherein at least one of $X_2$ and $X_3$ is a saccharide group when R is

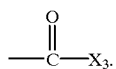

Some examples of preferred delivery enhancing compounds of the invention are those that have a Formula III, IV, or V as shown in FIG. 21.

In some embodiments, the delivery enhancing compounds have a Formula II:

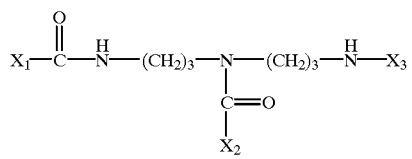

wherein $X_1$ and $X_2$ are selected from the group consisting of

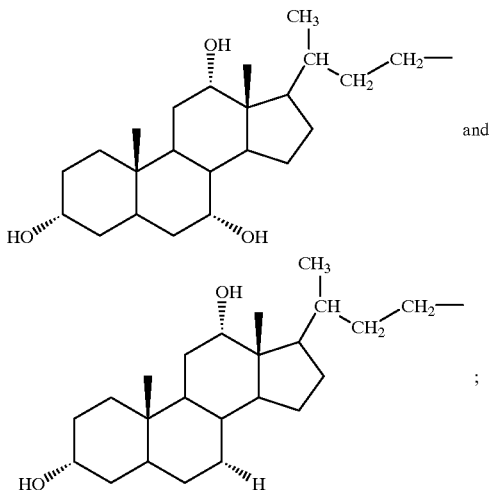

and $X_3$ is a saccharide group.

Also provided by the invention are methods of delivering an agent to cells by administering the agent to the cells in a formulation that includes a delivery enhancing compound of Formula I.

In additional embodiments, the invention provides compositions for delivering an agent to cells. The compositions include the agent to be delivered and a delivery enhancing compound of Formula I.

A further aspect of the invention is a method of treating cancer, including bladder cancer, by administering to a cell a therapeutically effective amount of a therapeutic agent that is formulated in a buffer comprising a compound of Formula I.

BRIEF DESCRIPTION OF THE DRAWINGS

FIG. 2 depicts adenovirus transgene expression in bladder epithelial cells after intravesical administration.

FIG. 11 depicts transgene transfer to pig bladder epithelium.

FIG. 12 depicts the expression of p53 in tumor tissue.

FIG. 18 is a photograph of bladder sections from rats, wherein the ability of Big CHAP (CALBIOCHEM®) and Big CHAP (Sigma) after purification to enhance gene transfer was evaluated and compared to non-purified Big CHAP from those sources as a control. The intensity of the Xgal staining indicated a reduced ability to enhance gene transfer after Big CHAP from either source had been purified by column chromatography.

FIG. 19 is a photograph of bladder sections from rats, wherein the ability of Big CHAP (CALBIOCHEM®) and Big CHAP (Sigma) after purification to enhance gene transfer was evaluated and compared to non-purified Big CHAP from those sources and to Impurities I and a combination of impurity II and impurity III. The intensity of the Xgal staining demonstrated an enhancement of gene transfer with 6 mg/ml of the combination of Impurity II and Impurity III.

FIG. 21 shows the structures of Syn3 and two water-soluble analogs of Syn3. The domain of Syn3 that is conserved in the two analogs is indicated as "A". The analogs A-TMA and A-HCl resulted from the substitution of trimethylammonium chloride (A-TMA) or hydrochloride (A-HCl) for the lactose moiety of Syn3.

FIG. 22 shows the structure, MALDI-MS, and $^1$H-NMR of Impurity 1.

FIG. 24 shows the structure, MALDI-MS, and $^1$H-NMR of Impurity 3.

DETAILED DESCRIPTION

Figure 1:
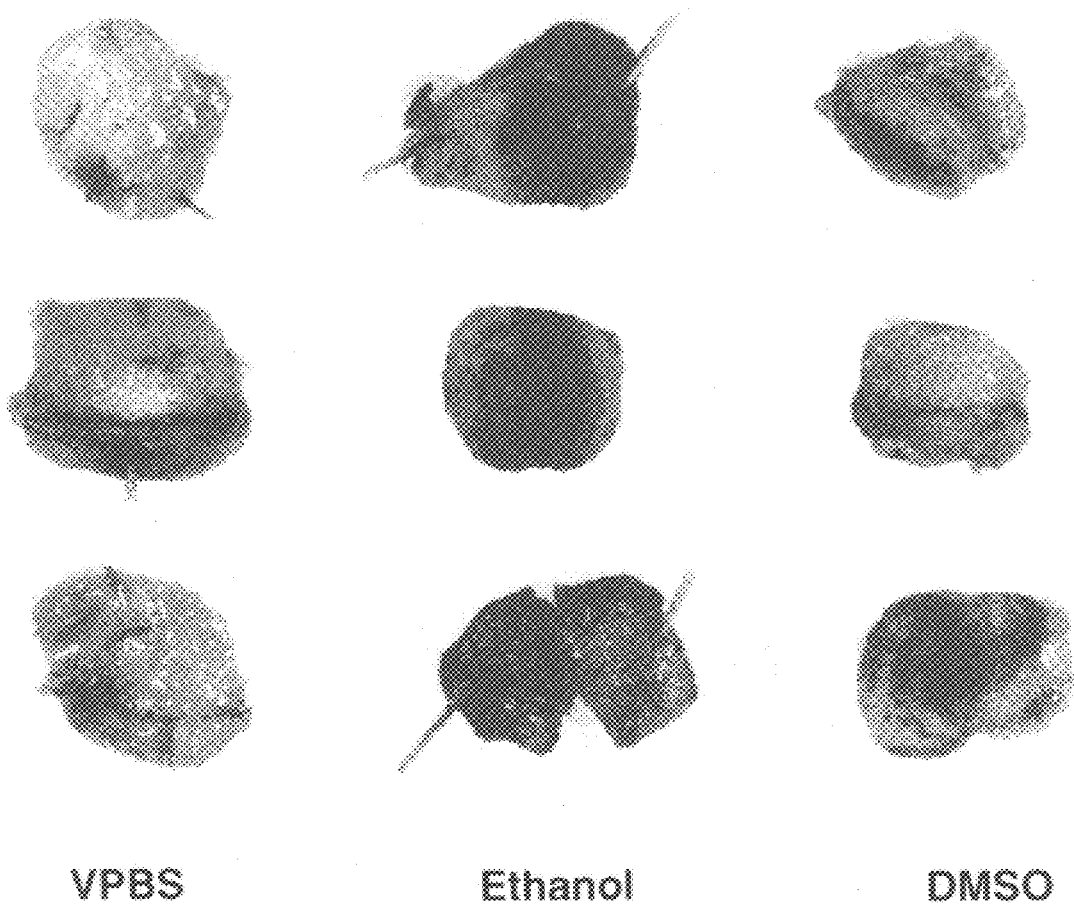
FIG. 1 depicts the influence of formulation on adenovirus mediated gene transfer and expression in the rat bladder epithelium after intravesical administration.

The present invention provides delivery enhancing compounds and formulations that enhance transport of agents into cells, such as cells present in epithelial tissues. The compounds and formulations can increase the amount of an agent, such as an agent that can modulate a cellular process associated with, for example, proliferation or a disease state, that enters a cell and/or increase the proportion of cells in a tissue or organ that take up the agent. Methods of delivering agents to cells using the delivery enhancing compounds of the invention are also provided.

The delivery enhancing compounds and methods of the invention are useful for many applications that require delivery of a molecule to a cell. For example, diagnosis and/or treatment of many disease states often requires entry of an agent into a cell that is involved in the disease process. Another example is the use of recombinant DNA technology to produce proteins of interest, either in cell culture or in a recombinant organism. Many additional examples of situations in which it is desirable to introduce a compound into a cell are known to those of skill in the art. The compounds and methods of the invention can improve the effectiveness of each of these applications due to the increased delivery of an agent of interest to a target cell or tissue.

A. Delivery Enhancing Compounds

The invention provides delivery enhancing compounds that, when formulated with an agent of interest, enhance delivery of the agent to a cell. In some embodiments, the cells are present in a tissue or organ. "A delivery-enhancing compound" refers to any compound that enhances delivery of an agent to a cell, tissue or organ. Although an understanding of the mechanism by which enhanced delivery occurs is not essential to practicing the invention, it is noted that enhanced delivery can occur by any of various mechanisms. One such mechanism may involve the disruption of the protective glycosaminoglycan (GAG) layer on the epithelial surface of the tissue or organ by the delivery enhancing compound.

Administering an agent to cells in a formulation that includes a delivery enhancing compound results in an increase in the amount of agent that is delivered to the cells, relative to the amount of agent delivered to the cells when administered in the absence of the delivery enhancing compound. "Enhanced delivery" as used herein refers to either or both of an increase in the number of copies of an agent that enter each cell or a increase in the proportion of cells in, for example, a tissue or organ, that take up the agent. In preferred embodiments, the delivery enhancing compound results in at least about a 20% increase, more preferably at least about a 50% increase, and most preferably at least about a 100% increase in delivery of an agent to a cell or population of cells compared to the amount of the agent delivered when administered to cells in the absence of the delivery enhancing compound.

One can measure whether a particular compound or formulation is effective in enhancing delivery of an agent, such as a therapeutic or diagnostic agent, to cells by various means known to those of skill in the art. For example, a detection reagent can be included in a delivery enhancing formulation which is administered to the target cells. The amount of detection reagent present in cells that are treated with the delivery enhancing formulation is compared to that detected in cells treated with a formulation that does not include a delivery enhancing compound. As an example, where the agent of interest is a gene or a vector that includes a gene, one can include in the formulation a reporter gene for which expression is readily detectable. Where the modulating agent is a polypeptide, one can test the delivery enhancing compounds by, for example, attaching a label to the polypeptide which is present in the delivery enhancing formulation and detecting the presence and amount of label that is found in target cells after administration of the formulation. Similarly, where molecules other than polypeptides and polynucleotides are to be used as the modulating agent, one can label the molecules and detect the amount of label that enters the target cell population.

Examples of delivery-enhancing compounds include, but are not limited to, detergents, alcohols, glycols, surfactants, bile salts, heparin antagonists, cyclooxygenase inhibitors, hypertonic salt solutions, and acetates. Alcohols include, for example, the aliphatic alcohols such as ethanol, N-propanol, isopropanol, butyl alcohol, acetyl alcohol. Glycols include, for example, glycerine, propyleneglycol, polyethyleneglycol and other low molecular weight glycols such as glycerol and thioglycerol. Acetates such as acetic acid, gluconic acid, and sodium acetate are further examples of delivery enhancing compounds. Hypertonic salt solutions such as 1M NaCl are also examples of delivery enhancing compounds. Examples of surfactants include sodium dodecyl sulfate (SDS) and lysolecithin, polysorbate 80, nonylphenoxypolyoxyethylene, lysophosphatidylcholine, polyethyleneglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents like silver nitrate can also be used, as can heparin-antagonists like quaternary amines such as protamine sulfate. Cyclooxygenase inhibitors such as, for example, sodium salicylate, salicylic acid, and non-steroidal antiinflammatory drugs (NSAIDS) such as indomethacin, naproxen, and diclofenac are also suitable.

Detergents that can function as delivery enhancing compounds include, for example, anionic, cationic, zwitterionic, and nonionic detergents. Exemplary detergents include, but are not limited to, taurocholate, deoxycholate, taurodeoxycholate, cetylpyridium, benalkonium chloride, ZWITTERGENT®3-14 detergent, CHAPS (3-[(3-Cholamidopropyl)dimethylammoniol]-1-propanesulfonate, hydrate, Aldrich), Big CHAP, Deoxy Big CHAP, TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

One example of a preferred delivery enhancing compound for formulations in which the agent is, for example, a nucleic acid is Big CHAP, which is a cholate derivative (see, e.g., Helenius et al. (1979) "Properties of Detergents" In: *Methods in Enzymology*, Vol.66, 734–749. In order to facilitate the improved gene transfer for nucleic acid formulations comprising commercial Big-CHAP preparations, the concentration of Big CHAP will vary based on its commercial source. When the Big CHAP is sourced from CALBIOCHEM®, it is preferred that the concentration be in a range of 2 to 10 millimolar. More preferred is 4 to 8 millimolar. Most preferred is approximately 7 millimolar. When the Big CHAP is sourced from Sigma, it is preferred that the concentration of Big CHAP be in a range of 15 to 35 millimolar. More preferred is 20 to 30 millimolar. Most preferred is approximately 25 millimolar.

In additional embodiments, the invention provides delivery enhancing compounds that have a Formula I:

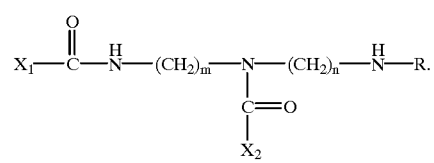

I

In Formula I, m and n can be either the same or different, and each is an integer from 2 to 8. In preferred embodiments, m and n are each independently 2 or 3.

R in Formula I is preferably a cationic group or a structure having the formula

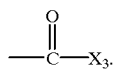

Suitable cationic groups can include any moiety that will provide a positive charge to the compound. Examples of suitable cationic groups include, but are not limited to, trimethylammonium and ammonium cations.

$X_1$ in Formula I is generally selected from the group consisting of

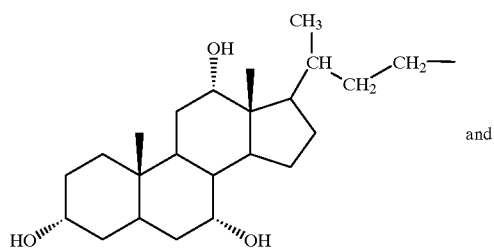

and

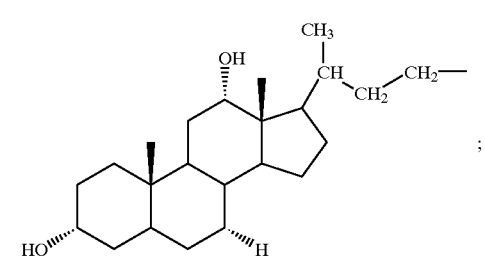

;

and $X_2$ and $X_3$ are each independently selected from the group consisting of a saccharide group,

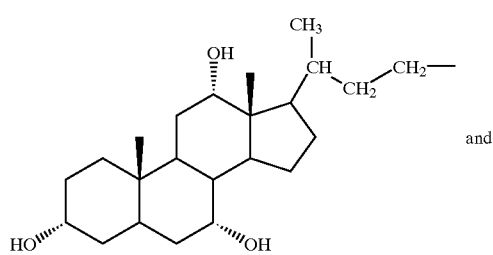

and

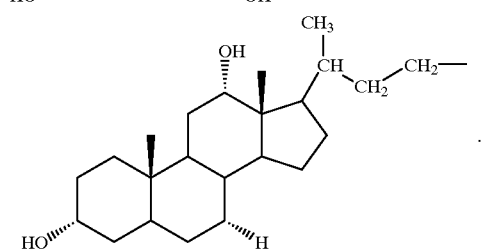

Saccharide groups that can be used in the delivery enhancing compounds of the invention can be monosaccharides or can include more than one monosaccharide linked in either homo-oligosaccharides or hetero-oligosaccharides. Preferred monosaccharides include pentose and/or hexose residues. For example, the saccharide groups can be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups. One example of a preferred saccharide group for $X_3$ is lactose.

In some embodiments, the delivery enhancing compounds of Formula I have $X_2$ and/or $X_3$ as saccharide groups that are composed of three or more monosaccharides. Preferably, the saccharide group has between one and eight monosaccharides, more preferably between one and four monosaccharides, and most preferably about two to three monosaccharides. The use of a trisaccharide, for example, can provide a compound having increased solubility.

Examples of suitable delivery enhancing compounds of the invention include, but are not limited to, compounds of Formula I in which $X_1$ and $X_2$ are both

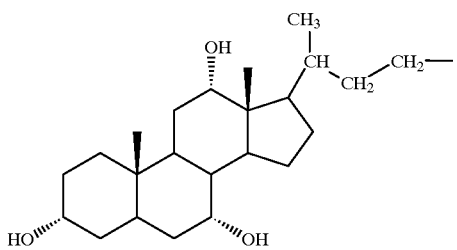

and $X_3$ is a saccharide.

Other embodiments have, for example, both $X_1$ and $X_2$ as

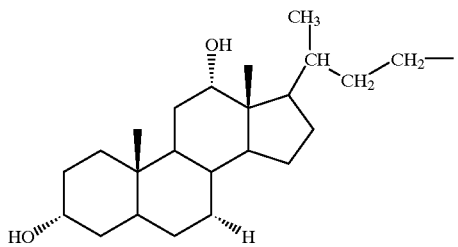

and $X_3$ is a saccharide group. Preferred compounds also include those in which n is 2 or 3, $X_1$ and $X_2$ are both

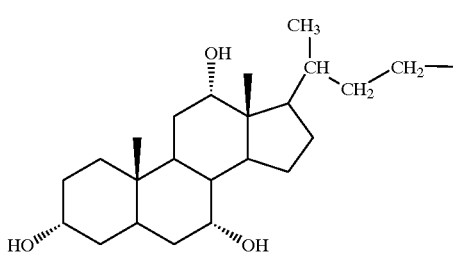

and $X_3$ is a hexose monosaccharide group; those in which n is 2 or 3, $X_1$ and $X_3$ are both

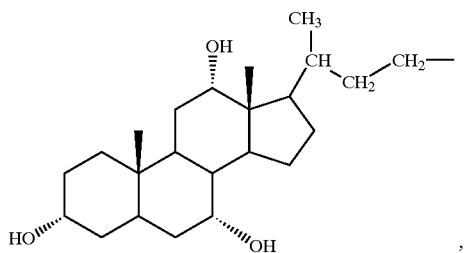

and $X_2$ is a hexose monosaccharide group; and compounds in which n is 2 or 3, $X_1$ and $X_2$ are both

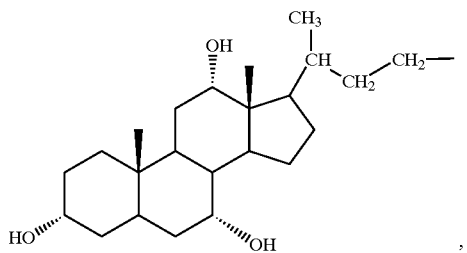

and $X_3$ is a hexose-hexose disaccharide group. Also suitable are compounds in which n is 2 or 3, $X_1$ and $X_3$ are both

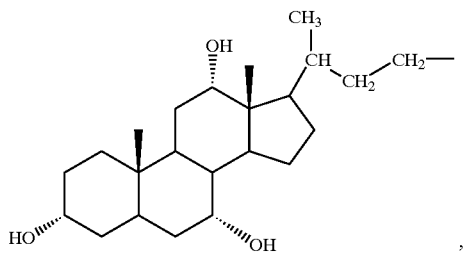

and $X_2$ is a hexose-hexose disaccharide group, or compounds in which n is 2 or 3, $X_1$ and $X_2$ are both

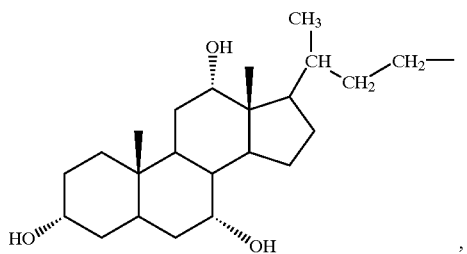

and $X_3$ is a hexose-pentose disaccharide group. Compounds of Formula I that have trisaccharide groups, in particular at the $X_3$ position, are also preferred.

One example of a preferred delivery enhancing compound of the invention is Syn3, which has Formula III as shown in FIG. 21. Syn3 is a synthetic analog of an impurity that was found in commercial preparations of Big CHAP (see, Examples). Impurities 2 and 3 of Big CHAP are also suitable for use as delivery enhancing compounds, particularly when formulated in a solubilizing buffer that contains, for example, a detergent such as Big CHAP.

For some applications, it is desirable to use delivery enhancing compounds that exhibit increased water solubility and/or delivery enhancing activity compared to other compounds. Such compounds are provided by the invention. For example, the invention provides compounds that have the Formula I in which R is a cationic group. Suitable cationic groups include, for example, tetramethyl and ammonium moieties, and salts thereof. Examples of such compounds include A-tma (Formula IV) and A-HCl (Formula V) as shown in FIG. 21. Other compounds with improved solubility and/or delivery enhancing activity include those in which the saccharide group or groups in compounds of Formula I are trisaccharides or longer.

In some embodiments, the delivery enhancing agents of the present invention have the Formula II:

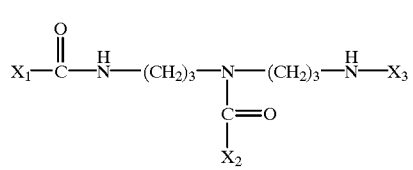

II wherein $X_1$ and $X_2$ are selected for the group consisting of

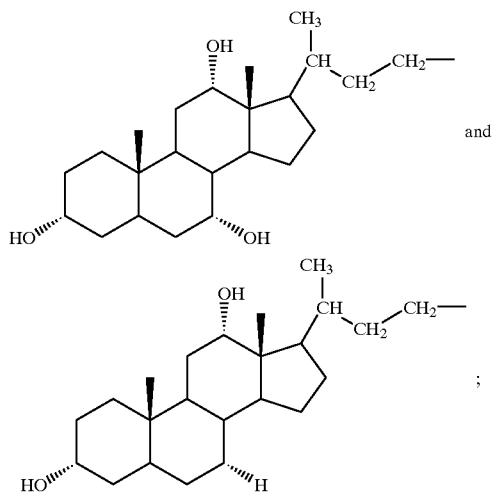

and

;

and $X_3$ is a saccharide group. Suitable saccharide groups include those discussed above for compounds of Formula I. In one example of a suitable compound, both $X_1$ and $X_2$ are

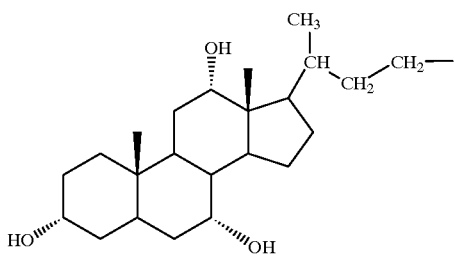

and $X_3$ is a glucose group, Additional examples of suitable compounds include, but are not limited to, those in which both $X_1$ and $X_2$ are selected from the group consisting of

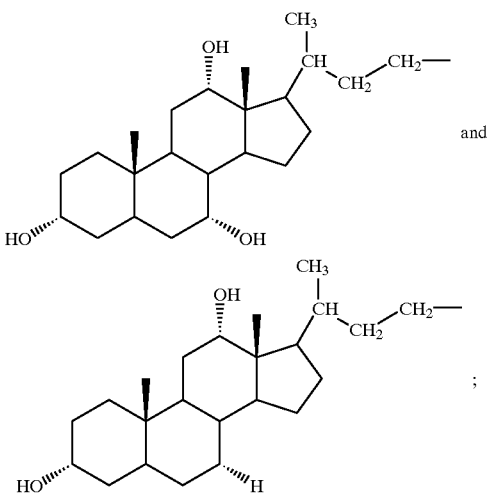

and X$_3$ is a lactose group.

The invention also provides formulations that contain an agent to be delivered to a cell and a delivery enhancing compound. The concentration of the delivery enhancing compound in a formulation will depend on a number of factors such as the particular delivery enhancing compound being used, the buffer, pH, target tissue or organ and mode of administration. The concentration of the delivery enhancing compound will often be in the range of 1% to 50% (v/v), preferably 10% to 40% (v/v) and most preferably 15% to 30% (v/v). The delivery enhancing compounds of the invention are preferably used in the range of about 0.002 to 2 mg/ml, more preferably about 0.02 to 2 mg/ml, most preferably about 0.1 to 1 mg/ml in the formulations of the invention.

The delivery enhancing compounds of the invention are typically formulated in a solvent in which the compounds are soluble, although formulations in which the compounds are only partially solubilized are also suitable. Phosphate buffered saline (PBS) is one example of a suitable solubilizing agent for these compounds, and others are known to those of skill in the art. One will recognize that certain additional excipients and additives may be desirable to achieve solubility characteristics of these agents for various pharmaceutical formulations. For example, well known solubilizing agents such as detergents, fatty acid esters, surfactants can be added in appropriate concentrations so as to facilitate the solubilization of the compounds in the various solvents to be employed. Where the formulation includes a detergent, the detergent concentration in the final formulation administered to a patient is preferably about 0.5–2X the critical micellization concentration (CMC). Suitable detergents include those listed above. The identification of suitable detergents and appropriate concentrations for their use can be determined as described herein.

One example of a preferred solubilizing agent for compounds such as Syn3 and related compounds is Tween 80 at a concentration of approximately 0.05% to about 0.3%, more preferably at a concentration of about 0.10% to about 0.15%. Big CHAP is also a preferred solubilizing agent for Syn3 and related compounds.

The compounds of the invention may be used alone, in combination with each other, or in combination with another delivery-enhancing agent.

B. Modulatory Agents

The delivery-enhancing compounds of the invention are useful for enhancing the delivery of agents, including proteins, nucleic acids, antisense RNA, small molecules, and the like, to cells. For example, the delivery enhancing compounds are useful for delivering agents to cells that are part of any tissue or organ, including those that have an epithelial membrane.

Among the agents that are suitable for delivery using the delivery enhancing compounds are "modulatory agents," which, as used herein, refers to agents that can modulate biological processes. Such processes include, for example, cell growth, differentiation, proliferation (including neoplastic disorders such as cancer), regulation, metabolic or biosynthetic pathways, gene expression, and the like. Modulatory agents can also influence, for example, immune responses (including autoimmune disorders), infection by bacterial and fungal pathogens, and any other biological process that is regulatable by introduction of a modulatory agent.

Therapeutic agents are an example of modulatory agents that one can deliver using the delivery-enhancing agents. Such agents are useful for modulating cellular processes that are associated with disease. The term "therapeutic agent" as used herein includes but is not limited to therapeutic proteins, therapeutic genes, vectors (plasmid or viral vectors) containing a therapeutic gene, antisense nucleic acids, or other therapeutic nucleic acid sequences (e.g., triplex nucleic acids). For purposes of the present invention, the term "therapeutic gene," refers to a nucleic acid sequence introduced into a cell to achieve a therapeutic effect. Examples of such therapeutic genes include, but are not limited to, tumor suppressor genes, suicide genes, antisense nucleic acid molecules, triplex forming nucleic acid molecules, genes encoding cytokines (such as but not limited to the interferons α, β, δ, and γ), genes encoding interleukins (e.g., IL-1, IL-2, IL-4, IL-6, IL-7 and IL-10), and colony stimulating factors such as GM-CSF. In some instances, the therapeutic gene may present in a naturally occurring or recombinantly modified virus.

A suicide gene is a nucleic acid sequence, the expression of which renders the cell susceptible to killing by external factors or causes a toxic condition in the cell. A well known example of a suicide gene is the thymidine kinase (TK) gene (see, e.g., Woo et al., U.S. Pat. No. 5,631,236, issued May 20, 1997; Freeman et al., U.S. Pat. No. 5,601,818, issued Feb. 11, 1997) in which the cells expressing the TK gene product are susceptible to selective killing by the administration of gancyclovir.

Antisense nucleic acid molecules are complementary oligonucleotide strands of nucleic acids designed to bind to a specific sequence of nucleotides to inhibit production of proteins, including disease-causing proteins. Antisense molecules which bind to specific oncogenes are frequently used to inhibit the transcription of these cancer causing agents. These agents can be used alone or in combination with other therapeutic genes.

Triplex forming nucleic acids are molecules designed to inhibit transcription of genes, including, for example, disease causing genes. Generally, this is achieved by the triplex forming nucleic acid binding to the transcriptional control sequence of the target gene and preventing the transcription of the target gene. Triplex forming oligonucleotides recognize and bind to the major groove of double-stranded DNA by virtue of Hoogsteen hydrogen bonding. Examples of the use of triplex technology include targeting of the androgen receptor or the insulin-like growth factor genes with triplex technology in prostate cancer cells. Boulikas, T., *Anticancer Res.* 17(3A): 1471–1505 (1997). Triplex nucleic acids have been demonstrated to be mutagenic in some instances and such molecules may be used to induce responses of endogenous DNA repair mechanisms leading to an induction of tumor suppressor genes in a therapeutic manner and may contribute to genomic instability inducing apoptosis in the target cell. A variety of triplex nucleic compounds are currently under investigation and are well documented in the scientific literature.

"Tumor suppressor gene" refers to a gene which encodes a polypeptide that suppresses the formation of tumors. Tumor suppressor genes are naturally occurring genes in mammalian cells the deletion or inactivation of which is believed to be a necessary prerequisite for tumor development. Tumor suppressor gene therapy generally attempts to reintroduce the tumor suppressor gene to cells in which the gene is absent or inactive. Examples of tumor suppressor genes useful in the practice of the present invention include p53, p110Rb, members of the INK4 family of tumor suppressor genes including p16 and p21 and therapeutically effective fragments thereof such as p56Rb, p94Rb, etc. In the preferred practice of the invention, the tumor suppressor gene is selected from the Rb gene and the p53 gene and nucleic acid sequences encoding functional variants thereof, such as Rb56. In the most preferred practice of the invention, the tumor suppressor gene is p53.

In some embodiments, the compositions of the invention comprise a "therapeutically effective" amount of a therapeutic agent in a buffer comprising a delivery-enhancing compound. "Therapeutically effective" as used herein refers to the prevention of, reduction of, or curing of symptoms associated with a disease state.

The delivery-enhancing agents and formulations that contain these agents can also be used to facilitate delivery of genes of interest to cells, in particular cells of organs and tissues. These genes can encode, for example, proteins that are of interest for commercial purposes. As an example, one can use the agents and formulations to deliver to mammary tissue of a mammal a gene that encodes a nutritionally important protein which is then secreted in the milk produced by the mammal. Other uses of such agents and formulations will be evident to those of skill in the art.

The delivery enhancing agents and formulations that include such agents are also useful for delivering diagnostic agents to cells, organs and tissues. Examples of diagnostic agents include marker genes that encode proteins that are readily detectable when expressed in a cell (including, but not limited to, β-galactosidase, green fluorescent protein, luciferase, and the like) and labeled nucleic acid probes (e.g., radiolabeled probes).

C. Vectors for Gene Delivery

In the situation where an agent to be delivered to a cell is a gene, one can incorporate the gene into a vector. Examples of vectors used for such purposes include expression plasmids capable of directing the expression of the gene of interest in the target cell. In other instances, the vector is a viral vector system wherein the gene of interest is incorporated into a viral genome capable of transfecting the target cell. Where the gene of interest is designed for expression in a target cell, the gene can be operably linked to expression and control sequences that can direct expression of the gene in the desired target host cells. Thus, one can achieve expression of the gene under appropriate conditions in the target cell.

Viral vector systems useful in the practice of the instant invention include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, genes of interest are inserted into such vectors to allow packaging of the gene construct, typically with accompanying viral DNA, infection of a sensitive host cell, and expression of the gene of interest. A preferred recombinant viral vector is the adenoviral vector delivery system which has a deletion of the protein IX gene (see, International Patent Application WO 95/11984, which is herein incorporated by reference in its entirety for all purposes).

"Recombinant" as used herein refers to nucleic acids and the proteins encoded by them wherein the nucleic acids are constructed by methods of recombinant DNA technology, also termed "genetic engineering."

Therapeutically effective amounts of the pharmaceutical composition comprising a modulatory gene, such as a p53 gene or a retinoblastoma tumor suppressor gene, in a recombinant viral vector delivery system formulated in a buffer comprising a delivery-enhancing agent, will be administered in accord with the teaching of this invention. For example, therapeutically effective amounts of a therapeutic gene in the recombinant adenoviral vector delivery system formulated in a buffer containing a delivery-enhancing agent are in the range of about $1\times10^8$, particles/ml to $1\times10^{12}$ particles/ml, more typically about $1\times10^8$ particles/ml to $5\times10^{11}$ particles/ml, most typically $1\times10^9$ particles/ml to $1\times10^{11}$ particles/ml (PN/ml).

D. Gene Delivery Systems

As used herein, "gene delivery system" refers to any means for the delivery of an agent to a target cell. The agent can be associated with a gene delivery system which is then delivered to the cell using a formulation that contains a delivery enhancing compound.

In some embodiments of the invention, gene constructs or other agents are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621–14624 (1988); WO 92/06180). For example, gene constructs can be linked through a polylysine moiety to asialo-oromucocid, which is a ligand for the asialoglycoprotein receptor of hepatocytes.

Similarly, viral envelopes used for packaging gene constructs can be modified by the addition of receptor ligands or antibodies specific for a receptor to permit receptor-mediated endocytosis into specific cells (see, e.g., WO 93/20221, WO 93/14188, WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88: 8850–8854 (1991)). In other embodiments, molecular conjugates of the instant invention can include microtubule inhibitors (WO/9406922); synthetic peptides mimicking influenza virus hemagglutinin (Plank et al., *J. Biol. Chem.* 269:12918–12924 (1994)); and nuclear localization signals such as SV40 T antigen (WO93/19768).

In some embodiments of the invention, the modulating agent is an antisense nucleic acid. The antisense nucleic acid can be provided as an antisense oligonucleotide (see, e.g., Murayama et al., *Antisense Nucleic Acid Drug Dev.* 7:109–114 (1997)). Genes encoding an antisense nucleic acid can also be provided; such genes can be formulated with a delivery enhancing compound and introduced into cells by methods known to those of skill in the art. For example, one can introduce a gene that encodes an antisense nucleic acid in a viral vector, such as, for example, in hepatitis B virus (see, e.g., Ji et al., *J. Viral Hepat.* 4:167–173 (1997)); in adeno-associated virus (see, e.g., Xiao et al., *Brain Res.* 756:76–83 (1997));

or in other systems including, but not limited, to an HVJ (Sendai virus)-liposome gene delivery system (see, e.g., Kaneda et al., *Ann. N.Y. Acad. Sci.* 811:299–308 (1997)); a "peptide vector" (see, e.g., Vidal et al., *CR Acad. Sci III* 32:279–287 (1997)); as a gene in an episomal or plasmid vector (see, e.g., Cooper et al., *Proc. Natl. Acad. Sci. U.S.A.* 94:6450–6455 (1997), Yew et al. *Hum Gene Ther.* 8:575–584 (1997)); as a gene in a peptide-DNA aggregate (see, e.g., Niidome et al., *J. Biol. Chem.* 272:15307–15312 (1997)); as "naked DNA" (see, e.g., U.S. Pat. No. 5,580,859 and U.S. Pat. No. 5,589,466); in lipidic vector systems (see, e.g., Lee et al., *Crit Rev Ther Drug Carrier Syst.* 14:173–206 (1997)); polymer coated liposomes (Marin et al., U.S. Pat. No. 5,213,804, issued May 25, 1993; Woodle et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334,761, issued Aug. 2, 1994); gas filled microspheres (Unger et al., U.S. Pat. No. 5,542,935, issued Aug. 6, 1996), ligand-targeted encapsulated macromolecules (Low et al. U.S. Pat. No. 5,108,921, issued Apr. 28, 1992; Curiel et al., U.S. Pat. No. 5,521,291, issued May 28, 1996; Groman et al., U.S. Pat. No. 5,554,386, issued Sep. 10, 1996; Wu et al., U.S. Pat. No. 5,166,320, issued Nov. 24, 1992).

E. Pharmaceutical Formulations

When used for pharmaceutical purposes, the formulations of the invention include a buffer that contains the delivery-enhancing compound. The buffer can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. (1966) *Biochemistry* 5:467. The pH of the buffer in the pharmaceutical composition comprising a modulatory gene contained in an adenoviral vector delivery system, for example, is typically in the range of 6.4 to 8.4, preferably 7 to 7.5, and most preferably 7.2 to 7.4.

The compositions of this invention can additionally include a stabilizer, enhancer or other pharmaceutically acceptable carriers or vehicles. A pharmaceutically acceptable carrier can contain a physiologically acceptable compound that acts, for example, to stabilize the recombinant adenoviral vector delivery system comprising the tumor suppressor gene. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier depends on the route of administration and the particular physio-chemical characteristics of the recombinant adenoviral vector delivery system and the particular tumor suppressor gene contained therein. Examples of carriers, stabilizers or adjuvants can be found in Martin, *Remington's Pharm. Sci.*, 15th Ed. (Mack Publ. Co., Easton, Pa. 1975), which is incorporated herein by reference.

F. Administration of Formulations

In some embodiments, the delivery-enhancing compound is included in the buffer in which the modulating agent is formulated. The delivery-enhancing compound can be administered prior to the modulating agent or concomitant with the modulating agent. In some embodiments, the delivery-enhancing compound is provided with the modulating agent by mixing a modulating agent preparation with a delivery-enhancing compound formulation just prior to administration to the patient. In other embodiments, the delivery-enhancing compound and modulating agent are provided in a single vial to the caregiver for administration.

In the case of a pharmaceutical composition comprising a tumor suppressor gene contained in a recombinant adenoviral vector delivery system formulated in a buffer which further comprises a delivery-enhancing agent, the pharmaceutical composition can be administered over time in the range of about 5 minutes to 3 hours, preferably about 10 minutes to 120 minutes, and most preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and most preferably about 1 minute to 5 minutes prior to administration of the adenoviral vector delivery system containing the tumor suppressor gene.

The modulating agent formulated in a buffer comprising a delivery-enhancing agent can be delivered to any tissue or organ, including neoplastic tissues such as cancer tissue, using any delivery method known to the ordinarily skilled artisan for example, intratumoral or intravesical administration. Tissues and organs include any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

In some embodiments of the invention, the therapeutic agent is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701. Such formulations are especially useful for the treatment of cancers of the mouth, head and neck cancers (e.g., cancers of the tracheobronchial epithelium) skin cancers (e.g., melanoma, basal and squamous cell carcinomas), cancers of the intestinal mucosa, vaginal mucosa, and cervical cancer.

In some embodiments of the invention, a therapeutic agent is formulated in ophthalmic formulations for administration to the eye. Such formulations are useful in the delivery of the retinoblastoma (RB) gene to the eye, optionally in conjunction with the delivery of p53.

G. Methods of Treatment

The formulations of the invention are typically administered to enhance transfer of an agent to a cell. The cell can be provided as part of a tissue, such as an epithelial membrane, or as an isolated cell, such as in tissue culture. The cell can be provided in vivo, ex vivo, or in vitro.

The formulations containing delivery enhancing compounds and modulating agents can be introduced into the tissue of interest in vivo or ex vivo by a variety of methods. In some embodiments of the invention, the modulating agent is introduced to cells by such methods as microinjection, calcium phosphate precipitation, liposome fusion, or biolistics. In further embodiments, the therapeutic agent is taken up directly by the tissue of interest.

In some embodiments of the invention, the compositions of the invention are administered ex vivo to cells or tissues explanted from a patient, then returned to the patient. Examples of ex vivo administration of therapeutic gene constructs include Arteaga et al., *Cancer Research* 56(5):1098–1103 (1996); Nolta et al., *Proc Natl. Acad. Sci. USA* 93(6):2414–9 (1996); Koc et al., *Seminars in Oncology* 23(1):46–65 (1996); Raper et al., *Annals of Surgery* 223(2):116–26 (1996); Dalesandro et al., *J. Thorac. Cardi. Surg.*, 11(2):416–22 (1996); and Makarov et al., *Proc. Natl. Acad. Sci. USA* 93(1):402–6 (1996).

EXAMPLES

The following examples are intended to illustrate, not limit the scope of this invention. In the following examples, "g" means grams, "ml" means milliliters, "mol" means moles, "° C." means degrees Centigrade, "min." means minutes, "DMF" means dimethylformamide, and "PN" specifies particle number. All temperatures are in degrees Centigrade unless otherwise specified.

Example 1

Ethanol Improves Gene Transfer in the Bladder

Initial experiments have shown that several factors including virus concentration, time of administration, and volume of dosing can influence gene transfer to the bladder epithelium after intravesical administration to rats. Because increased penetration of dyes can be achieved by intravesical administration of different solvents, modification of the adenovirus formulation was also investigated as an alternative strategy to increase adenovirus transgene expression in the bladder (Monson et al., *Urology* 145:842–845 (1991)). The instant experiments focused on the use of ethanol to increase adenovirus transgene expression in the bladder.

Nine female buffalo rats (Harlan Sprague Dawley) were anesthetized with isoflurane and received a single intravesical administration of a human recombinant adenovirus encoding the lacZ gene (rAd-βgal). The human recombinant adenoviral vector comprising the lacZ gene (rAd-βgal) is described in Wills et al., *Human Gene Therapy* 5:1079–1088 (1994). Before installation bladders were flushed with PBS and emptied. rAd-βgal was then diluted to achieve a final concentration of $1.7 \times 10^{11}$ PN/mL in 1) VPBS (2% (w/v) sucrose and 2 mM MgCl, in PBS), 2) 30% (v/v) ethanol, or 3) 50% (v/v) DMSO, and instilled in a 250 μL volume (N=3 animals/group). The administered material was retained in the bladder for 45 minutes. The bladder were then flushed with PBS, and the animals were permitted to recover from the procedure. Two days after administration, rats were sacrificed, bladders were harvested, fixed, and whole organs were stained with an Xgal (5-Bromo-4-chloro-3-indolyl-β-D-galactoside) solution to evaluate reporter gene transfer. Xgal-stained tissues were then paraffin embedded, sectioned, and counter stained with hematoxylin and eosin. Hydrolysis of Xgal by β-galactosidase results in a blue color that localized to the superficial luminal bladder epithelium.

Transgene expression, consequent to delivery by the adenoviral vector, was detected in bladders from all animals treated with rAd-βgal but not in an untreated control. Transgene expression was similar to previously published results using the PBS/sucrose formulation (Bass et al., *Cancer Gene Therapy* 2:2:97–104 (1995)). In sharp contrast, β-galactosidase expression in the luminal epithelial surface was greatly enhanced in animals that received rAd-βgal diluted in 30% ethanol (FIG. 1). Bladder specimens described in FIG. 1 were embedded, sectioned, and counterstained with hematoxylin and eosin. Histologic evaluation of the bladder tissue demonstrated increased β-galactosidase expression of the transitional bladder epithelium when ethanol was added to the adenovirus formulation (FIG. 2). The interaction of ethanol with the protective glycosaminoglycan (GAG) layer on the epithelium surface provides a mechanism for the observed increase in transgene expression. Disruption of this layer may facilitate virus-cell interaction at the surface and potentially enhance penetration into the submucosa.

Example 2

Dose-Dependent Transgene Expression in the Rat Bladder

Figure 3:
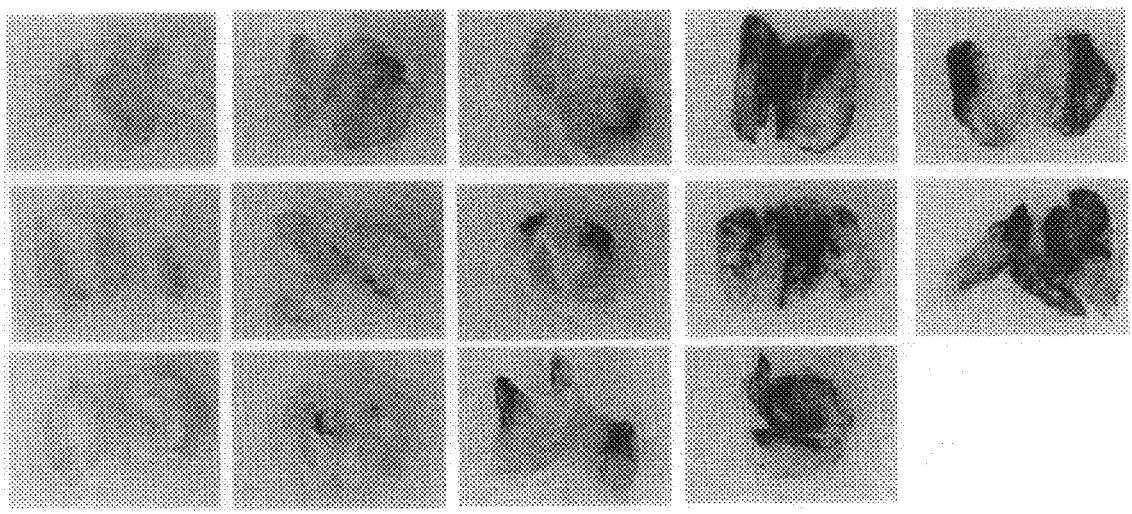
FIG. 3 depicts dose dependent adenovirus transgene expression in the rat bladder after intravesical administration.

In another experiment, 18 female Sprague-Dawley rats were anaesthetized with isoflurane and received a single 0.5 ml intravesical bolus of rAd-βgal at concentrations of $2 \times 10^7$, $2 \times 10^8$, $2 \times 10^9$, $2 \times 10^{10}$, and $2 \times 10^{11}$, PN/mL in a 22.5% (v/v) ethanol formulation. After a 45 minute incubation, the bladders were flushed with PBS, and animals were permitted to recover from anesthesia. Two days later, animals were sacrificed, and bladders were harvested, fixed, and whole organs were stained with Xgal solution to evaluate adenovirus transgene expression. β-galactosidase expression in the luminal bladder epithelium correlated with the concentration of the administered recombinant adenovirus (FIG. 3). No striking differences were observed among animals receiving $2 \times 10^{10}$ or $2 \times 10^{11}$ PN/mL, suggesting a saturation of transgene expression in this model. Analysis of the volume voided after instillation indicated only a minimal reduction in the infectious titer of the dosing material at these high doses. Expression of β-galactosidase decreased at lower concentrations. No evidence of β-galactosidase expression was detected in animals dosed at a concentration of $1 \times 10^7$ PN/mL or in an untreated control animal.

Example 3

ACNRB Gene Transfer in the Mouse Bladder

A pilot study was conducted to specifically evaluate expression of the RB transgene using a RT-PCR assay. The recombinant adenovirus used in this study was based on serotype 5 human adenovirus from which the viral early region 1 encoding E1a, E1b, and pIX proteins have been deleted. This adenovirus is limited to propagation in 293 cells which produce the Ad5 E1 gene products required for replication. Transfer plasmids encoding either full length or truncated Rb were generated from pACN (Wills et al., *Cancer Gene Therapy* 2:191–197 (1995)) and were, in turn, used to construct the recombinant adenoviruses. Either a full-length RB cDNA (1–928 amino acids), subcloned as a 2.8 Kb Xba I—Bam HI fragment from the plasmids pETRbc (Huang et al., *Nature* 350:160–162 (1991) or a truncated fragment (amino acids 381–928), subcloned as a 1.7 KB Xba I—Bam HI cDNA fragment, was placed downstream of the CMV promoter/enhancer and the Ad 2 tripartite leader cDNA of the plasmid pACN. These plasmids were subsequently linearized with Eco RI and cotransfected (CaPO$_4$, Stratagene) with either the isolated Cla I digested large fragment of H5ilE4 (Hemstrom et al., *J. Virol.* 62:3258–3264 (1988)), to make Ad-RB56 (ACN56) containing a partial E4 deletion, or with the large fragment from a hybrid virus of dl327 (Ginsberg et al. *Proc. Natl. Acad. Sci. U.S.A.* 86:3823–3827 (1989)) and H5ilE4 to create Ad-Rb110 (ACNRB) which contains deletions in both the E3 and E4 regions of the vector.

Figure 4:
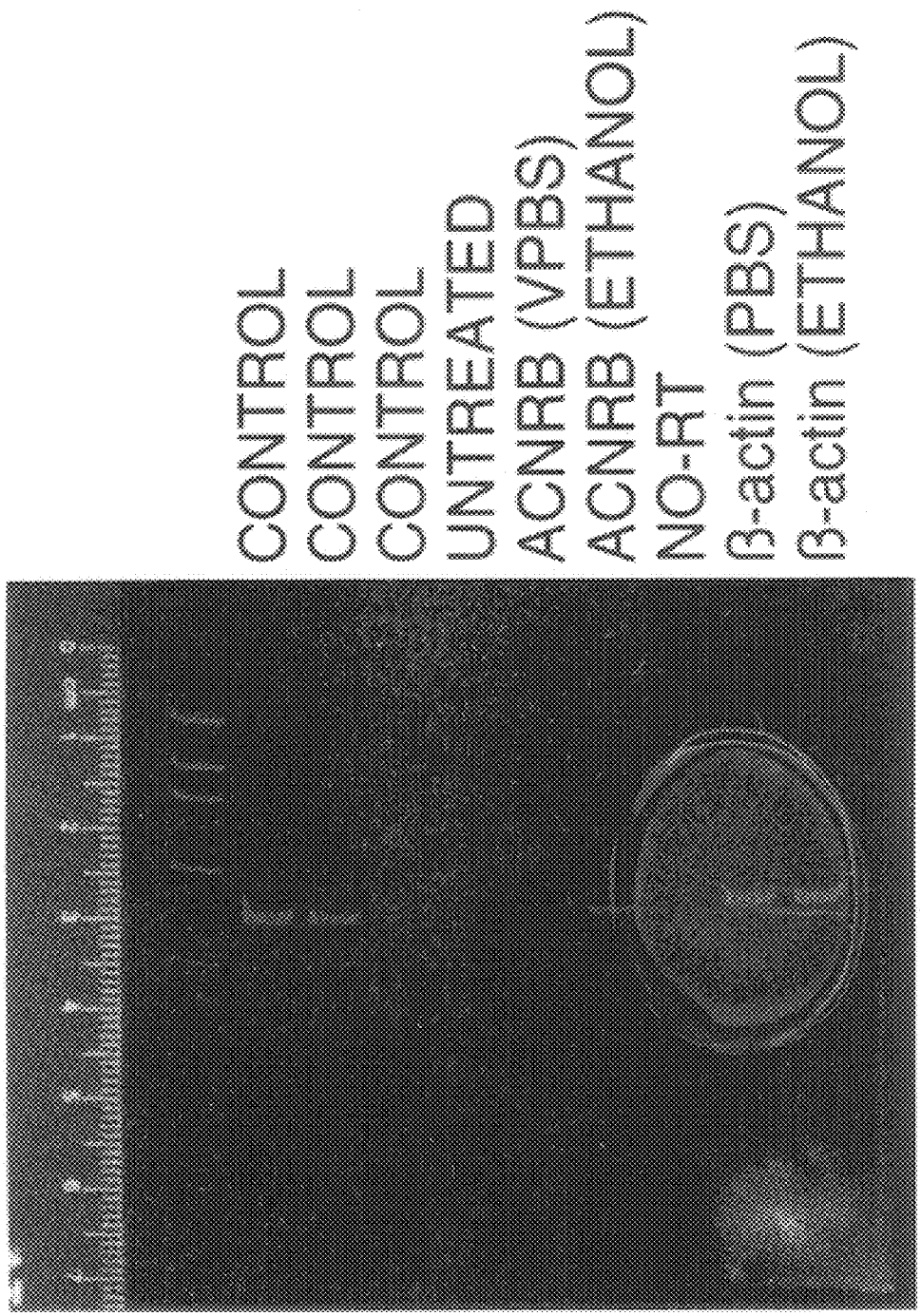
FIG. 4 depicts a reverse-transcriptase polymerase chain reaction (RT-PCR) analysis of recombinant adenovirus transgene expression in the mouse bladder after intravesical administration.

Eight female ICR mice (Charles River Laboratories) were anesthetized with avertine and each received a single 80 μl intravesical administration of (ACNRB). ACNRB ($4 \times 10^{11}$ PN/mL) was diluted and prepared in a PBS solution or a 30% (v/v) ethanol solution. After the virus was retained in the bladder for 45 minutes, the animals were permitted to recover and void. Mice were sacrificed 2 days or 14 days after ACNRB administration, and bladders, livers, and kidneys from each animal were harvested, homogenized, and processed for analysis (N=2 animals/group). Transgene expression was determined using RT-PCR with a primer specific for ACNRB. More specifically, primers were generated to identify ACNRB and amplify the region from the 3' end of the CMV sequence and to the 5' end of the RB sequence. Following amplification (30 cycles) RT-PCR products were separated on a 10% polyacrylamide gel, stained with ethidium bromide, and photographed. Increased ACNRB expression was detected after treatment with ACNRB in 30% (v/v) ethanol compared to very low expression after treatment with ACNRB in VPBS. Positive controls for the assay included samples from ACNRB-infected 5637 human bladder cancer cells (CONTROL). Bladder RNA samples from ACNRB-infected animals that were amplified with primers specific for beta-actin provided an internal control for the quality of RNA. Untreated samples and bladder samples without the reverse transcriptase (RT) provided controls for contaminating DNA. Two days after dosing, levels of ACNRB expression in the bladder homogenates were detected from animals that received ACNRB prepared in 30% ethanol (FIG. 4). No evidence of expression was detected in non-bladder tissue or in any samples collected 14 days after dosing.

Example 4

Kinetics of Biodistribution and ACNRB Expression After Intravesical Administration to Mice To investigate the time course of expression after intravesical administration, 40 female mice (Charles River Laboratories) were anaesthetized with avertine and received a single 80 μL bolus of ACNRB ($4 \times 10^{10}$ PN/mL in 22% (v/v) ethanol). The instilled material was retained in the bladder for approximately 45 minutes, and animals were permitted to recover from the procedure. Mice were sacrificed 1, 2, 3, 4, 5, 6, 7, and 14 days after administration (N=4/time) for analysis. Bladders, livers, and kidneys were harvested and snap frozen in liquid nitrogen for subsequent analysis. For detection of ACNRB expression, tissue samples were homogenized, and total RNA was extracted using TRI-Reagent®. An aliquot of total RNA was amplified in an RT-PCR assay using primers specific for ACNRB to distinguish transgene expression from endogenous RB expression. For detection of ACNRB DNA, a DNA extraction kit (Stratagene) was used on tissue homogenates. PCR was performed with the primers specific for ACNRB, as described above for the RT-PCR analysis.

Figures 5A, 5B, 5C:
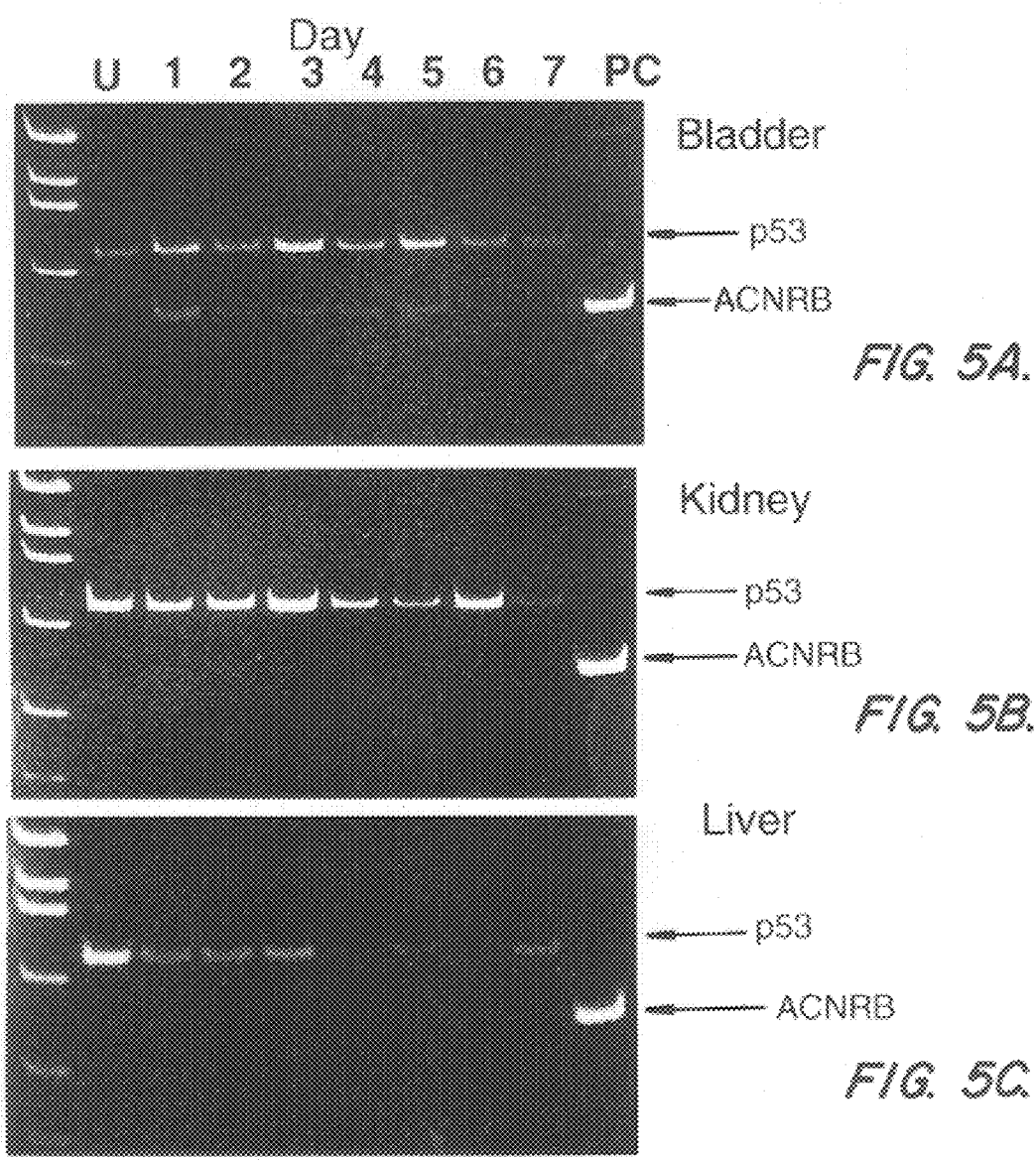
FIG. 5 depicts a time course of recombinant adenovirus transgene expression in bladder, kidney, and liver tissue after intravesical administration of the virus.

ACNRB transgene expression in the bladder homogenates was detected only in samples collected on days 1–6, with expression relative to endogenous p53 decreasing with time (FIG. 5, upper panel). No expression was detected from samples collected 7 and 14 days after administration. Interestingly, some ACNRB expression was detected in the kidneys on days 1, 2 and 3, but no expression was observed in the liver (FIG. 5, lower panels).

Figure 6A:
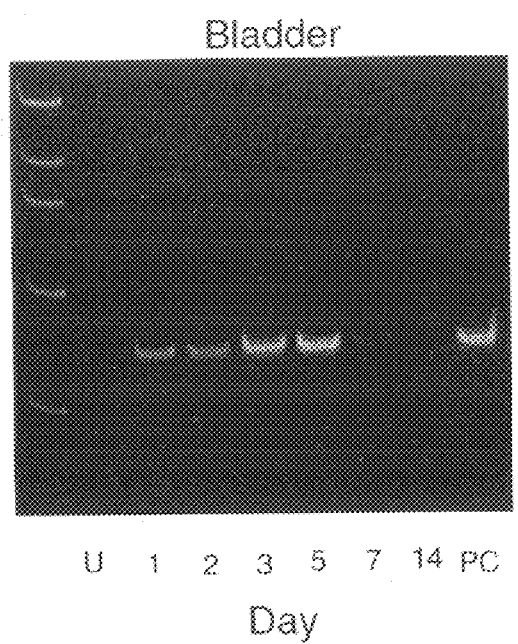
FIG. 6 depicts recombinant adenovirus transgene DNA in bladder and kidney homogenates after intravesical administration.
Figure 6B:
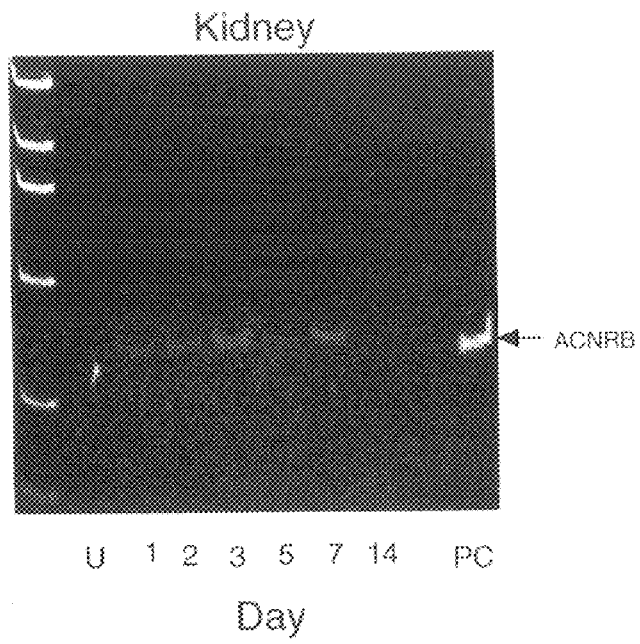

ACNRB DNA was detected in bladder tissue of all animals that received ACNRB, including those harvested 14 days after administration (FIG. 6, (left panel)). DNA was also recovered from the kidney homogenates, consistent with the ACNRB expression detected in this tissue (FIG. 6, right panel). No evidence for ACNRB DNA was detected in liver samples harvested during the study (data not shown). Samples from an untreated animal (U) and purified ACNRB DNA (PC) were used as negative and 25 positive controls, respectively.

Because systemic administration of recombinant adenovirus results primarily in transgene expression in the liver (Li et al., *Human Gene Therapy* 4:403–409 (1993)), the absence of ACNRB DNA and expression in liver samples (FIG. 5 and FIG. 6) suggests negligible systemic exposure of ACNRB after intravesical administration. Retrograde flow via the ureters may have contributed to the detection of ACNRB in the kidney.

The data presented above demonstrate transgene expression in the rodent bladder following intravesical administration of ACNRB. These studies further indicate that adenovirus-mediated gene transfer to the bladder epithelium can be enhanced by the presence of a delivery-enhancing agent, such as ethanol, in the formulation. One mechanism for the increased gene transfer may be the disruption of the protective glycosaminoglycan layer on the epithelial surface of the bladder. A single intravesical administration of ACNRB in a 20–30% (v/v) ethanol formulation results in transgene expression in the bladder that persists for. approximately one week. Retrograde ureteral flow provides a likely explanation for the transient expression of ACNRB detected in the kidney. The absence of ACNRB expression and ACNRB DNA in the liver indicates limited systemic exposure after intravesical administration.

Example 5

Use of Detergent Formulations

To minimize side effects without losing gene transfer efficiency, other excipients were tested. Detergents are known to interact with cell membranes and form large pores without further damaging the cells. The efficiency of recombinant adenovirus formulated in less toxic detergents was studied in rats and mice gene transfer models.

rAd-βgal was formulated in different detergents at their critical micellization concentration to evaluate efficiency of gene transfer to the bladder epithelium. Female rats (about 200 g b/w, Harlan Sprague Dawley) were anesthetized with isoflurane and received a single intravesical administration of rAd-βgal (1×10¹¹ PN/ml) in different detergent formulations (see Table I). Before instillation, bladders were flushed with PBS and then emptied. rAd-βgal was then instilled in a volume of 0.5 ml. The instilled solution was retained in the bladder for 45 minutes. The bladders were then flushed with PBS, and the animals were permitted to recover from the procedure. 48 hours after administration, the rats were sacrificed, the bladders harvested, and fixed in formalin. After fixation, the bladders were opened longitudinally so that the urothelium was exposed to the chromogen (Xgal), that is converted to a blue color, if reporter gene (β-galactosidase) expression is present. The luminal epithelial surface of the whole bladder was photographed an blue staining scored: + (minimal staining), ++ (moderate staining), +++ intense staining covering the whole bladder epithelial surface. The results are shown in Table I. Some of the anionic detergents (taurodeoxycholate), zwitterionic detergents (CHAPS, ZWITTERGENT®), and non-ionic detergents (Big CHAP (CALBIOCHEM®), TRITON® X-100) enhanced gene transfer dramatically. Cationic detergents and some of the nonionic detergents (PLURONIC®D F68, TWEEN®), did not have similar effects. Improvements of gene transfer were often accompanied by cystitis. Zwitterionic detergents facilitated bladder stone formation.

Possible manifestations of cystitis as observed with ethanol were evaluated in mice using a 7 mM Big CHAP (CALBIOCHEM®) (2X CMC) or 0.05 mM TRITON®-X-100 detergent (CMC) formulation. The formulations were administered intravesically in a volume of 80 uL, and animals were observed over a 7-day interval. After sacrifice, bladders were paraffin-embedded, sectioned, and stained with hematoxylin and eosin for pathologic evaluation. Only a slight macrophage infiltration into the bladder tissue was observed in mice treated with Big CHAP (CALBIOCHEM®). Macrophages infiltrated more prominently (slight to mild) induced by TRITON®-X-100 detergent. In sharp contrast, significant cystitis was detected in animals treated with 22% ethanol.

Example 6

Gene Transfer of ACNRB

Figure 9:
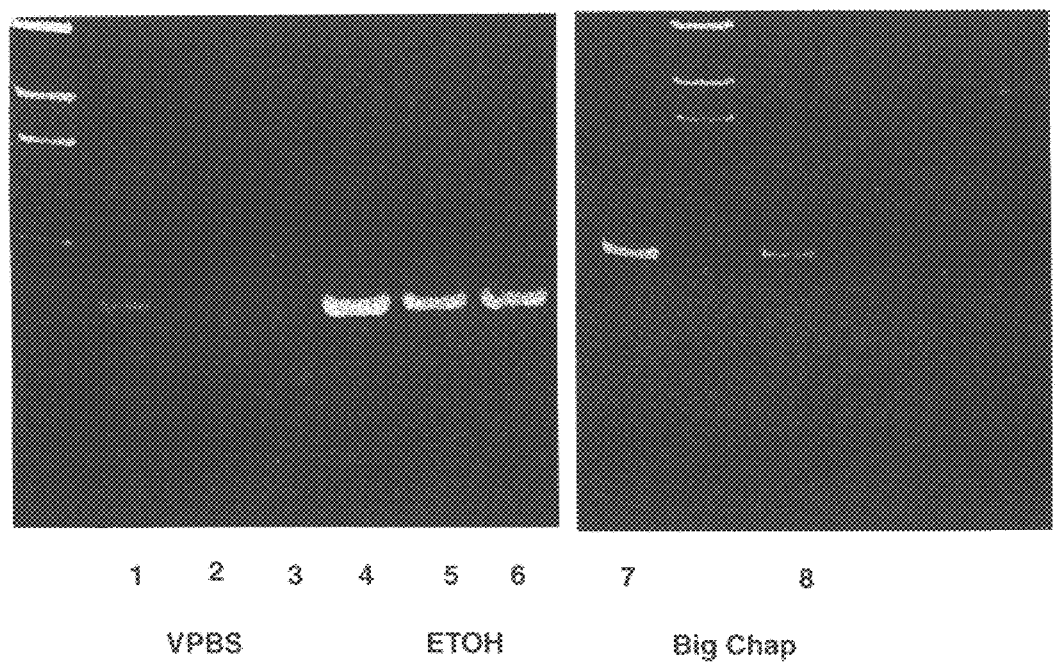
FIG. 9 depicts enhancement of recombinant adenovirus transgene expression in bladder tissue by using an ethanol (ETOH) or Big CHAP formulation.

In addition to the experiments with the reporter gene, a different set of studies was conducted to specifically evaluate gene transfer of ACNRB. Female ICR mice were anesthetized with avertine and each mouse received a single 80 μL intravesical administration of ACNRB. ACNRB (4×10¹⁰ PN/mL) was formulated in VPBS, 22% (v/v) ethanol, or 3 mM Big CHAP (CALBIOCHEM®). After the virus was retained in the bladder for 45 minutes, the animals were permitted to recover. Mice were sacrificed 48 hours after ACNRB administration, and bladders snap frozen in liquid nitrogen. Transgene expression was determined using RT-PCR. Tissues were rinsed in RNAse free water, homogenized, digested in Tri-Reagent (Molecular Research Center), and total cellular RNA extracted. ACNRB was probed using a 5' primer located in the CMV region of ACNRB vector, and a 3' primer resided in the 5' end of Rb genome. RT-PCR was performed in the Perkin Elmer 9600 GeneAmp PCR System. Cycling conditions were 10 min at 65° C., 8 min at 50° C., 5 min at 95° C. 32 cycles of PCR were performed, each cycle consisting of 30 sec at 94° C., 30 sec at 58° C., and 30 sec at 72° C. The 32nd cycle included a 10 min elongation step at 72° C. to ensure full extension of incomplete DNA fragments. ACNRB-RNA bands were stained with ethidium bromide. The results, enhanced expression using an ethanol or Big CHAP (CALBIOCHEM®) formulation, are shown in FIG. 9.

Example 7

Big CHAP (CALBIOCHEM®) Enhances Transgene Expression with Minimal Cystitis

Figure 7:
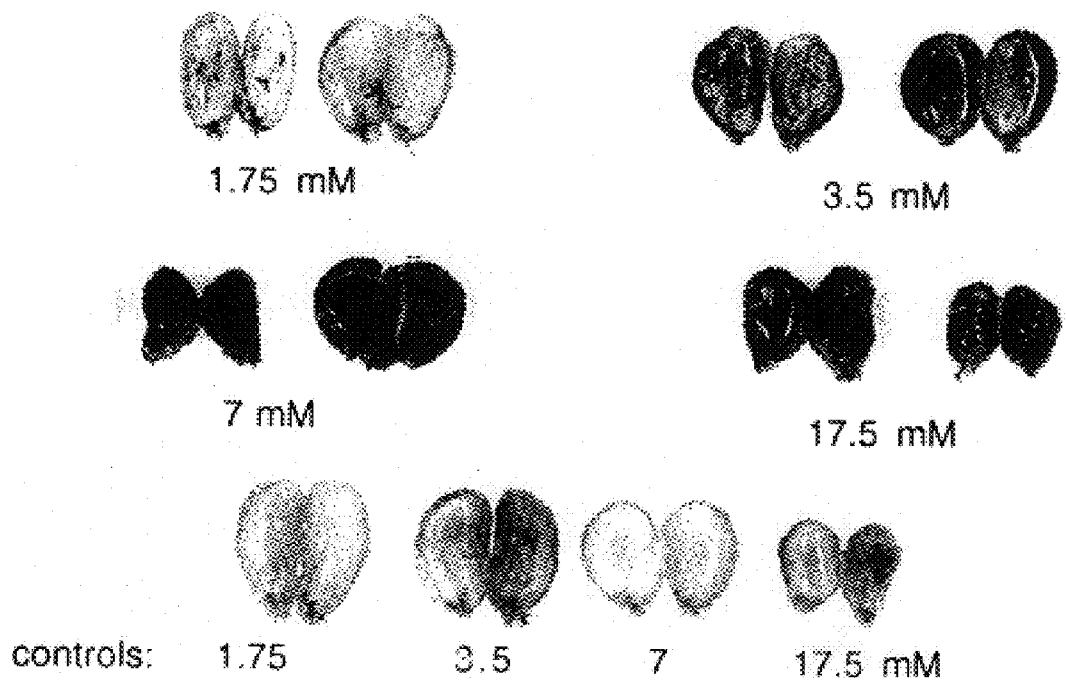
FIG. 7 depicts improvement of gene transfer to bladder epithelium using a Big CHAP (N,N,bis-(3-D-gluconamidopropyl)-cholamide (CALBIOCHEM® Biochemicals, San Diego, Calif.) formulation.

Because Big CHAP (CALBIOCHEM®) enhanced gene transfer with minimal cystitis, this formulation was selected for further evaluation, including concentration and dose-dependence in studies similar to those described above. Briefly, in anaesthetized female rats rAd-βgal (1×10¹¹ PN/ml) was administered into the bladder via an intravesical catheter. rAd-βgal was formulated in different concentrations of Big CHAP (CALBIOCHEM®). A volume of 0.5 ml was injected and remained instilled in the bladder for 45 minutes. The animals were sacrificed 48 hours later, the bladder fixed in 4% formalin/glutaraldehyde, opened longitudinally, and the β-galactosidase enzyme activity measured using Xgal substrate. The intensity of blue staining correlates with the βgal-transgene expression. FIG. 7 shows the epithelial surface of Xgal stained bladders. The results indicate a concentration-dependent increase of gene transfer to the epithelium. The 3.5–7 mM concentrations of Big CHAP (CALBIOCHEM®) significantly improved gene transfer. The formulation alone (FIG. 7, lower panel) did not induce a blue color from the Xgal substrate. A higher concentration (17.5) mM did not notably improve gene transfer or expression, but induced cystitis in some of the animals tested.

TABLE I

| Excipient | Charge of Detergent | Dose (mM) | Gene Expression in Bladder Epithelium | Gross Pathology | Stability |
|---|---|---|---|---|---|
| Taurocholate | anionic | 6 | + | none | ND |
| Deoxycholate | anionic | 5 | + | Cystitis | ND |
| Taurodeoxycholate | anionic | 6 | +++ | Cystitis | + |
| Cetylpyridinium | cationic | 0.9 | + | none | − |
| Benzalkonium Chloride | cationic | 0.5% | <+ | none | − |
| Zwittergent ® 3-14 | zwitterionic | 4 | +++ | stone formation | ND |
| Chaps | zwitterionic | 7 | +++ | stone formation | + |
| Big CHAP (CALBIOCHEM ®) | non ionic | 3.5 | +++ | none | + |
| Deoxy Big CHAP (CALBIOCHEM ®) | non ionic | 1.5 | +++ | Cystitis | ND |
| Triton X-100 | non ionic | 0.05 | +++ | none | + |
| C12E8 | non ionic | 4 | ++ | none | ND |
| Octyl-β-D-Glucopyranoside | non ionic | 10 | ++ | none | ND |

TABLE I-continued

| Excipient | Charge of Detergent | Dose (mM) | Gene Expression in Bladder Epithelium | Gross Pathology | Stability |
|---|---|---|---|---|---|
| Pluronic F68 | non ionic | 0.04 | + | none | + |
| Tween 20 | non ionic | 2 | + | none | + |
| Tween 80 | non ionic | 0.02 | + | none | ND |
| Tween 80 | non ionic | 2 | + | none | + |

Figure 8:
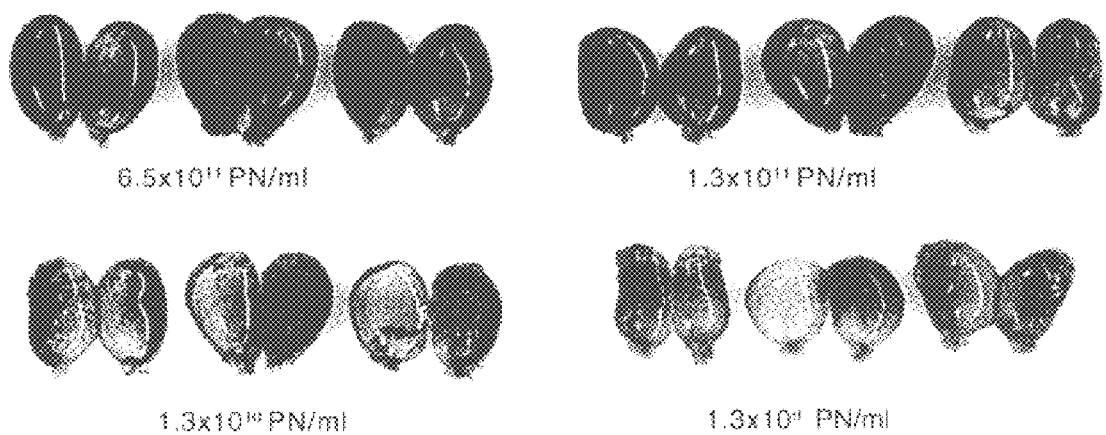
FIG. 8 depicts improvement of gene transfer to bladder epithelium using different concentrations of recombinant adenovirus in a 7 mM Big CHAP formulation.

Effects of higher recombinant adenovirus concentrations were also tested. Briefly, in anaesthetized female rats different concentrations of rAd-βgal, formulated in 7 mM Big CHAP (CALBIOCHEM®) were administered into the bladder via an intravesical catheter. The animals were sacrificed 48 hours later, the bladder fixed in 4% formalin/glutaraldehyde, opened longitudinally, and Xgal stained. FIG. 8 shows a concentration dependent increase of gene transfer to the epithelium. A concentration of $1.3 \times 10^{11}$ PN/ml induced maximal gene transfer. A higher concentration ($6.5 \times 10^{11}$ PN/ml) did not notably improve the blue staining. In lower concentrations of rAd-βgal, $1.3 \times 10^{10}$ PN/ml, or $1.3 \times 10^{9}$ PN/ml, transgene expression reduced dose dependently. When 3.5 mM and 7 mM formulations were compared, β-galactosidase expression was similar, although the enhanced effect appeared more reproducible in animals treated with the 7 mM Big CHAP (CALBIOCHEM®) formulation.

Example 8

Transgene Expression in Tumors with Big CHAP (CALBIOCHEM®D) Formulation

Figure 10:
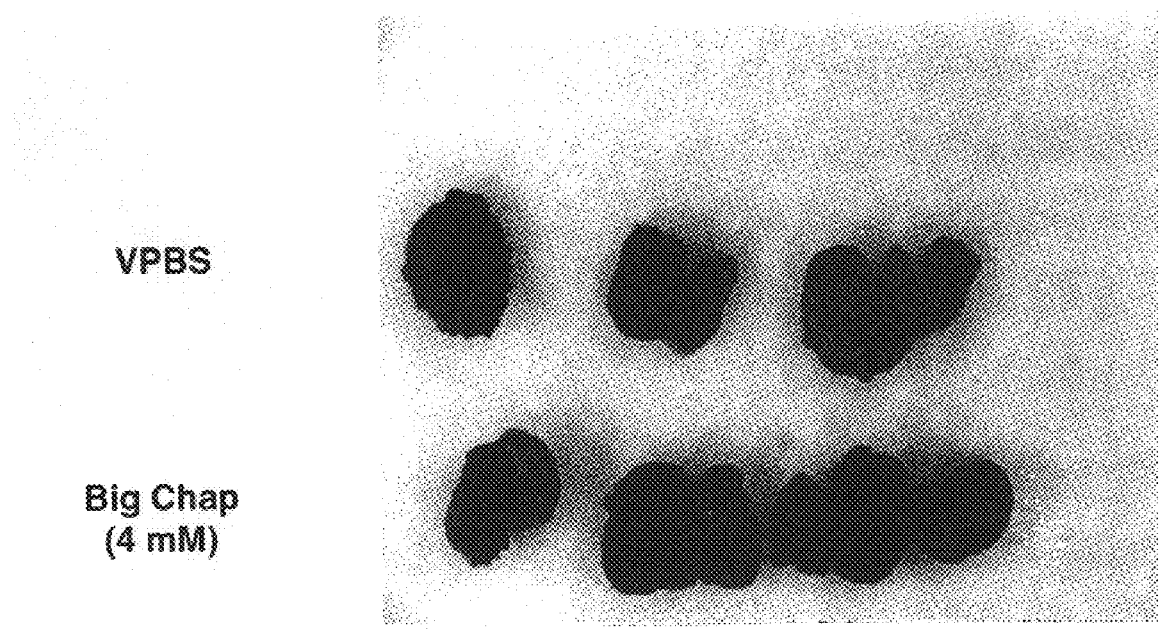
FIG. 10 depicts gene transfer to tumors using a 4 mM Big CHAP formulation.

Because initial investigations focused on animals with intact bladder epithelium, evaluated adenovirus mediated gene transfer in an animal model of transitional cell carcinoma was also studied. Tumors were induced in male Fisher rats by addition of 0.05% BBN in the drinking water for six months. rAd-βgal ($1 \times 10^{11}$ PN/ml), formulated in 4 mM Big CHAP (CALBIOCHEM®) or VPBS was instilled into the bladder for 45 minutes by direct injection. β-gal expression was evaluated 48 hr after treatment. Consistent with earlier experiments using non-tumor bearing animals, gene transfer to tumor tissue was improved with the Big CHAP (CALBIOCHEM®) formulation compared to the VPBS formulation (FIG. 10).

Gene transfer of rAd carrying the p53 gene (rAd-p53) (Wills et al., Human Gene Therapy 5:1079–1088 (1994)) was also tested in this animal model of bladder cancer. Briefly, bladder tumors were induced in female Fisher rates (Charles River) by addition of 0.05% BBN (N-butyl-N-N (4-hydroxybutyl)nitrosamine) in the drinking water for three months. rAd-p53 ($1 \times 10^{11}$ PN/ml) was formulated in 7 mM Big CHAP (CALBIOCHEM®). Under isoflurane anesthesia a catheter (24 G) was inserted into the bladder for administration. rAd-p53 was instilled into the bladder for 45 minutes. The animals were then allowed to recover from anesthesia. Twenty-four hours later, animals were sacrificed, and the bladder was fixed in formalin. After paraffin embedding and sectioning, p53 expression was assayed by immunohistochemistry using p53ES-kit (Oncogene) using AEC (AEC-kit, Vector Labs) as a substrate. Tissues were counterstained with hematoxylin. FIG. 12 shows p53 gene expression in the surface area of proliferative epithelium (left panel) and nuclear staining for p53 expression at higher magnification (right panel). No staining was detected in tumor tissue from untreated animals.

Example 9

Big CHAP (CALBIOCHEM®) Enhances Transgene Expression in Pig Urothelium

To simulate volumes expected for clinical investigation, the 7 mM Big CHAP (CALBIOCHEM®) formulation was tested in a chronically catheterized adult pig model in collaboration with SPRI Drug Safety and Metabolism. rAd-βgal ($1 \times 10^{11}$ PN/ml) was formulated in VPBS or 7 mM Big CHAP (CALBIOCHEM®). A volume of 50 ml was injected via the catheter into the bladder of the conscious animals. The instilled material was retained for 2 hr. The animals were sacrificed 48 hr later, and a central section of the bladder was harvested and stained for β-galactosidase expression. An increase in the intensity of gene expression was observed in the 7 mM Big CHAP (CALBIOCHEM®) treated pig compared to the VPBS treated pig (FIG. 11). Histologic evaluation demonstrated transduction of several epithelial layers using Big CHAP (CALBIOCHEM®) (left panel), but only superficial transduction with the VPBS buffer (right panel).

Example 10

Gene Transfer into Intestinal Epithelium in Rats

A slightly modification of the method of Sandberg et al. (Human Gene Therapy 5:323–329 (1994)) was used to prepare rat ileal segments for gene transfer studies. Briefly, female Sprague-Dawley rats were anesthetized with isoflurane. The abdominal cavity was opened and an ileal segment rostral from the last Peyer's patch isolated. The segment (about 3 cm) was cautiously cleared from food residues and both sides closed with a traumatic vascular clamps. rAd-βgal ($1 \times 10^{11}$ PN/ml), 0.5 ml volume, was directly injected into the segment with a 24 G needle and allowed to incubate for 45 minutes. rAd-βgal was formulated in 10 mM taurodeoxycholic acid (in distilled water, sterile filtered) (Treatment group 1) or VPBS (Treatment Group 2). A third treatment group comprised animals treated with 10 mM taurodeoxycholic acid. Thereafter, clamps were removed and a loose silk suture anchored on both ends for recognition at time of necropsy. The abdominal incision was closed and animals allowed to recover in their cages. Animals were sacrificed 48 hr later. The infected segment and a control segment were harvested in fixative for whole organ Xgal staining.

Figure 13:
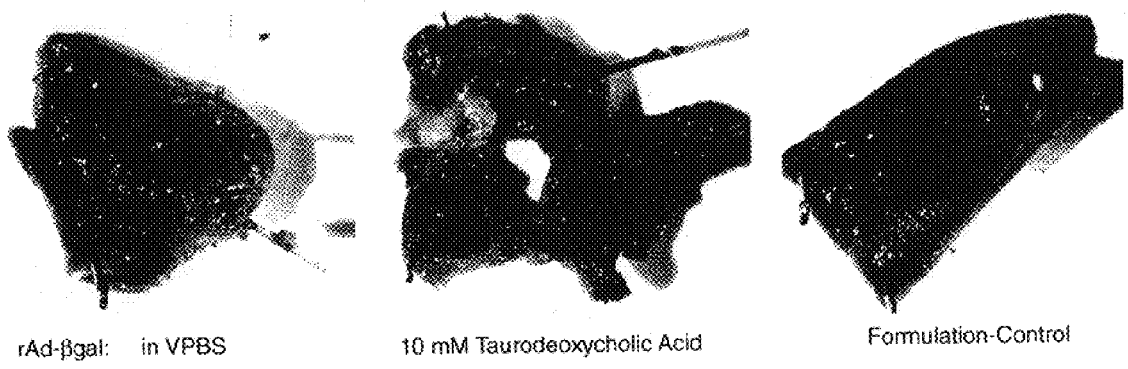
FIG. 13 depicts gene transfer to the mucosa of rat ileum.

The results are shown in FIG. 13. The extent of Xgal blue staining demonstrated evidence of transgene expression in the ileal sections. Enhanced gene transfer was evident in the detergent formulation (medial panel).

Example 11

Effect of Impurities in BIG CHAP on Gene Transfer

1. Introduction

Figure 14:
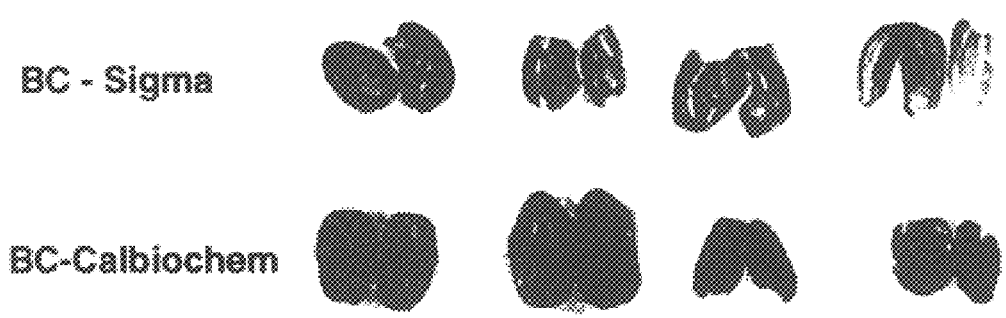
FIG. 14 is a photograph of bladder sections from rats, wherein the ability of Big CHAP from two sources to enhance gene transfer was compared. The more intense Xgal staining in the lower row in comparison to the upper row demonstrated a greater enhancement of gene transfer by Big CHAP from CALBIOCHEM® in comparison to Big Chap from Sigma (Sigma Chemical Company, St. Louis, Mo.).

Alternate commercial sources of Big CHAP (BC) were tested for the ability to enhance rAd (recombinant adenovirus) mediated gene transfer and expression, essentially according to the method described above in Example 8. It was determined that the more "pure" BC—Sigma (98% pure; Sigma Catalog: Biochemicals and Reagents for Life Science Research, 1997, page 182, #B 9518) at a concentration of 6 mg/ml did not markedly improve rAd mediated gene transfer (FIG. 14, top row). In contrast, the BC (CALBIOCHEM®; CALBIOCHEM® Biochemical & Immunochemical Catalog 1996/97, page 43, #200965, 95% pure), did substantially enhance gene transfer and expression at the same concentration (FIG. 14, bottom row).

The BC of CALBIOCHEM® and Sigma were further analyzed by TLC and purified by column chromatography. Purified BC and isolated impurities were tested for their ability to enhance rAd mediated gene transfer and expression in the bladder epithelium.

As discussed below in more detail, three impurities were isolated from BC. Two of the impurities demonstrated improvement of rAd mediated gene transfer and expression. In addition to commercial BC, both impurities are preferred for rAd formulation buffer to improve local gene delivery.

2. Analysis of Big CHAP by Thin Layer Chromatography

Figure 15:
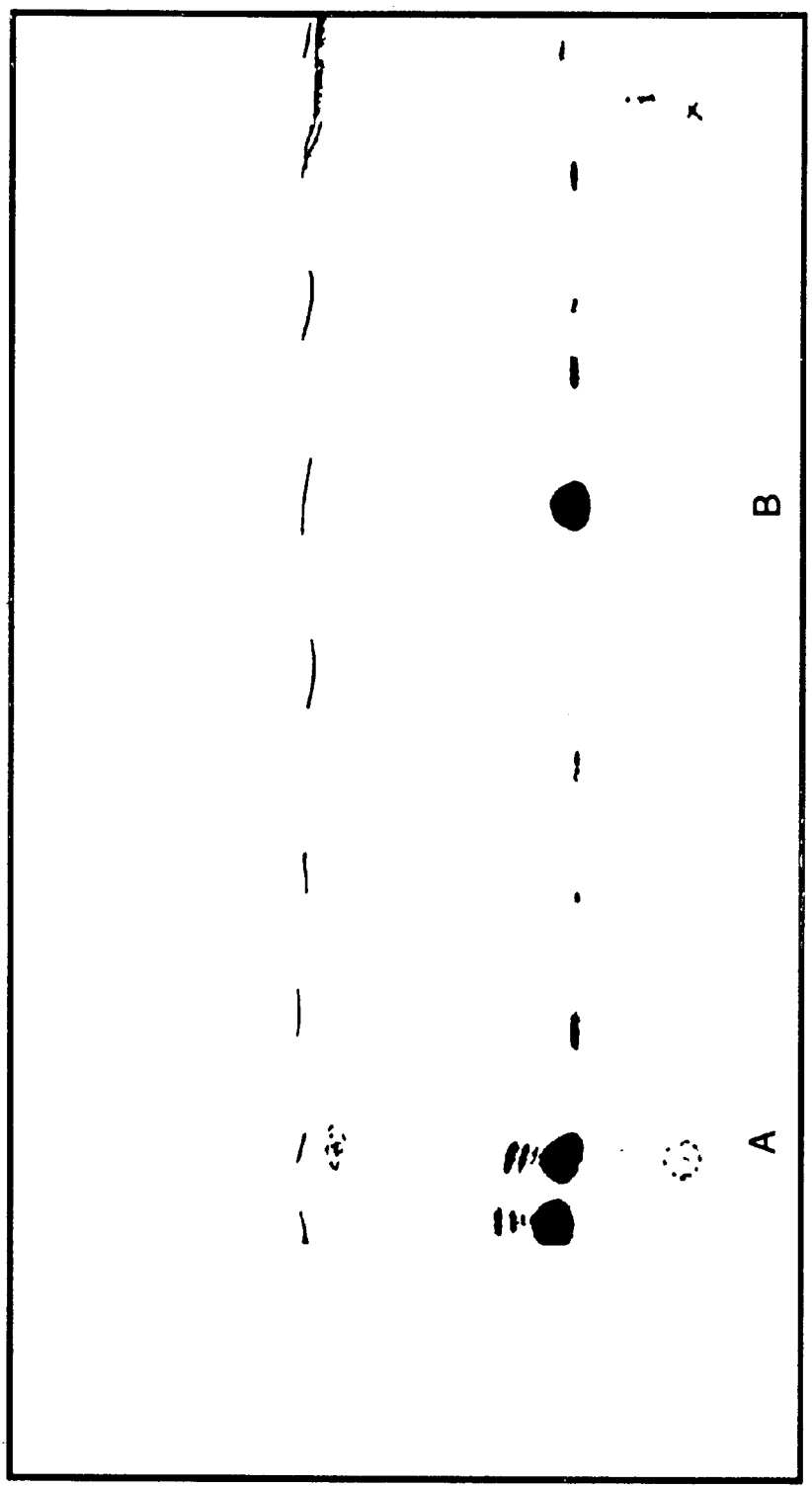
FIG. 15A and B depict thin layer chromatography (TLC) of Big CHAP from CALBIOCHEM® and Sigma. Only one distinct band developed from the sample of BC-Sigma (FIG. 15B), while three additional bands became evident in the sample of BC-CALBIOCHEM® (FIG. 15A).

BC (Sigma or CALBIOCHEM®) was dissolved in methanol/water, 3/1, and TLC performed on Silica gel 60, 0.25 mm (EM Industries); the mobile phase consisted of: 1-Butanol/Water/Glacial Acetic Acid, 6/2.5/1.5. Chromatograms were visualized with 0.5 g of thymol in sulfuric acid/ethanol, 5/95, and heat. As shown in FIG. 15, only one distinct band developed from the sample of BC—Sigma (B), while three additional bands became evident in the sample of BC-CALBIOCHEM® (A).

Figure 16:
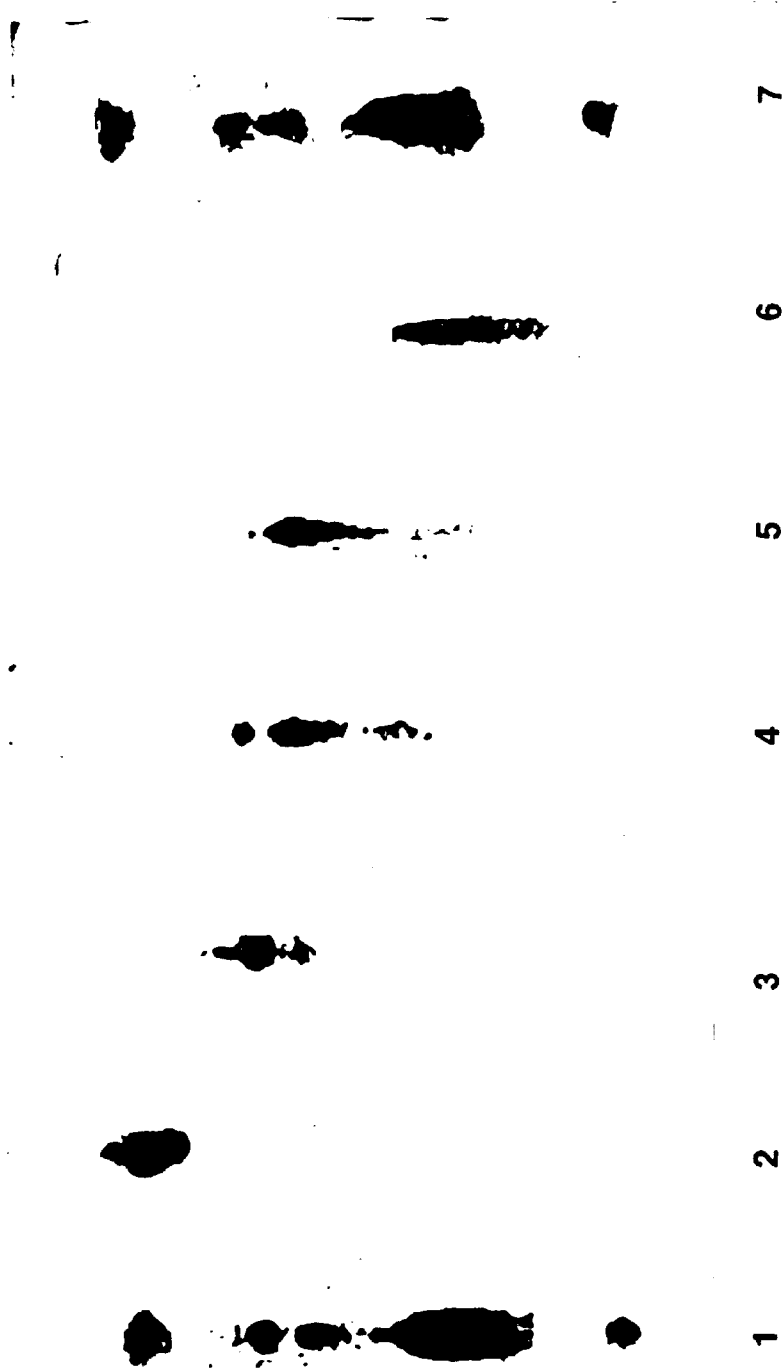
FIG. 16 depicts TLC of Big CHAP impurities. The lanes are labeled as follows: Lane 1: Big CHAP (CALBIOCHEM®); Lane 2: Impurity I; Lane 3: Impurity II; Lane 4: Mixture of Impurity II and III; Lane 5: Impurity III; Lane 6: Big CHAP (CALBIOCHEM®) pure; Lane 7: Big CHAP (CALBIOCHEM®).

Impurities of BC (CALBIOCHEM®) were further isolated by column chromatography and analyzed by thin layer chromatography (Silica Gel 60), using a mobile phase of chloroform/methanol/water, 6/5/1. The results are depicted in FIG. 16. (Lane 1: BC (CALBIOCHEM®); Lane 2: Impurity I; Lane 3: Impurity II; Lane 4: Mixture of Impurity II and III; Lane 5: Impurity III; Lane 6: BC (CALBIOCHEM®) pure; Lane 7: BC (CALBIOCHEM®).

3. Increasing Concentrations of BC (Sigma) Enhance Gene Transfer

Figure 17:
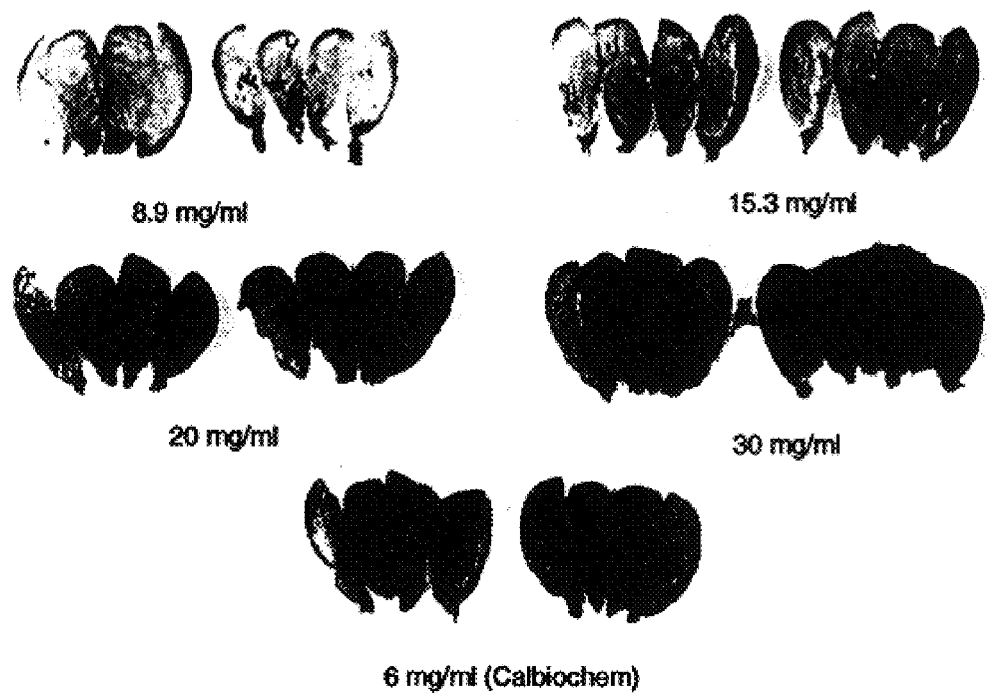
FIG. 17 is a photograph of bladder sections from rats, wherein the ability of increasing concentrations of Big CHAP (Sigma) to enhance gene transfer was compared to a Big CHAP (CALBIOCHEM®) standard. The more intense Xgal staining indicated enhanced gene transfer at higher concentrations of Big CHAP (Sigma).

To test impurities of BC for enhancement of gene transfer, rAd-βgal ($1 \times 10^{11}$ PN/ml) was formulated in increasing concentrations of BC (Sigma) and tested in animals as described above. The results are depicted in FIG. 17. A higher concentration, i.e., 20 mg/ml, of the Sigma BC improved epithelial gene expression (upper and middle panel). In comparison, similar gene expression was induced by BC (CALBIOCHEM®) at a lower concentration (6 mg/ml, FIG. 17, lower panel).

4. BC Purified by Column Chromatography does not Enhance Gene Transfer rAd-βgal was formulated in 30 mg/ml of the column chromatography purified material of both BCs and gene transfer to the bladder epithelium tested as described above. At a concentration of 30 mg/ml, gene transfer and expression was only slightly enhanced in the CALBIOCHEM® sample (FIG. 18, upper panel, right). The purified Sigma BC was without any effect (FIG. 18, lower panel, left). Purification of both BCs (Sigma or CALBIOCHEM®) resulted in decreased gene transfer and expression.

5. A mixture of Impurity II and Impurity III Enhances Gene Transfer

Three impurities of BC (CALBIOCHEM®) were detected by TLC (FIG. 15) and isolated by column chromatography for gene transfer studies. Impurity I and a mixture of impurity II and impurity III were diluted in VPBS (0.6 mg/ml or 6 mg/ml) to test their efficiency in improving rAd mediated gene transfer to the bladder epithelium. Impurity I did not lead to increased β-galactosidase gene expression in the bladder epithelium, but rather caused cystitis (FIG. 19, lower panel, right). In sharp contrast, the mixture of impurity II and III enhanced gene transfer and expression dose dependently (FIG. 19, lower panel, left). Positive control formulation (BC, CALBIOCHEM®, upper panel, left), and the negative control formulations (BC-CALBIOCHEM®, column chromatography purified and BC—Sigma) were used at a concentration of 6 mg/ml (upper panel, right).

Figure 20:
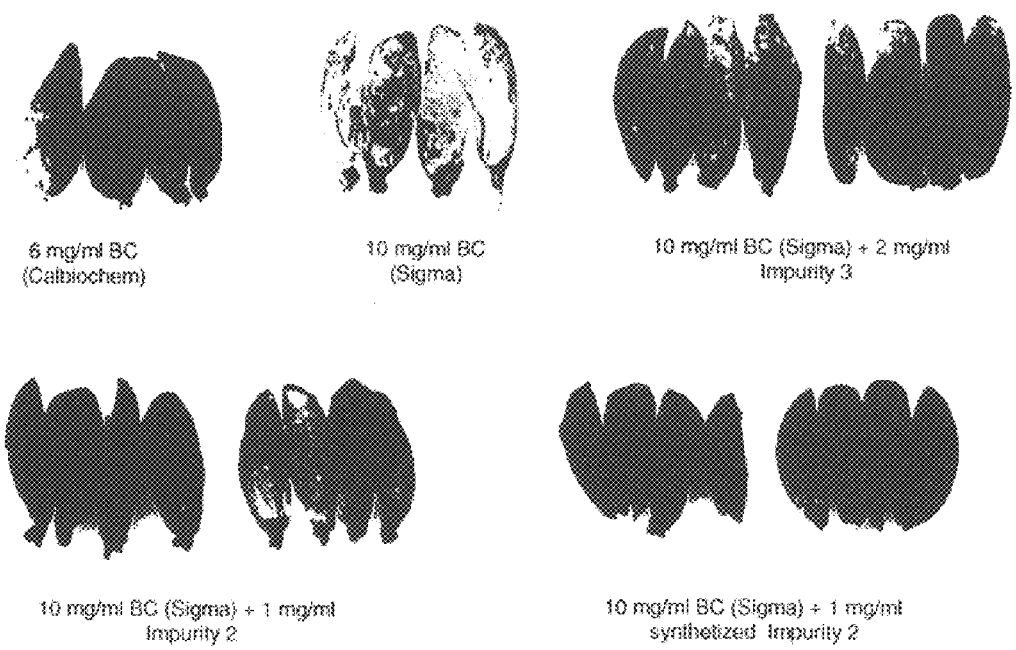
FIG. 20 is a photograph of bladder sections from rats, wherein the ability of Big CHAP (Sigma) after purification to enhance gene transfer was evaluated and compared to purified Big CHAP (Sigma) reconstituted with Impurity II, Impurity III, or a synthetic analog of Impurity II. The intensity of the Xgal staining demonstrated an enhancement of gene transfer when the purified Big CHAP (Sigma) was reconstituted. Big CHAP (CALBIOCHEM®) is included as a control.

6. Reconstitution of Impurities into Big CHAP Leads to Enhancement of Gene Transfer In this experiment, 10 mg/ml of BC (Sigma, FIG. 20 upper middle panel) was reconstituted with Impurity III (upper right panel), impurity II (lower left panel), or synthesized analog of impurity II (lower right panel). rAd-βgal, $1 \times 10^{11}$ PN/ml, was prepared in the spiked formulations and administered intravesically as described above. As shown in FIG. 20, improved reporter gene expression (β-galactosidase) was observed in the bladder epithelium of the animals that received rAd dissoluted in the "spiked" BC (Sigma) formulations at a concentration of 10 mg/ml Big CHAP (Sigma).

Example 12

Synthesis of 3-Aminopropyl-3'-N-gluconamidopropyl-amine 1.3'-N-gluconamidopropyl-3"-N-cholamidopropyl-N-cholamide Glucono-δ-lactone (0.11 mol, 17.8 g) is added in small portions to a solution of 0.11 mol (13.1) g of iminobispropylamine in 400 ml of refluxing absolute methanol. After refluxing for 2 hours, the solution is allowed to cool on ice for 1 hour. The solvent is evaporated to dryness.

2. 3-Aminopropyl-3'-N-gluconamidopropyl-amine

Triethylamine (0.2 mol, 28 ml) is added to a solution of 0.2 mol (81.6 g) of cholic acid dissolved in 500 ml of dry DMF in a 1-liter flask. The solution is cooled to 0° C. in an ice-salt bath, after which 0.2 mol (20 g) of isobutylchloroformate is added. The mixture is allowed to stand in the ice-salt bath for 5 min. after which triethylamine hydrochloride precipitate is visible. The reaction yields a mixed anhydride intermediate.

In a separate 2-liter flask, 0.1 mol (30.9 g) of 3'-N-gluconamidopropyl-3"-N-cholamidopropyl-N-cholamide is dissolved in 500 ml of DMF by gentle warming to 40–60° C. This solution is cooled rapidly in the ice-salt bath just until clouding occurs, at about 10° C. The mixed anhydride intermediate is filtered into the solution of 3'-N-gluconamidopropyl-3"-N-cholamidopropyl-N-cholamide in DMF. The triethylamine hydrochloride precipitate is removed by filtration. Thereafter, the solution is stirred with cooling for 24 hours. DMF is removed by evaporation under vacuum and heat, and the crude mixture is subjected to column chromatography on a silica gel with chloroform/methanol/water, 65/5/1, as the mobile phase. Pure fractions are collected and the solvent evaporated by vacuum. The reaction yields about 27 g (25%) product.

Mass spectral analysis of the product gave the following peaks: 337.2, 394.2, 412.2, 503.8, 682.4, 700.5, 755.1, 801.1, 823.1, 912.3, 1054.8, 1074.7, 1090.6, 1112.4, 1119.3.

Example 13

Characterization and Synthesis of Transfection-Enhancing Components in Big CHAP

As demonstrated in Example 11, impurities present in Big CHAP function to enhance gene transfer. This Example describes further characterization and synthesis of these compounds.

Calbiochem Big CHAP was fractionated by column chromatography to obtain essentially pure impurities "1", "2", and "3" for biological testing as well as structural analysis. Impurity I was not tested for biological activity because of bladder irritation that was observed in initial experiments. Because Impurities 2 and 3 were not very soluble in water, they were mixed with 6 mg/ml of Sigma Big CHAP at 0.12 and 1.2 mg/ml levels and were found to enhance gene transfer (Sigma Big CHAP alone at 6 mg/ml does not enhance gene transfer).

Figure 23:
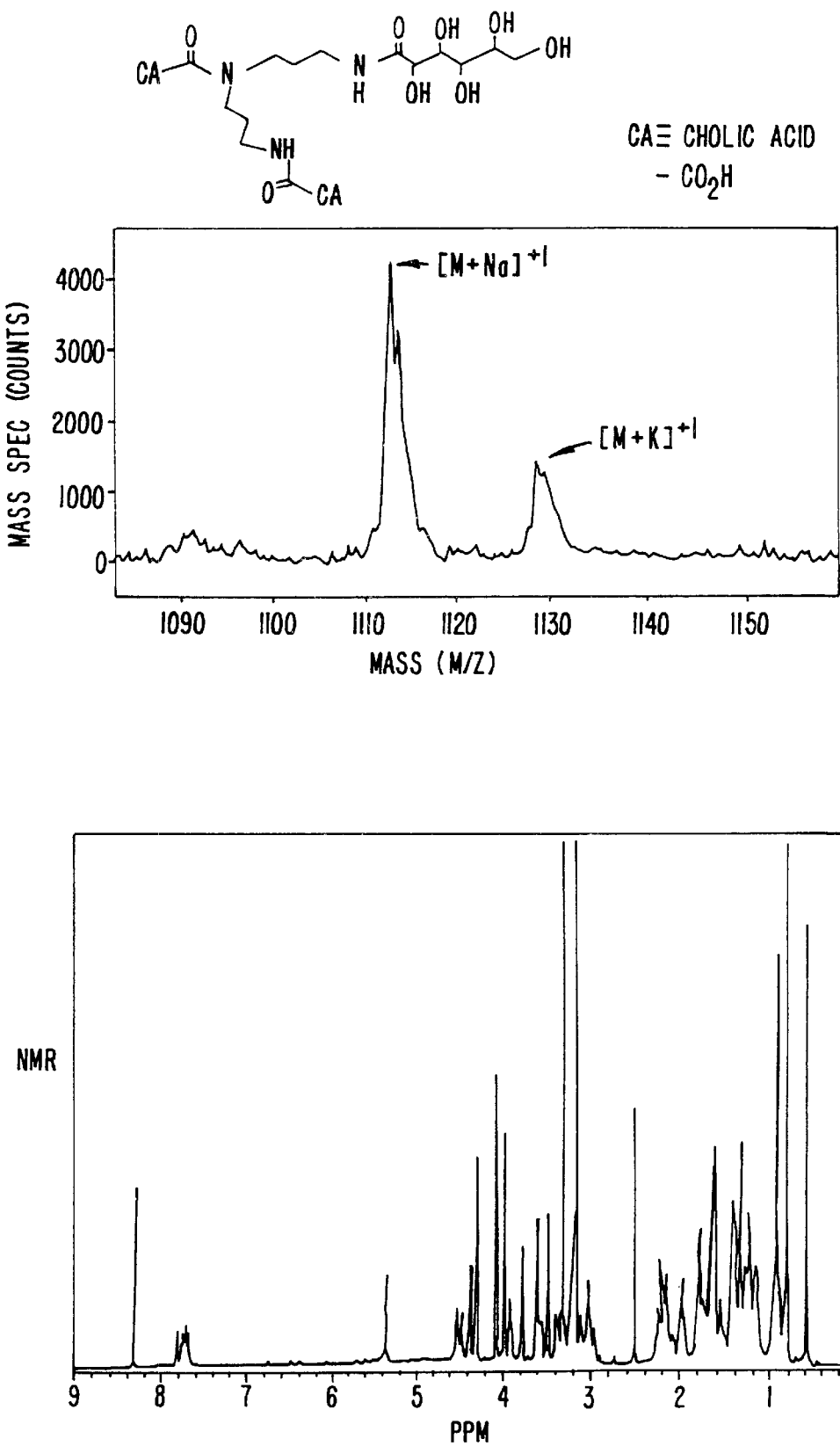
FIG. 23 shows the structure, MALDI-MS, and $^1$H-NMR of Impurity 2.

The structures of Impurities 1, 2, and 3 were determined by MALDI-MS and NMR analysis. FIG. 22 shows the structure, MALDI-MS, and $^1$H-NMR spectra of Impurity 1. The structure, MALDI-MS, and $^1$H-NMR spectra of Impurity 2 are shown in FIG. 23, and those of Impurity 3 are shown in FIG. 24. Comparison of the spectra to those of Big CHAP demonstrate that the impurities arose from the process used to synthesize Big CHAP, rather than as degradants of Big CHAP.

Crude Sigma Big CHAP was found to enhance gene transfer when used at a concentration of 26 mg/ml. To determine whether trace levels of impurities were present in Sigma Big CHAP, 1 mg was applied to a silica gel plate. An impurity comigrating with Impurity 2 in Calbiochem Big CHAP was observed. MALDI-MS and NMR confirmed that this impurity had the same structure as Impurity 2 in Calbiochem Big CHAP. Several grams of Sigma Big CHAP were fractionated by silica gel flash chromatography and the fractions containing impurities were consolidated, concentrated, and analyzed by TLC. Several impurities, including Impurities 2 and 3 were evident in this trace impurity enriched fraction.

Synthesis of Impurity 2

Figure 25:
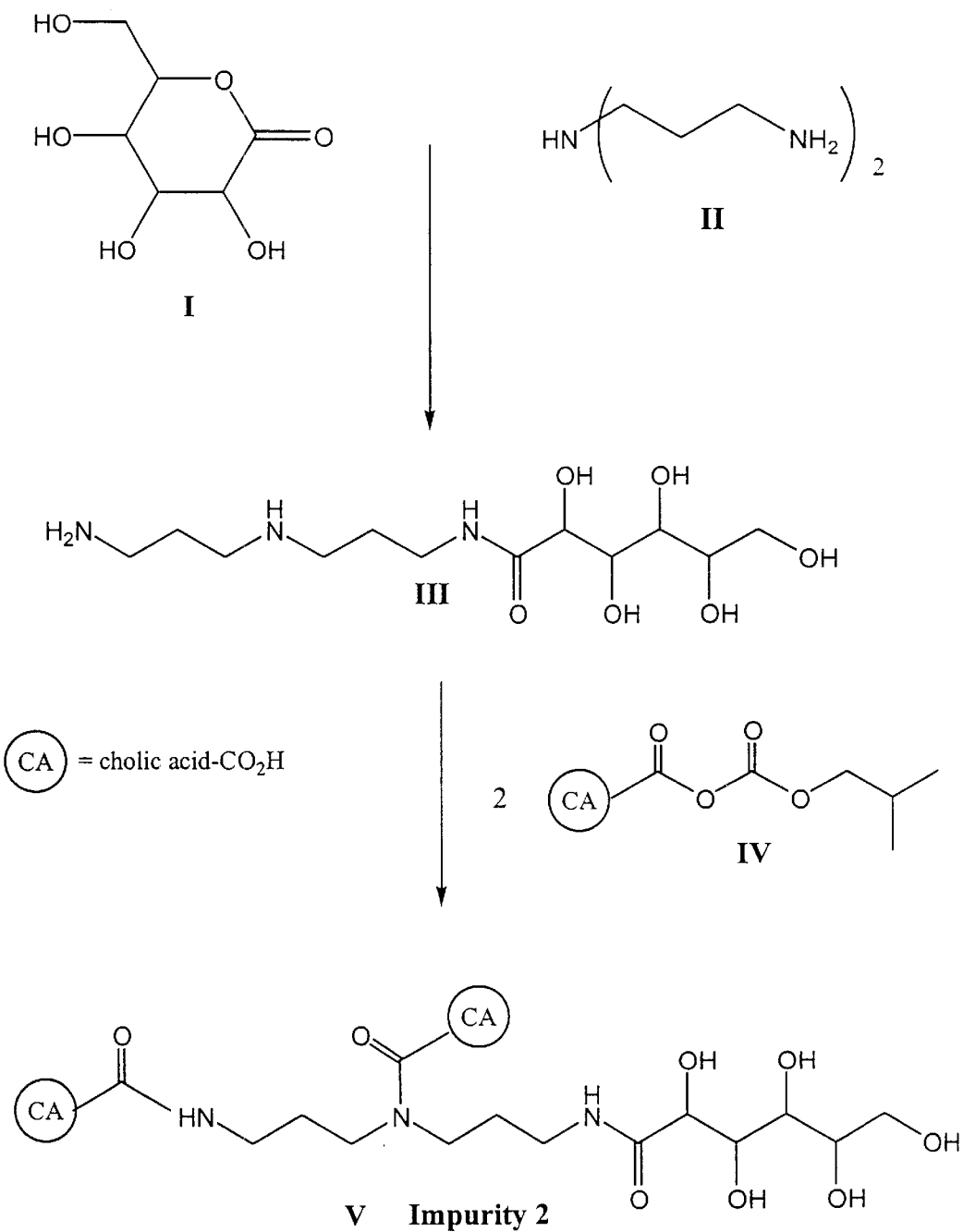
FIG. 25 shows a pathway for the synthesis of Impurity 2.

Impurity 2 was synthesized as follows (see FIG. 25). First, Compound III as shown in FIG. 25 was synthesized by dissolving 1.78 g (10 mmol) of gluconolactone in 200 ml of refluxing methanol and adding 4.2 ml (30 mmol) of N-3-aminopropyl)-1,3-propanediamene. Refluxing was continued for two hours. The methanol was then evaporated on a rotary evaporator and the resulting oil was triturated with chloroform until a white solid was formed. The white solid was filtered, washed with chloroform, and dried by suction to yield 2.1 g of product (impure Compound III).

Compound IV was synthesized by dissolving 0.65 g (1.6 mmol) of cholic acid in 40 ml of N,N-dimethylformamide with heating and stirring. The solution was then cooled in an ice bath while stirring was maintained. Triethylamine (0.223 ml (1.6 mmol)) was then added, followed by 0.208 ml (1.6 mmol) of isobutylchloroformate. A white precipitate formed as the stirring was continued for ten minutes, with Compound IV remaining in solution.

To synthesize Impurity 2 (Compound V in FIG. 25), 0.5 g (1.6 mmol) of Compound III was dissolved in 100 ml dimethylsulfoxide by stirring at 55° C. The suspension containing Compound IV was filtered into this solution and the resulting solution was stirred at room temperature overnight. Attempted separation of the dimethylsulfoxide from the product (using half of the reaction mixture) by addition of water and extraction with methylene chloride or methylene chloride/methanol was unsuccessful. The other half of the reaction mixture was distilled under vacuum to remove most of the dimethylsulfoxide. The residue was purified by silica gel flash chromatography using methanol/chloroform (40/60) as the eluent. Analysis of the fractions eluting from the column was conducted by silica gel thin layer chromatography using a mobile phase consisting of chloroform/methanol/water (6/5/1) and visualization by charring after spraying with ethanolic sulfuric acid. The fractions containing the purest product were consolidated, evaporated to dryness and triturated with hexane to produce a light tan solid which was filtered and washed with hexane. $^1$H-NMR and MALDI mass spectrometric analysis of the product were consistent with the structure shown.

Biological evaluation of this compound was somewhat hampered by its lack of solubility in water. However, even when the compound was not fully dissolved, gene transfer to bladder was enhanced by the incompletely dissolved compound. Formulation of Impurity 2 in Big CHAP, for example, did result in a formulation that is effective for enhancing gene transfer to cells.

Synthesis of Syn3 (Impurity 3 Analog)

Since Impurity 3 is more polar, and hence more water soluble, than Impurity 2, the synthesis of this compound was attempted. Purified Big CHAP was reacted with the mixed anhydride of cholic acid (formed by reacting cholic acid with isobutylchloroformate). The reaction resulted in poor yield and many products, so an analog of Impurity 3 was synthesized. This analog, which has a polarity similar to that of Impurity 3, was termed "Syn3".

Part 1: Synthesis of Compound III

Figure 26:
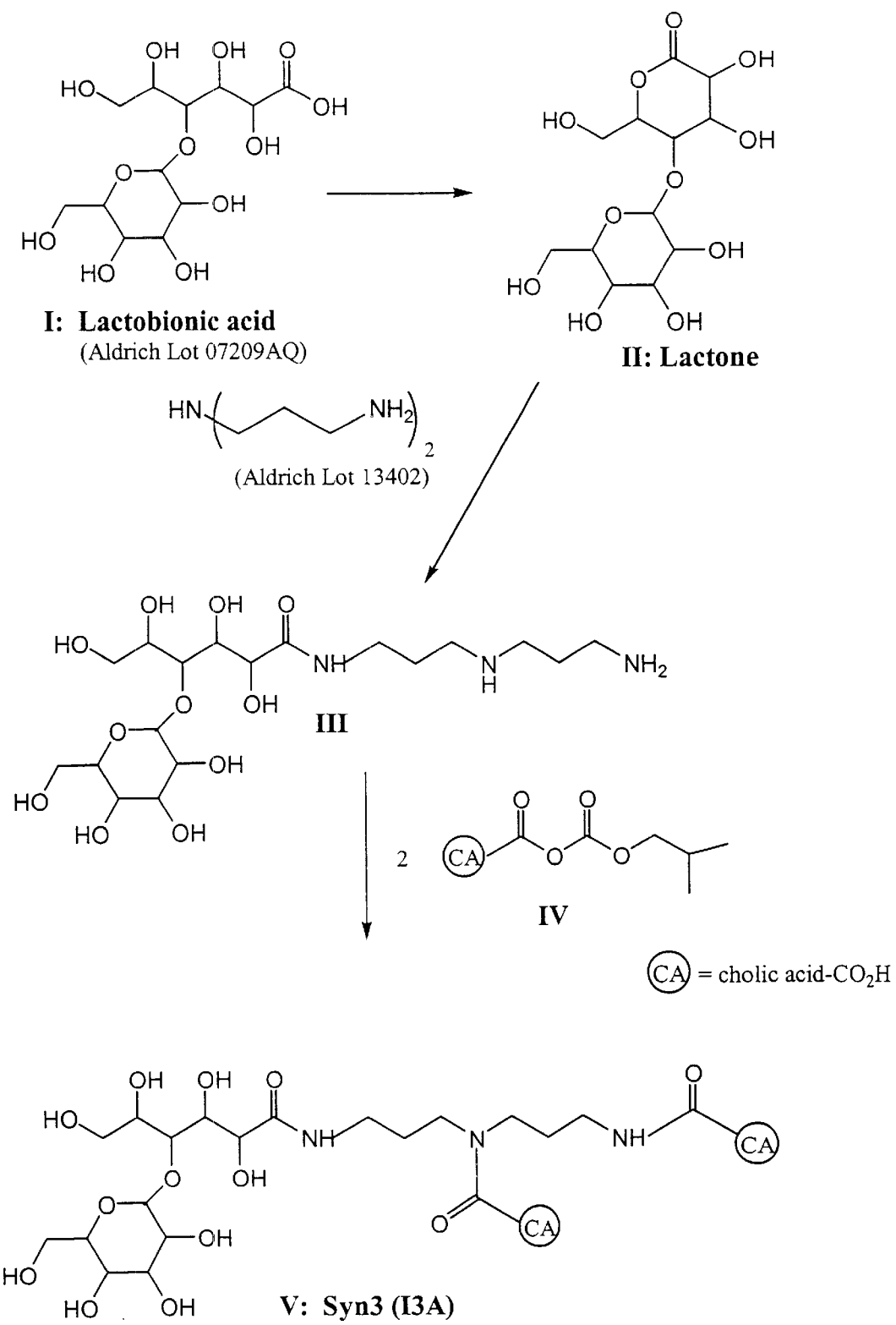
FIG. 26 shows a pathway for the synthesis of Syn3. An alternative pathway for Syn3 synthesis is shown in FIG. 34.

The synthetic scheme for Syn3 is shown in FIG. 26. The lactone of lactobionic acid (II) was synthesized by dissolving one g (2.8 mmol) of lactobionic acid (I) in 50 ml of methanol, evaporating to dryness on a rotary evaporator, and repeating this a process six times. To obtain Compound III, the resulting residue (II) was dissolved in 50 ml of isopropanol by heating to 50° C. To this solution was added 1.2 ml (8.4 mmol) of N-3-aminopropyl)-1,3-propanediamene. The temperature was increased to 100° C. and the solution was stirred for three hours. The solvent was removed by rotary evaporation and the resulting residue was washed several times with chloroform to remove excess unreacted N-(3-aminopropyl)-1,3-propanediamene. The remaining residue (III) was used as is in Part 3 below.

Part 2: Synthesis of Compound IV

Compound IV was synthesized by dissolving 2.28 g of cholic acid (5.6 mmol) in N,N-dimethylformamide by heating to 60° C. Triethylamine (0.78 ml (5.6 mmol)) was added and the solution was cooled in an ice bath. Isobutyl chloroformate (0.73 ml (5.6 mmol)) was then added and a white precipitate formed as the stirring was continued for ten minutes.

Part 3: Synthesis of Syn3 (Compound V)

Compound III was dissolved in N,N-dimethylformamide, cooled in an ice bath, and stirred. The suspension resulting from the synthesis of Compound IV was filtered into the solution containing Compound III. The resulting solution was stirred at room temperature for 6 hrs. The solvent was removed using high vacuum rotary evaporation and the residue was dissolved in 100 ml of chloroform/methanol (50/50). Twenty-five ml of this solution was purified by silica gel flash chromatography using chloroform/methanol (60/40) as the elution solvent. Analysis of the fractions eluting from the column was conducted by silica gel thin layer chromatography using a mobile phase consisting of chloroform/methanol/water/concentrated ammonium hydroxide (100/80/10/5). The compounds were visualized by charring after spraying with ethanolic sulfuric acid. Fractions containing product were consolidated and repurified using flash chromatography and chlroform/methanol/water/concentrated ammonium hydroxide (100/80/10/5) as the elution solvent. Fractions containing product were consolidated and evaporated to a white powder (300 mg of Compound V). $^1$H-NMR and MALDI mass spectrometric analysis of the product were consistent with the structure shown.

Syn3 formed a gel when dissolution was attempted at 10 mg/ml in water and appeared to form vesicles at 1 mg/ml. However, at 1 mg/ml in 0.1% Tween 80 a clear solution of Syn3 resulted. This formulation was found to enhance gene transfer. Tween 80 alone, when tested, had no effect on gene transfer.

Purified Big CHAP spiked with Impurities 2 or 3 is an effective enhancer of gene transfer. Synthetic Impurity 2 alone and a synthetic analog of Impurity 3 (Syn3) alone can enhance gene transfer. Therefore, a synergistic relationship between Big CHAP and the impurities is not required for gene transfer enhancement. Big CHAP is highly water soluble and is effective in bringing the impurities and their analogs into solution, probably as mixed micelles, thus serving as a vehicle for the active impurities and/or analogs.

While Impurity 2 is effective in enhancing gene transfer, its has limited solubility in aqueous solutions, although it is useful when formulated in a suitable solubilizing agent such as Big CHAP. In contrast to Impurity 2, Syn3 is readily solubilized in, for example, 1 mg/ml in 0.1% Tween 80 and other aqueous solutions as described herein. Thus, this compound is particularly useful as a gene transfer enhancement agent.

Example 14

Efficacy of Synthetic Impurity 3 Analog (Syn3) for Enhancing Gene Transfer to the Bladder This Example demonstrates that the Syn3 analog of Impurity 3 is effective in enhancing gene transfer to the bladder.

Methods

1. Dissolution of Sy3

Initial testing of Syn3 indicated that it is not highly soluble in either buffered saline or $dH_2O$. However, Syn3 was found to be fairly easily dissolved into the detergent Big CHAP, as well as into the detergent Tween-80 (although with somewhat more difficulty compared to dissolution into Big CHAP). The higher the concentration of the Big CHAP solution used for dissolution, the greater the amount of Syn3 that could be dissoluted. Up to 5 mg/ml of Syn3 was found to dissolute into 15 mM Big CHAP.

For the following studies using Syn3 in Tween-80, a 100 mg/ml solution of Syn3 was prepared in 10% Tween-80. This stock solution was dilution in $dH_2O$ (1:100) to give a final concentration of 1 mg/ml Syn3 in 0.1% Tween-80.

Table II summarizes the concentrations of Syn3 that were chosen for testing in vivo:

TABLE II

| Concentration of Syn3 in detergent | Formulation | Final Concentration of Syn3 with rAd |
| --- | --- | --- |
| 5.0 mg/ml | 15 mM Big CHAP | 4.5 mg/ml |
| 0.5 mg/ml | 7.8 mM big CHAP | 0.45 mg/ml |
| 0.25 mg/ml | 3.9 mM Big CHAP | 0.22 mg/ml |
| 1.0 mg/ml | 0.40% Tween-80 | 0.90 mg/ml |
| 1.0 mg/ml | 0.10 Tween-80 | 0.45 mg/ml |
| 0.50 mg/ml | 0.05% Tween-80 | 0.22 mg/ml |

2. In Vivo Testing

The gene transfer activity of Syn3 was tested in vivo by determining the level of β-galactosidase expression found following, administration of adenovirus containing the β-galactosidase gene delivered in one of the above detergent solutions. In this procedure, female Harlan Sprague-Dawley rats were catheterized and administered adenovirus diluted 1:10 in either Big CHAP or Tween-80 containing Syn3 at one of the above concentrations for 45 minutes. Following removal of virus and flushing of the bladder, the animals were allowed to recover. After 48 hours the animals were sacrificed, their bladders fixed, and stained for β-gal expression. Following photographic recording, bladders were embedded in paraffin for sectioning and histological examination.

Results

1. Gene Transfer Activity of Syn3 in Big CHAP

Figure 27:
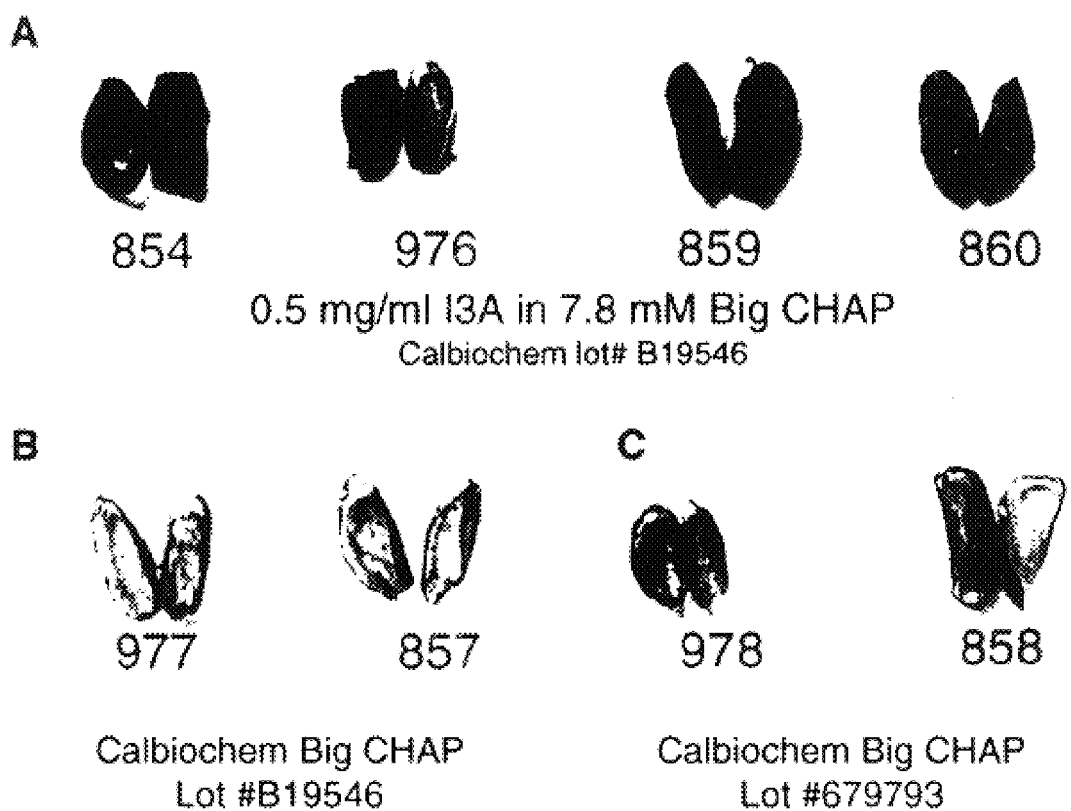
FIG. 27A–FIG. 27C demonstrate that I3A (Syn3) enhances adenovirus-mediated β-galactoside expression. High levels of gene transfer were obtained when using I3A at 0.5 mg/ml in 7.8 mM Big CHAP (FIG. 27A). Controls are shown for comparison: no I3A (FIG. 27B) and as the positive control, 7.8 mM Big CHAP Calbiochem Lot #679693 (FIG. 27C).

Syn3 was tested at 0.5 mg/ml in 7.8 MM Big CHAP. At this concentration, it was relatively easily dissoluted, and sterile filterable (0.2 μm Acrodisc syringe filter; Gelman Sciences). Initial experiments utilized Calbiochem Big CHAP, lot # B19546, while later experiments utilized Sigma Big CHAP lot #37H5023. Neither stock of Big CHAP has experiments gene transfer activity alone at the concentration employed. As a positive control, Calbiochem lot #679793 was utilized as a formulation for rAd delivery. This particular lot of Big CHAP was identified as containing the active impurities which were identified and from which Syn3 was modeled. As seen in FIG. 27, Syn3 (I3A) was found to greatly enhance gene transfer and β-gal expression compared to administration of the virus alone in 7.8 mM Big CHAP.

Figure 28:
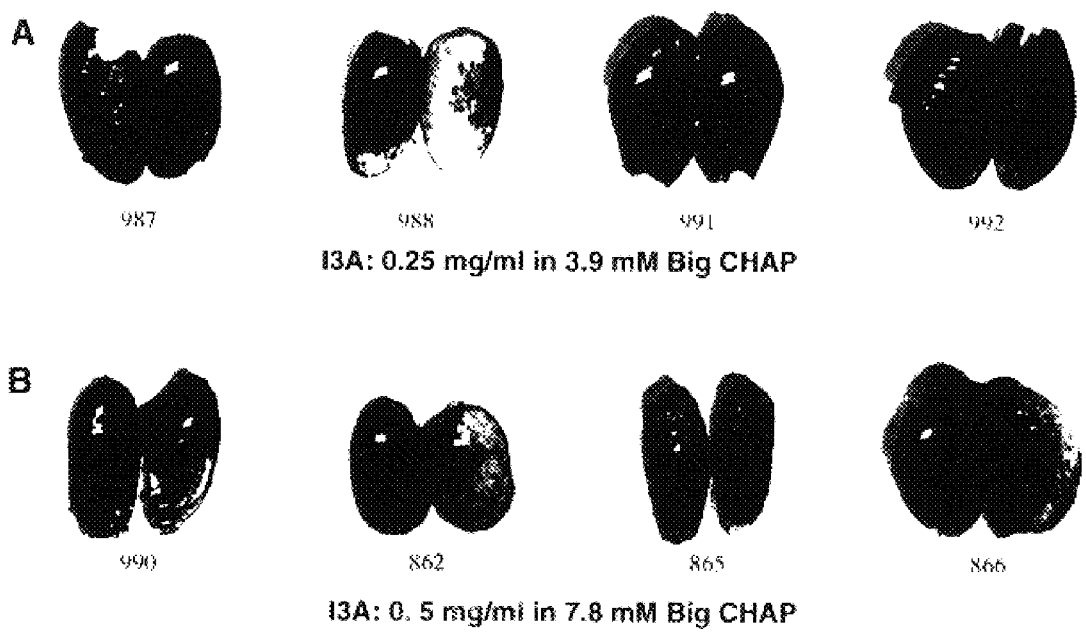
FIG. 28A and FIG. 28B show the results of a titration of gene transfer enhancing activity of I3A (Syn3). Reduction of I3A to 0.25 mg/ml in 3.9 mM Big CHAP (FIG. 28A) still yielded high levels of gene transfer activity compared to the gene transfer activity obtained when using I3A at 0.5 mg/ml in 7.8 mM Big CHAP (FIG. 28B). At time of fixation, bladders treated with 0.25 mg/ml I3A appeared to have less inflammation than those treated with 0.5 mg/ml I3A.

To determine whether lower concentrations of Syn3 might prove as efficacious at enhancing gene transfer as higher concentrations, Syn3 was administered at 0.25 mg/ml in 3.9 mM Big CHAP (FIG. 28A). Very high levels of gene transfer were obtained, but not quite as consistently high as seen with Syn3 at 0.5 mg/ml (FIG. 28B).

2. Gene Transfer Activity of I3A/Syn3 in Tween-80

Figure 29:
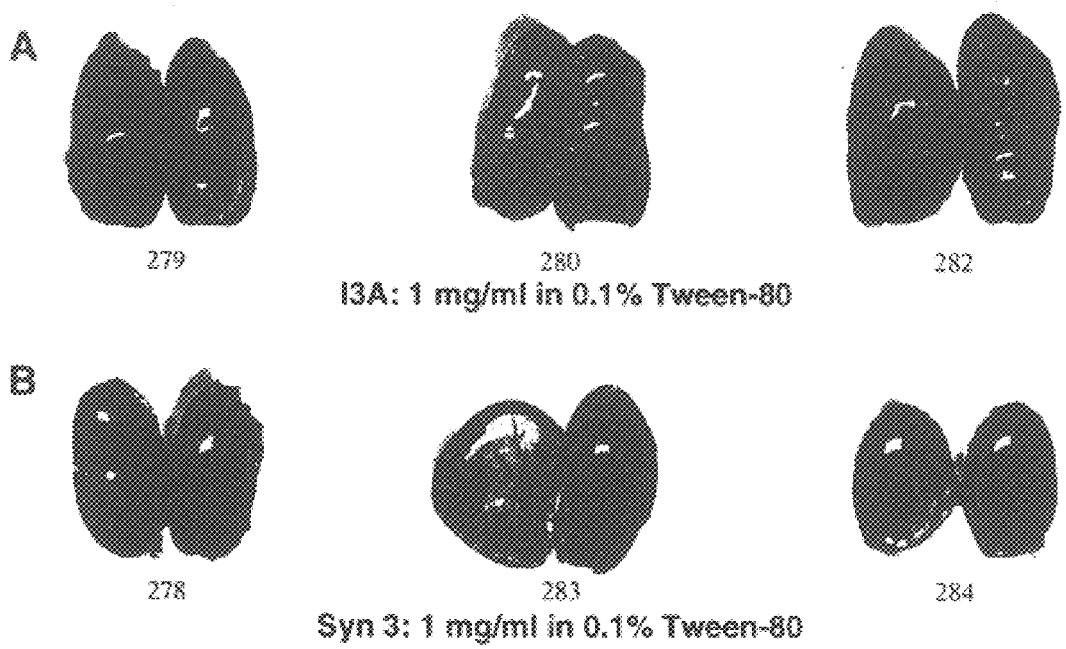
FIG. 29A–FIG. 29B show a comparison of I3A and Syn3 gene transfer activity. High levels of β-galactosidase activity were obtained using I3A at 1 mg/ml in 0.1% Tween 80 (FIG. 29A). Approximately equal levels of gene transfer were obtained using Syn3 at 1 mg/ml in 0.1% Tween 80 (FIG. 29B).

Initial testing of I3A in Tween-80 began using I3A at 1 mg/ml in 0.4% Tween-80. However, almost no gene transfer was obtained when this concentration of Tween was used (data not shown). Since it was hypothesized that the high concentration of Tween-80 might have been sequestering the I3A from partitioning into the membrane and permitting viral penetration, the concentration of Tween-80 was reduced to 0.1%, keeping the concentration of I3A at 1 mg/ml. Two different preparations of Syn3 were tested for their gene transfer activity at 1 mg/ml in 0.1% Tween-80. At this concentration, very high levels of gene transfer were seen when using either the first lot (I3A) (FIG. 29A) or the second lot of Syn3 (FIG. 29B). The second lot of Syn3 had also demonstrated very high levels of gene transfer activity at 0.5 mg/ml in 7.8 μM Big CHAP, so all future experiments were carried out using Syn3 instead of I3A.

Figure 30:
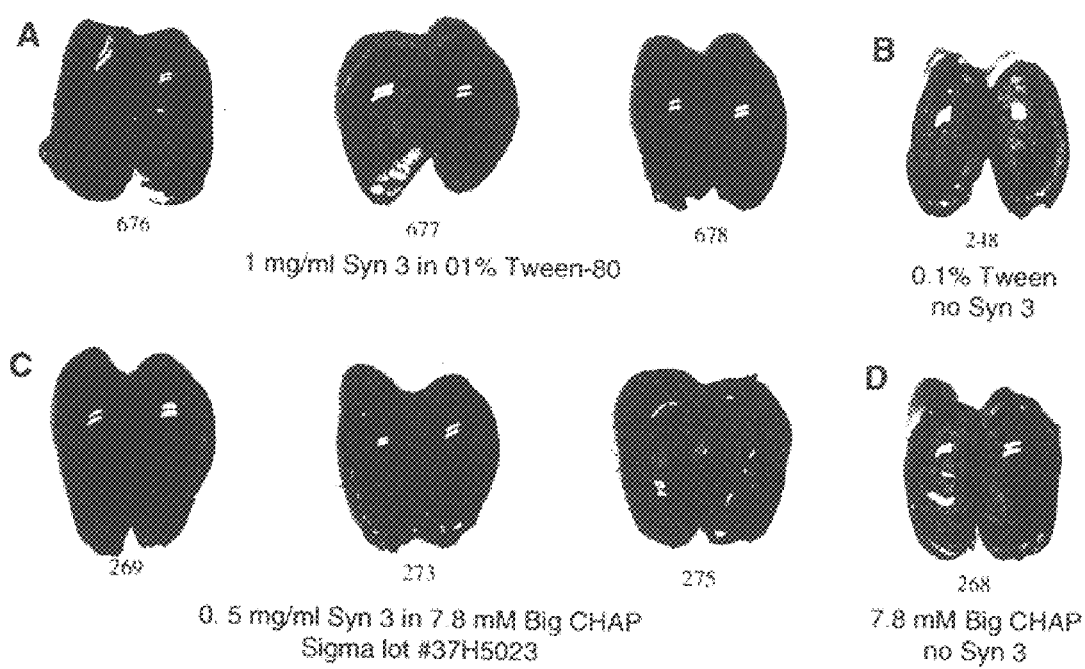
FIG. 30A–FIG. 30D shows a comparison of Syn3 gene transfer activity in 0.1% Tween 80 vs. 7.8 mM Big CHAP. Using Syn3 at 1 mg/ml in 0.1% Tween 80 (FIG. 30A) resulted in levels of gene transfer that were comparable to those obtained when using Syn3 at 0.5 mg/ml in 7.8 mM Big CHAP (FIG. 30C). Shown also are negative controls (no Syn3) when using either 0.1% Tween 80 (FIG. 30B) or 7.8 mM Big CHAP (FIG. 30D).

The gene transfer activity of Syn3 in Big CHAP (0.5 mg/ml in 7.8 MM) was compared to its activity in Tween-80 (1 mg/ml in 0.1% Tween-80). Both formulations were found to have approximately equal levels of gene transfer enhancement with perhaps slightly greater transfer seen with the Syn3 in Big CHAP (FIG. 30A and FIG. 30C respectively). Since the β-galactosidase assay is not highly quantitative, small differences are difficult to discern. However, bladders treated with Syn3 at 0.5 mg/ml in 7.8 mM Big CHAP consistently had the highest levels of β-galactosidase expression. Syn3 increases gene transfer in either detergent, although it is not as easily dissoluted into the Tween-80.

Figure 31:
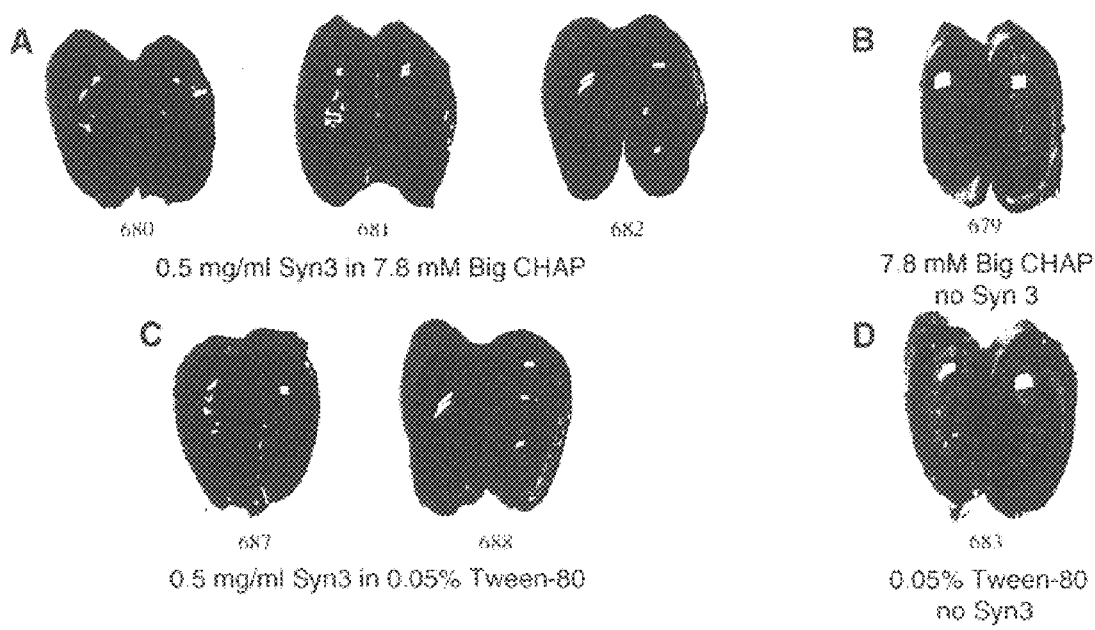
FIG. 31A–FIG. 31D show a comparison of Syn3 gene transfer activity at equal concentrations in Big CHAP and Tween 80 detergents. When Syn3 was dissoluted at 0.5 mg/ml in 7.8 mM Big CHAP (FIG. 31A), very high levels of gene transfer were obtained. In comparison, the gene transfer activity of Syn3 in 0.05% Tween 80 (FIG. 31C) was slightly reduced, with more regions devoid of β-galactosidase activity. Negative controls for both 7.8 mM Big CHAP (FIG. 31B) and 0.05% Tween 80 (FIG. 31D) are also shown.

Since the concentration of Syn3 in Big CHAP was twice that in Tween, Syn3 was next tested for its gene transfer activity at the same concentration in these two detergents. At 0.5 mg/ml, Syn3 appeared to give better gene transfer in 7.8 mM Big CHAP (FIG. 31A), than what was obtained using Syn3 in 0.05% Tween-80. When Syn3 was used at 0.5 mg/ml in 0.05% Tween-80, there appeared to be more regions lacking β-galactosidase expression, similar to what was observed when the concentration of Syn3/(I3A) was reduced to 0.25 mg/ml in 3.9 mM Big CHAP (FIG. 28A). This suggests that some of the differences in gene transfer-activity of Syn3 in Big CHAP vs. Tween-80 are probably due in part to effects from the detergent into which Syn3 was dissolved.

3. Histological Examination of Syn3 Treated Bladders

Figure 32:
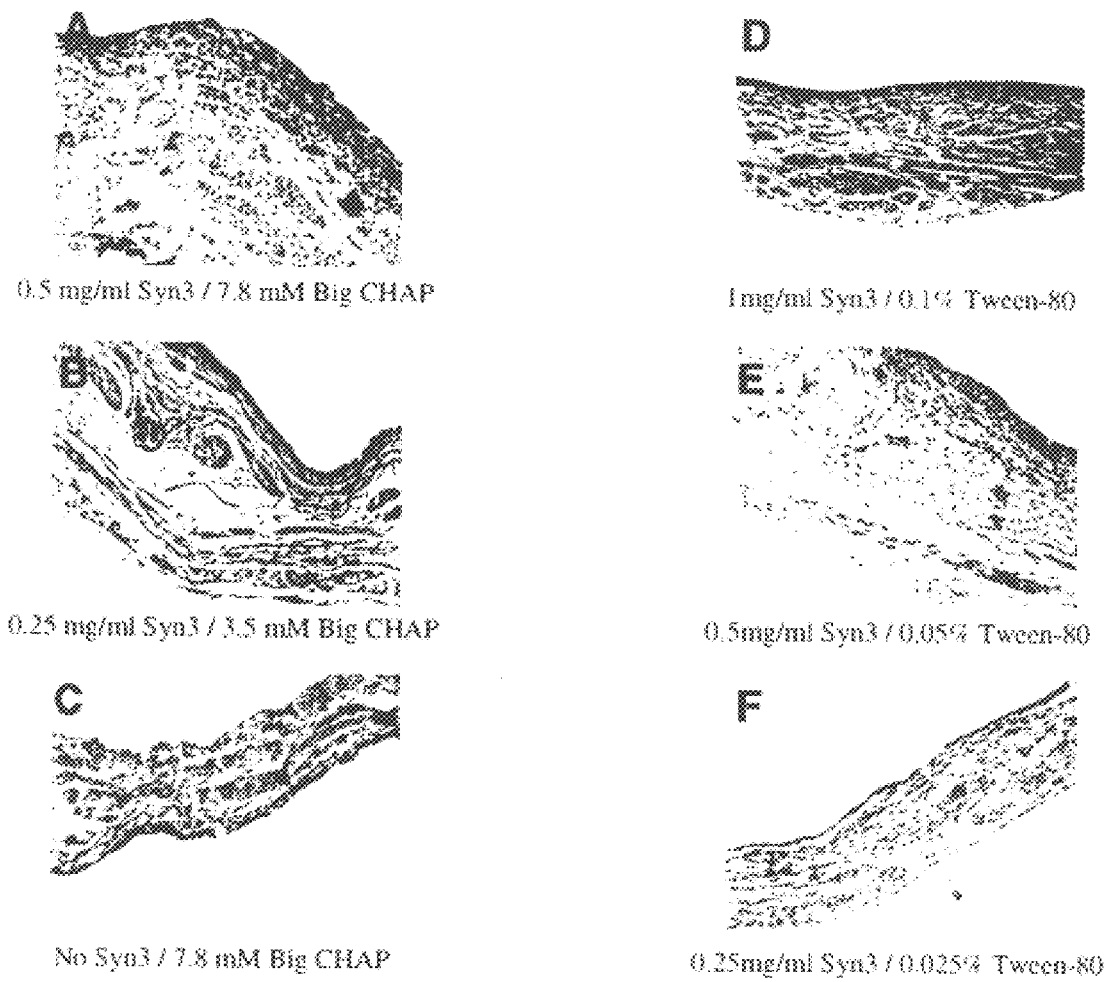
FIG. 32A–FIG. 32F show a comparison of infiltration following Syn3 administration. At lower doses of Syn3, proportionally lower infiltration was observed in the bladder. Decreasing concentrations of Syn3 were used for rAd infection of bladders when using either Big CHAP (FIG. 32A, B) or Tween 80 (FIG. 32D, E). Also shown are bladders treated with detergent only (no Syn3) with either Big CHAP (FIG. 32C) or Tween 80 (FIG. 32F).

Bladders from animals treated with Syn3-rAd (β-Gal) were prepared for histological examination to determine the levels of viral infection, as well as the degree of viral penetration into the bladder urothelium. Reducing the concentration of Syn3 in either detergent resulted in a concomitant reduction in β-Gal expression (FIG. 32A-F). Although the β-galactosidase expression resulting from administration of Syn3 at 0.5 mg/ml in 7.8 mM Big CHAP was slightly greater than with Tween-80 (FIG. 32A vs. FIG. 32D), it was noted that this concentration of Syn3 typically results in a massive recruitment of infiltrates to the bladder (FIG. 32A).

Figure 33:
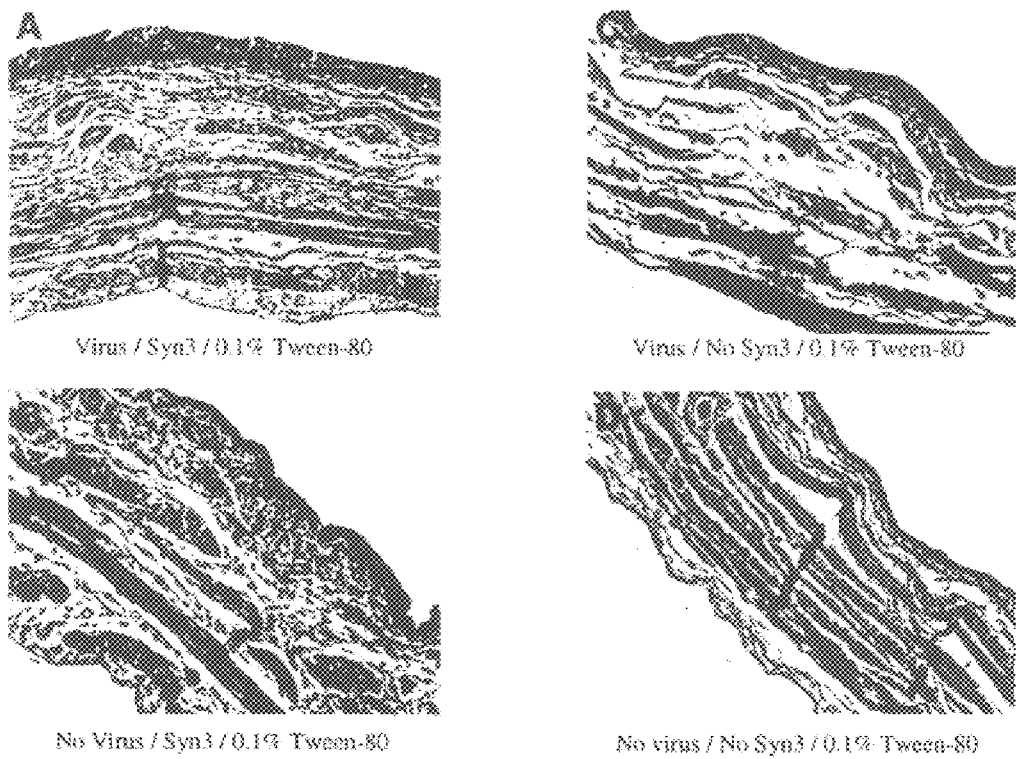
FIG. 33A–FIG. 33D shows that administration show that administration of Syn3 results in induction of cellular infiltrates. When the level of infiltration resulting from administration of virus and Syn3 (FIG. 33A) was compared to the level obtained from Syn3 alone (FIG. 33B), it was found that Syn3 administration results in a significant induction of infiltrates. Also shown are bladders from animals treated with virus only (FIG. 33C) or a no virus/no Syn3 control (FIG. 33D).
Figure 34:
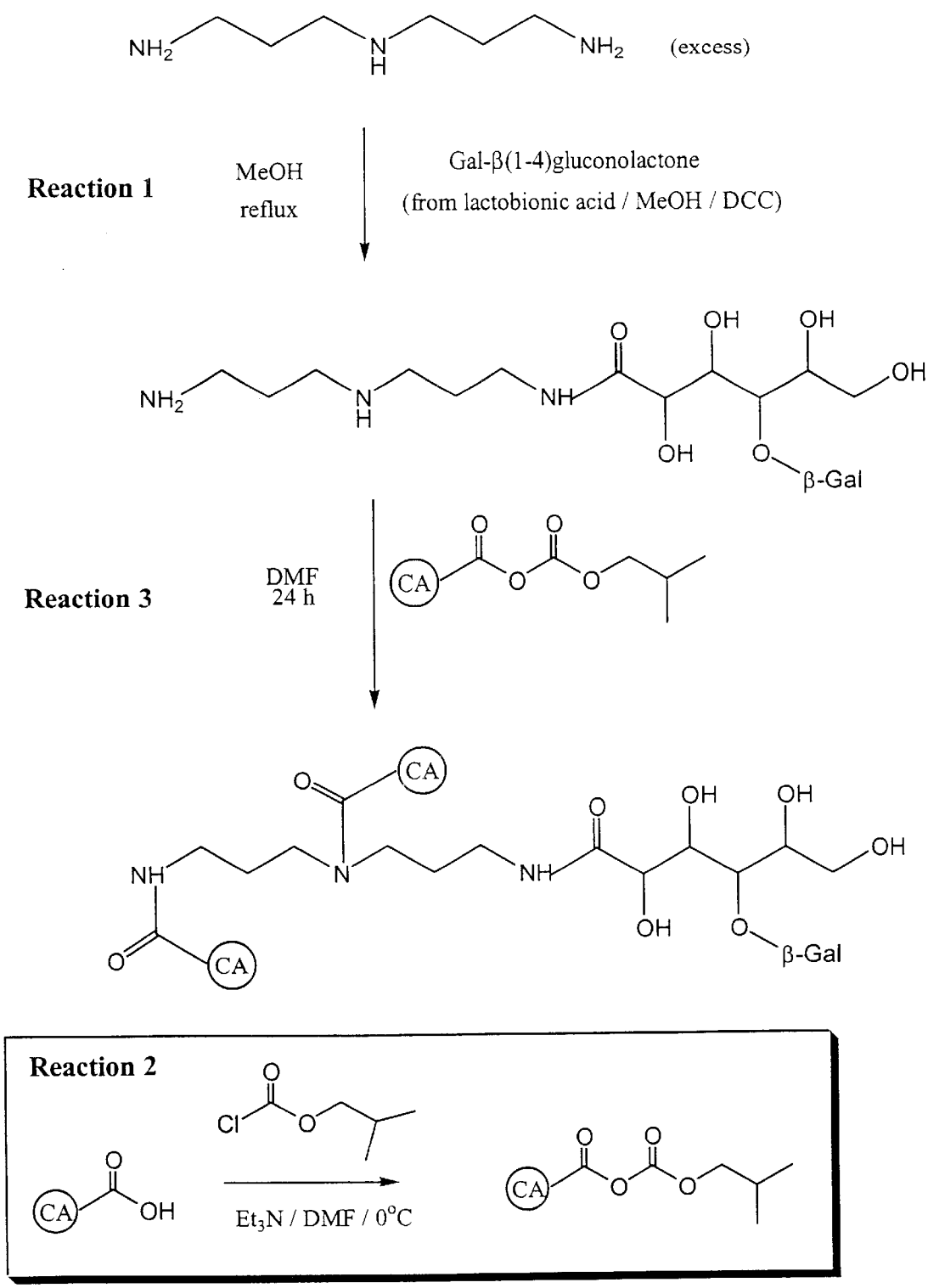
FIG. 34 shows a pathway for synthesis of Syn3. After Reaction 3 was conducted in DMF for 24 hours, the product was evaporated to dryness, and purified on $SiO_2$ with DCM/MeOH/$H_2$O (60:35:5).

Since the β-galactosidase expression and the level of infiltrates was higher in the bladders in which Syn3 was used at 0.5 mg/ml in Big CHAP than in the bladders in which Syn3 was at 1 mg/ml in Tween-80, this suggests that the infiltration was due to the increase in viral penetration and expression that occurs when rAd is administered in the Big CHAP. In order to discern the contribution that Syn3 may have in the recruitment of infiltrates, sections of bladders that were exposed to Syn3 and virus were compared to those that had been exposed to Syn3 alone (FIG. 33A and FIG. 33B, respectively). When Syn3 is administered alone, a significant amount of infiltration is seen, only slightly less than that seen with Syn3 and virus together. Virus administered without Syn3 resulted in extremely low levels of infection and infiltrates (FIG. 33C), while the negative control (no virus, no Syn3) shows no infiltration (FIG. 33D).

4. Stability of Syn3 in Solution

Syn3 is very stable when dissoluted into Big CHAP detergent. When Syn3 was dissoluted into Big CHAP at either 0.25 mg/ml or 0.5 mg/ml, it retained its gene transfer activity for extended periods (30 days or longer) even when stored at room temperature. When Syn3 was dissoluted at 100 mg/ml into 10% Tween-80, it was stable for at least one week when kept at 4° C. However, if left at room temperature at this high concentration (100 mg/ml), it will solidify within 24 hours. Syn3 that has been diluted to 1 mg/ml in 0.1% Tween-80 is stable for at least 30 days (longest period tested).

Conclusions

The gene transfer activity of Syn3 appears to be extremely high at 0.5 mg/ml in 7.8 mM Big CHAP. However, lower concentrations of Syn3 are preferred (e.g., 0.25 mg/ml in 3.9 mM Big CHAP) due to the possibility of side effects at higher concentrations. Syn3 has also demonstrated consistently high levels of gene transfer at 1 mg/ml in 0.1% Tween-80. Based upon the results of these studies, one particularly suitable formulation of Syn3 for use as a gene transfer agent is at 1 mg/ml in 0.1% Tween-80.

Example 15

Clinical Formulation of Syn3

This Example provides, for illustrative purposes, one example of a formulation of Syn3 that is suitable for use as a clinical formulation for delivery of a viral vector. This formulation can also be used for other delivery enhancing compounds; many other formulations such as those described herein are also suitable for use with Syn3 and other compounds.

A Syn3 stock solution was prepared by dissolving Syn3 at 100 mg/ml in 10% Tween 80. This stock solution was then diluted to a Syn3 concentration of 6 mg/ml using an aqueous buffer containing Tris (1.7 mg/ml), sodium phosphate (monosodium, dihydrate, 1.7 mg/ml), sucrose (20 mg/ml), magnesium chloride (hexahydrate, 0.4 mg/ml), and glycerol (100 mg/ml) in water.

This solution was diluted with a solution containing the viral vector to obtain a virus solution that contained 1 mg/ml Syn3 in 0. 1% Tween 80. This solution was effective in enhancing gene transfer.

Example 16

Synthesis of Syn3 Analogs that have Increased Solubility in Water

Syn3 has demonstrated high gene transfer-enhancing activity in vivo, but is relatively insoluble in aqueous solutions, and requires the presence of detergent for complete dissolution. In addition, Syn3 requires several hours to completely dissolute into 10% Tween-80, further complicating clinical use of this reagent. To resolve these difficulties, two analogs of Syn3 were synthesized which have greater solubility in aqueous solution. By removal of the lactose moiety of Syn3 and subsequent methylation or reduction of the resulting amine, two novel compounds were synthesized which are known as A-Trimethylammonium chloride (A-tma) and A-Hydrochloride (A-HCl), respectively, where A represents the conserved region of Syn3 common to both molecules (see FIG. 21). These two cationic compounds were further neutralized to their chloride salt for ease of dissolution.

Figure 35:
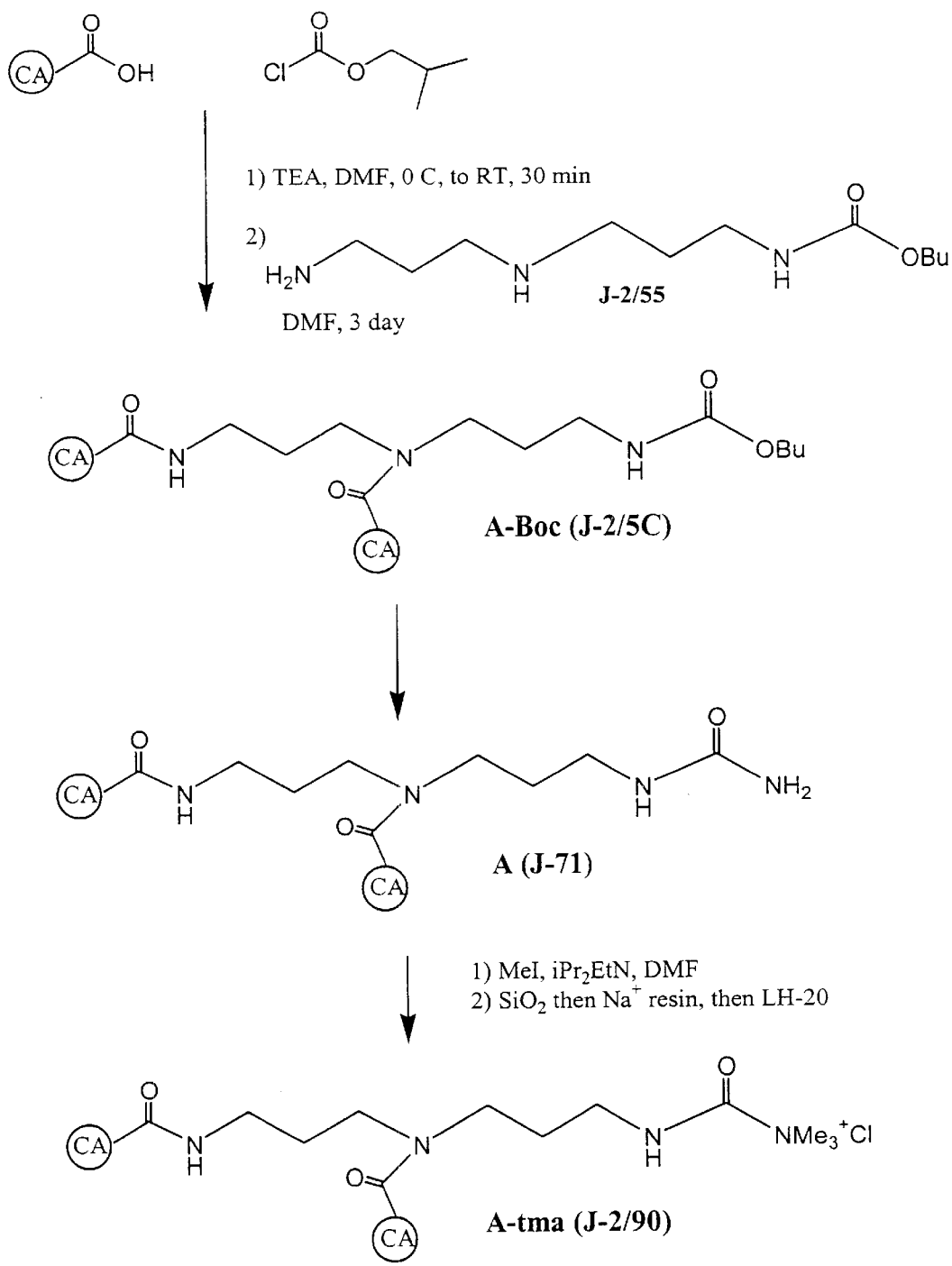
FIG. 35 shows a protocol that was used to synthesize A-tma and A-HCl, which are analogs of Syn3 that exhibit increased solubility in aqueous solution.

A-TMA was synthesized as shown in FIG. 35. Briefly, cholic acid (CA) (2.0 g, 5 mmol) in DMF (30 mL, 0° C.) was treated with $Et_3N$ (0.72 mL, 5.1 mmol) and then, with care, isobutyl chloroformate (0.67 mL, 5.1 mmol). The mixture was stirred for three days and resulted in one compound. This was readily purified on $SiO_2$, eluting with DCM/MeOH (6:1 to 4:1). After 30 min. at room temperature, a solution of the amine (J-2/55) (522 mg, 2.26 mmol) in DMF (4 mL) was added. The amine was synthesized according to Han, Y- P and Hang, H- S, *Bull. Korean Chem. Soc.* (1994) 15: 1025–1027. 1.8 g of the resulting compound, J-2/5C (BOC-A), was obtained, resulting in a 72% yield.

The amine (250 mg, 61/11, 0.27 mmol) in DMF (10 mL) was treated with Hungs base (diisopropylethylamine) (200 μL, 1 .15 mmol) and MeI (75 μL, 1.2 mmol). TLC showed mainly one compound, plus a few impurities. The reaction mixture was concentrated under vacuum and applied to a silica column eluted with $MeCN/AcOH/H_2O$ (4:1:1). The middle fractions were combined and subjected to ion exchange chromatography on the $Na^+$ form of Dowex 50W-X8-200 cation exchange resin, eluted with 1:10.5 M NaCl/MeOH. The purest fractions were desalted on LH-20 lipophilic Sephadex and lyophilized to give the pure trimethyl ammonium chloride (J-2/90 (A-tma)). 82 mg of the resulting compound was obtained, resulting in a 32% yield.

To obtain A-HCl, BOC-A (1.0 g, 1 mmol) in MeOH (60 mL) was treated with a solution of AcCl in MeOH (2 mL in 20 mL) at 0° C. The reaction was slowly allowed to attain room temperature. TLC after 3 h showed no starting material. Following evaporation (with EtOH/toluene), the residue was applied to the $Na^+$ form of a Dowex 50W-X8-200 ion exchange column. However, the product passed straight through. Elution with 0.5 M NaCl did not produce any further material. Flash chromatography on $SiO_2$ was successful (DCM/MeOH/$H_2O$; 60:35:5), although the product seemed to elute in two bands. NMR showed the late and early fractions to be the same. 650 mg of the resulting compound, A-HCl, was obtained, resulting in a 65% yield. It was noted that base treatment (-Ome or resin) can change the TLC behavior of the product.

Example 17

A-tma and A-HCl Enhance Gene Transfer in Vivo

This Example demonstrates that the compounds A-tma and A-HCl have gene transfer activity in vivo.

Methods
1. Preparation of Solutions for Administration:

A concentration of 1 mg/ml was chosen for initial testing of both compounds. For determination of the gene transfer activity for each of these compounds, the level of β-galactosidase activity obtained following administration of Syn3 analog/virus/buffer was compared to the activity when using the virus/buffer alone.

The solution of A-TMA was prepared by dissoluting 10 mg of A-TMA into 10 ml Dulbecco's PBS. Glycerol was added to provide a final concentration of 10 mg/ml. All solutions were sterile filtered prior to use (0.2 μm Acrodisc syringe filter). The virus (BGCG 70AAB) was diluted 1:10 into either this A-TMA solution, or into Dulbecco's PBS-glycerol prior to administration.

Since A-HCl is not completely soluble in saline, and since dissolution into $dH_2O$ resulted in a solution whose pH was 4.7, a Tris-buffered solution was chosen for dissolution of A-HCl whose composition was as follows:

Dissolution buffer (Buffer D)
2.8 mM Tris, pH 7.5
1.2 mM $NaH_2PO_4$
2 mM $MgCl_2$
0.2% sucrose
10 mg/ml glycerol
Final pH 6.5

Ten mg of A-HCl was dissolved into this buffer and sterile filtered prior to use (0.2 μm Acrodisc suring filter). The virus (BGCG 70AAB) was diluted 1:10 into this solution prior to administration. For comparison, the virus diluted into this buffer without A-HCl was also tested.

2. In Vivo Administration

Female HSD rats were anesthetized using isofluorane. The rats were trans-uretherally catheterized into the bladder using PE50 tubing lubricated with K-Y jelly. A tie-off was installed on the external urethra to prevent back leakage. Urine, if any, was removed and the bladder was flushed with 0.5 ml PBS and emptied. rAd was diluted to the desired concentration (1:10) and instilled for 45 minutes. The dosing material was removed, noting the return volume. The bladder was flushed with 0.5 ml PBS and emptied. The tie-off and catheter were removed, and the animals were allowed to recover in cages.

After 48 hours, the animals were sacrificed and their bladders inflation fixed with 0.5 ml fixative for 1 hour. The bladders were then rinsed overnight and whole organ X-gal staining was conducted.

Results

The two compounds both gave enhanced gene transfer activity compared to controls. The levels of gene transfer activity are summarized in Table III. Relative levels of gene transfer activity are shown; highest levels of gene transfer activity are indicated by '++++', and low levels are indicated by '+' (no transfer activity indicated by 0).

TABLE III

Assessment of gene transfer activity in animals using water-soluble Syn3 analogs

| Animal # | Solution Composition | Gene Transfer Activity |
|---|---|---|
| #297 | PBS/1% Glycerol | 0 |
| #298 | 1 mg/ml A-TMA in PBS/1% Glycerol | ++ |
| #988 | 1 mg/ml A-TMA in PBS/1% Glycerol | ++ |
| #989 | 1 mg/ml A-TMA in PBS/1% Glycerol | ++ |
| #384 | Buffer D | 0 |
| #385 | 1 mg/ml A-HCl in Buffer D | ++ |
| #386 | 1 mg/ml A-HCl in Buffer D | ++ |
| #387 | 1 mg/ml A-HCl in Buffer D | ++ |

Conclusions

The two compounds A-tma and A-HCl both demonstrated gene transfer activity significantly above those levels obtained by controls. Although these levels are lower than those obtained using Syn3 in Tween-80, they do indicate that gene transfer enhancement is possible using an aqueous based Transfection Enhancing Agent such as A-tma and A-HCl. The compound A-SC, in which the lactose moiety of Syn3 is replaced with a succinic anhydride moiety was not effective as a gene transfer enhancing compound. This compound gave gene transfer activity at levels equal to controls (data not shown). Table IV summarizes the gene transfer results using these compounds compared to the gene transfer activity of Syn3 at 1 mg/ml.

TABLE IV

Summary of gene transfer activity of water-soluble Syn3 analogs

| Compound | Concentration | Gene transfer activity |
|---|---|---|
| A-TMA | 1 mg/ml | ++ |
| A-HCl | 1 mg/ml | ++ |
| A-SC | 1 mg/ml | 0/+ |
| Syn3 | 1 mg/ml | ++++ |

Since both compounds have been found to have much greater solubility in $dH_2O$ (up to 5 mg/ml), it is likely that increasing the concentration of these analogs will result in even greater gene transfer activity in vivo.

All publications, patents, and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:
1. A compound of Formula III:
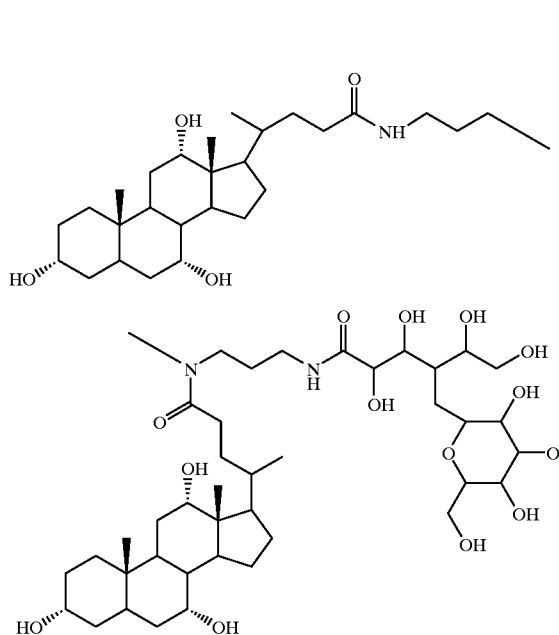
2. A compound of Formula IV:
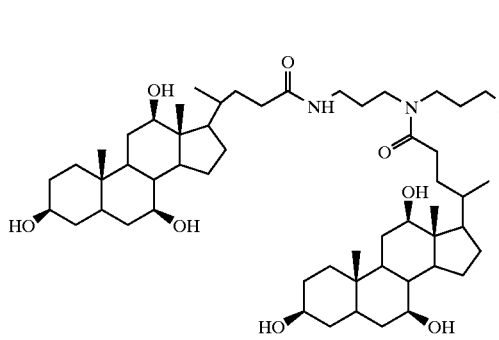
3. A compound of Formula V:
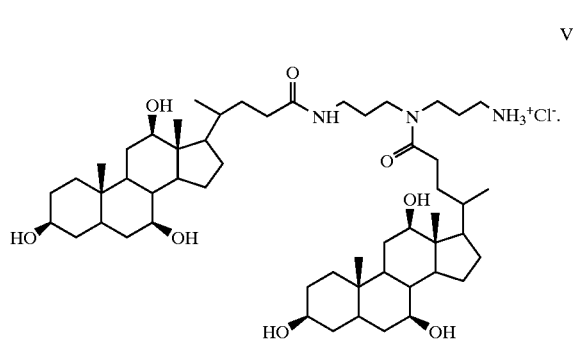
4. A delivery enhancing compound of Formula II:
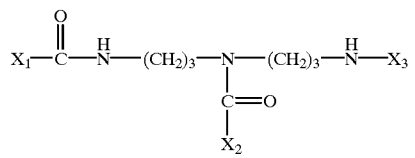
wherein:
$X_1$ and $X_2$ are selected from the group consisting of
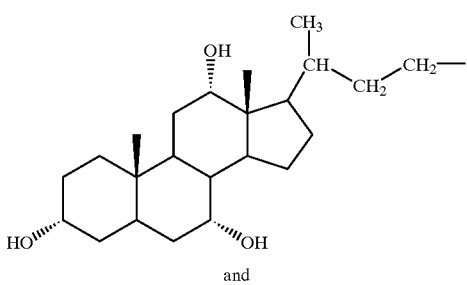
and
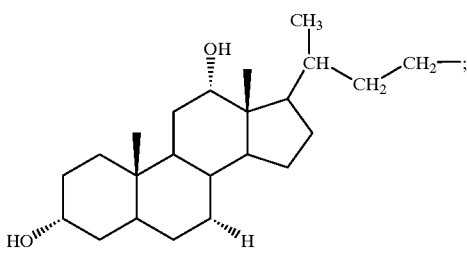
and $X_3$ is a saccharide group.
5. The compound according to claim 4, wherein $X_1$ and $X_2$ are both
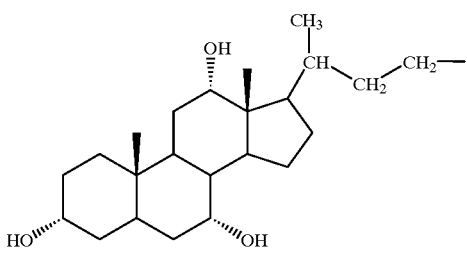
and $X_3$ is a glucose group.
* * * * *

UNITED STATES PATENT AND TRADEMARK OFFICE
CERTIFICATE OF CORRECTION

PATENT NO. : 6,392,069 B2  
DATED : May 21, 2002  
INVENTOR(S) : Engler et al.

Page 1 of 2

It is certified that error appears in the above-identified patent and that said Letters Patent is hereby corrected as shown below:

Column 37,
Lines 5-28, please delete,

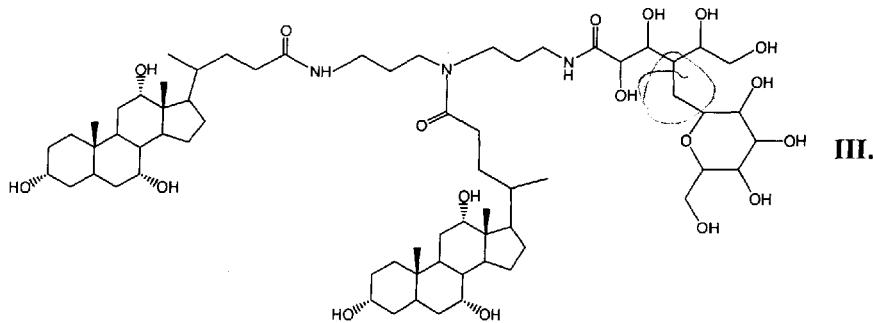

and replace with

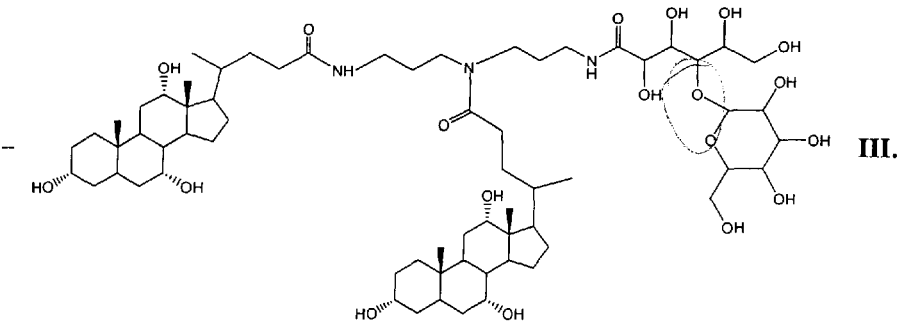

UNITED STATES PATENT AND TRADEMARK OFFICE
CERTIFICATE OF CORRECTION

PATENT NO.   : 6,392,069 B2
DATED        : May 21, 2002
INVENTOR(S)  : Engler et al.

It is certified that error appears in the above-identified patent and that said Letters Patent is hereby corrected as shown below:

Column 37,
In figure 21, first compound (Syn 3), please delete,

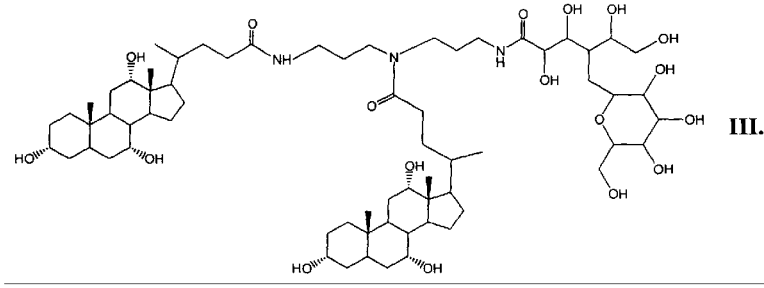

and replace with

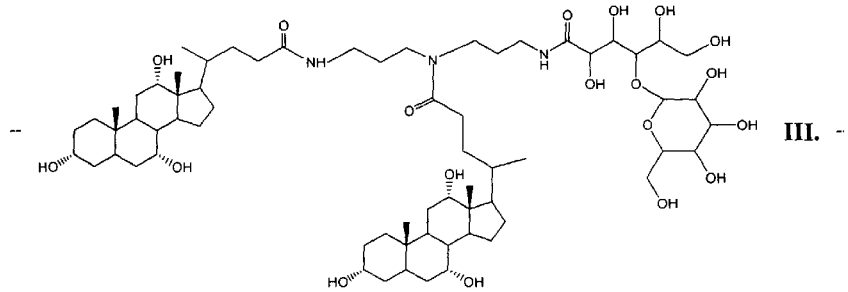

Signed and Sealed this

Twenty-fourth Day of August, 2004

JON W. DUDAS
*Director of the United States Patent and Trademark Office*